(12) United States Patent
Spence

(10) Patent No.: US 11,938,020 B2
(45) Date of Patent: Mar. 26, 2024

(54) SYSTEM, DEVICES AND METHODS FOR ANCHORING AND/OR SEALING A HEART VALVE PROSTHESIS

(71) Applicant: Mitral I Inc., Louisville, KY (US)

(72) Inventor: Paul A. Spence, Aventura, FL (US)

(73) Assignee: Mitral I, Inc., Louisville, KY (US)

( * ) Notice: Subject to any disclaimer, the term of this patent is extended or adjusted under 35 U.S.C. 154(b) by 220 days.

(21) Appl. No.: 17/216,125

(22) Filed: Mar. 29, 2021

(65) Prior Publication Data

US 2022/0031451 A1 Feb. 3, 2022

Related U.S. Application Data

(63) Continuation of application No. 16/081,154, filed as application No. PCT/US2017/019858 on Feb. 28, 2017, now abandoned.

(60) Provisional application No. 62/349,830, filed on Jun. 14, 2016, provisional application No. 62/301,924, filed on Mar. 1, 2016.

(51) Int. Cl.
*A61F 2/24* (2006.01)

(52) U.S. Cl.
CPC .......... *A61F 2/2409* (2013.01); *A61F 2/2439* (2013.01); *A61F 2/2445* (2013.01); *A61F 2/246* (2013.01); *A61F 2/2418* (2013.01); *A61F 2/2457* (2013.01); *A61F 2210/0014* (2013.01); *A61F 2210/0085* (2013.01); *A61F 2220/0008* (2013.01); *A61F 2230/0006* (2013.01); *A61F 2230/0013* (2013.01); *A61F 2250/0003* (2013.01); *A61F 2250/0013* (2013.01); *A61F 2250/0069* (2013.01)

(58) Field of Classification Search
CPC ........ A61F 2/2409; A61F 2/2442–2448; A61F 2/246–2463; A61F 2250/0003
See application file for complete search history.

(56) References Cited

U.S. PATENT DOCUMENTS

| | | |
|---|---|---|
| 5,370,685 A | 12/1994 | Stevens |
| 5,554,185 A | 9/1996 | Block et al. |
| 7,276,078 B2 | 10/2007 | Spenser et al. |
| 7,435,257 B2 | 10/2008 | Lashinski et al. |
| 7,445,630 B2 | 11/2008 | Lashinski et al. |
| 7,534,259 B2 | 5/2009 | Lashinski et al. |
| 7,556,645 B2 | 7/2009 | Lashinski et al. |
| 7,628,805 B2 | 12/2009 | Spenser et al. |
| 8,012,201 B2 | 9/2011 | Lashinski et al. |

(Continued)

FOREIGN PATENT DOCUMENTS

| | | |
|---|---|---|
| CN | 102639179 A | 8/2012 |
| CN | 103237523 A | 8/2013 |

(Continued)

OTHER PUBLICATIONS

Extended European Search Report for European Application No. 17760579.7, dated Oct. 15, 2019, 8 pages.

(Continued)

*Primary Examiner* — Rebecca S Preston

(57) ABSTRACT

Methods, devices and systems for anchoring and/or sealing a heart valve prosthesis and, in particular, a mitral valve prosthesis (202). Inflatable elements (204, 206) are used to seal and anchor the mitral valve prosthesis (202) and/or other elements associated with repairing a native mitral valve.

25 Claims, 59 Drawing Sheets

(56) References Cited

U.S. PATENT DOCUMENTS

| | | |
|---|---|---|
| 8,092,525 B2 | 1/2012 | Eliasen et al. |
| 8,308,796 B2 | 11/2012 | Lashinski et al. |
| 8,377,118 B2 | 2/2013 | Lashinski et al. |
| 8,449,606 B2 | 5/2013 | Eliasen et al. |
| 8,523,940 B2 | 9/2013 | Richardson et al. |
| 8,568,477 B2 | 10/2013 | Lashinski et al. |
| 8,888,844 B2 | 11/2014 | Eliasen et al. |
| 8,894,705 B2 | 11/2014 | Eliasen et al. |
| 9,216,076 B2 | 12/2015 | Mitra et al. |
| 9,232,998 B2 | 1/2016 | Wilson et al. |
| 2006/0004442 A1 | 1/2006 | Spenser et al. |
| 2008/0039935 A1* | 2/2008 | Buch ............... A61F 2/2454 623/2.38 |
| 2008/0133002 A1 | 6/2008 | Gelbart et al. |
| 2009/0030435 A1 | 1/2009 | Burnett et al. |
| 2009/0088836 A1 | 4/2009 | Bishop et al. |
| 2009/0099653 A1 | 4/2009 | Suri et al. |
| 2011/0066233 A1 | 3/2011 | Thornton et al. |
| 2011/0160846 A1 | 6/2011 | Bishop et al. |
| 2011/0166648 A1* | 7/2011 | Robin ............... A61F 2/2436 623/2.1 |
| 2012/0016468 A1 | 1/2012 | Robin et al. |
| 2012/0022629 A1 | 1/2012 | Perera et al. |
| 2012/0165930 A1 | 6/2012 | Gifford, III et al. |
| 2012/0277855 A1 | 11/2012 | Lashinski et al. |
| 2012/0310330 A1 | 12/2012 | Buchbinder et al. |
| 2013/0304200 A1 | 11/2013 | McLean et al. |
| 2013/0331929 A1 | 12/2013 | Mitra et al. |
| 2014/0243966 A1 | 8/2014 | Garde et al. |
| 2014/0243968 A1 | 8/2014 | Padala |
| 2014/0296975 A1 | 10/2014 | Tegels et al. |
| 2015/0073547 A1 | 3/2015 | Eliasen et al. |
| 2015/0216658 A1 | 8/2015 | Braido |
| 2016/0089234 A1* | 3/2016 | Gifford, III ............ A61F 2/2487 623/2.18 |
| 2020/0121454 A1 | 4/2020 | Spence |

FOREIGN PATENT DOCUMENTS

| | | |
|---|---|---|
| CN | 103889472 A | 6/2014 |
| CN | 103974674 A | 8/2014 |
| WO | WO-2011069048 A2 | 6/2011 |
| WO | WO-2012106602 A2 | 8/2012 |
| WO | WO-2013059747 A1 | 4/2013 |
| WO | WO-2014056701 A1 | 4/2014 |
| WO | WO-2015173609 A1 | 11/2015 |
| WO | WO-2017151566 A1 | 9/2017 |

OTHER PUBLICATIONS

First Office Action for Chinese Application No. 201780025645.2, dated Feb. 25, 2020, 13 pages.
International Search Report and Written Opinion for International Application No. PCT/US2017/019858, dated Jul. 20, 2017, 11 pages.
Second Office Action for Chinese Application No. 201780025645.2, dated Dec. 21, 2020, 17 pages.

\* cited by examiner

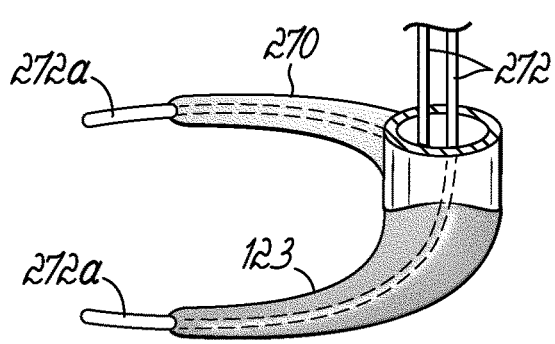
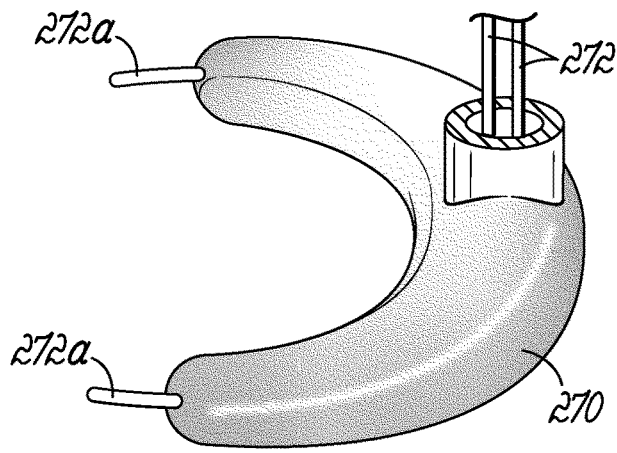
FIG. 15A   FIG. 15B
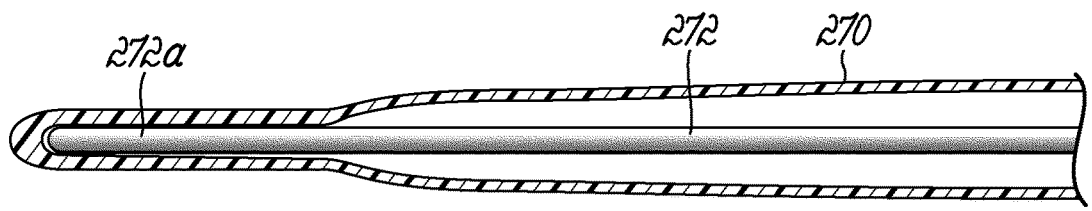
FIG. 16A
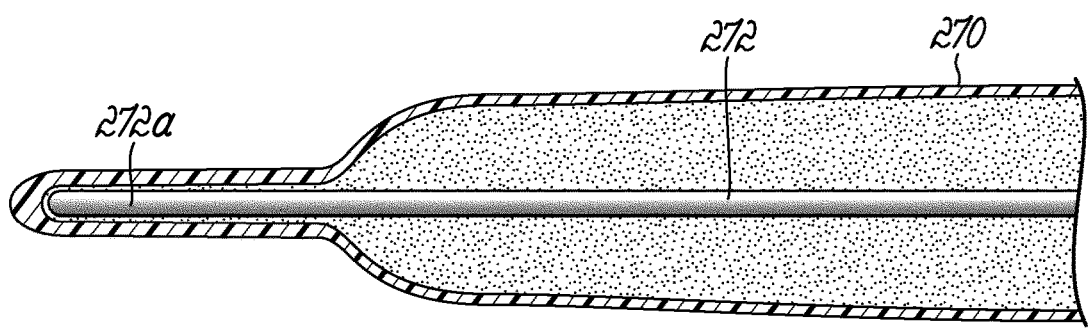
FIG. 16B

SYSTEM, DEVICES AND METHODS FOR ANCHORING AND/OR SEALING A HEART VALVE PROSTHESIS

CROSS-REFERENCE TO RELATED APPLICATIONS

This application is a continuation of U.S. patent application Ser. No. 16/081,154, which is a U.S. National Phase application, filed under 35 U.S.C. § 371, of International Application No. PCT/US17/19858, filed on Feb. 28, 2017, which claims the priority of U.S. Provisional Patent Application Ser. No. 62/301,924, filed Mar. 1, 2016 and U.S. Provisional Patent Application Ser. No. 62/349,830, filed Jun. 14, 2016, the disclosures of which are incorporated by reference herein.

BACKGROUND

Despite a considerable amount of effort, catheter based repair and replacement of the mitral valve remains a challenge. Aortic valve replacement via a catheter has advanced remarkably quickly. The aortic valve has an annulus that can serve as an anchor for a prosthetic valve that is positioned inside a native valve. The mitral valve has no natural anchor that can be used to support the valve. So devices to replace the mitral valve require an anchoring or fastening system to hold a prosthesis in place. The procedure requires delivery of a valve prosthesis and an anchoring system. Not surprisingly, given the high pressure inside the heart, stability of the implanted mitral valve is an issue. Not infrequently, there is anatomic variation in the mitral valve. So a leak around an implanted valve can occur. And sometimes the anchoring is tenuous. Also, some anchoring systems are bulky to adapt to the numerous anatomic variations. It would be useful to have additional approaches to anchor and/or seal a valve prosthesis that are potentially less bulky, more secure and which also reduce leak.

Surgical experience may be useful. Surgery allows a considerable amount of flexibility—each patient can be treated to account for variations observed at the time of operation. The mitral valve varies considerably from patient to patient. The diameter of the annulus ranges widely. The amount of leaflet tissue is also very variable—some patients have abundant leaflet tissue and others little. The chordae can be long or short. The ventricle can be small or very large.

Many patients have a large valve diameter and a large amount of valve tissue. Surgeons have found that leaving leaflet tissue behind (i.e., not excising all the excess leaflet tissue), and even folding leaflet tissue is very useful. The folded leaflet tissue reduces the size of the annulus and fills space so a smaller valve can be used. This creates a circle of a leaflet pledget that narrows the diameter of the annulus. The retained leaflet also makes the attachment more secure. The retained leaflet acts as a shock absorber by spreading the load around the anchoring of the valve.

Folding and tensioning leaflet tissue and thereby chordae tendinae, also helps during mitral valve replacement. The mass of folded tissue creates a very solid anchor for a valve. Also, the tensioned leaflet-chordal system reduces valve movement. If the leaflets and chordae are not tensioned, the prosthetic valve can move as the heart beats. Valve motion after valve replacement is very dangerous. The movement places rhythmic loads on the attachment and with about 100,000 heartbeats per day, the risk of valve disruption, tissue tearing and leak is magnified.

Tensioning of the chordae after mitral valve replacement may also help the function of the left ventricle after valve replacement. The tensioned chordae help keep the correct shape of the left ventricle to optimize the filling and emptying and the function of the heart muscle.

It would be useful to have a flexible way to treat leaks or to eliminate the potential for leaks and also to provide further options to anchor a valve in the mitral position.

Inflatable devices have been used in a variety of locations. They have been used in intraperitoneal procedures to move viscera and allow a surgeon to operate without risk of injury to adjacent abdominal contents. Direct Flow Medical has also developed an aortic valve that has "inflatable" components that help to anchor the valve.

SUMMARY

An anchor for sealing and/or stabilizing a mitral valve prosthesis at the location of the native mitral valve comprises an elongate inflatable element configured to be directed under at least a portion of the native mitral valve and a wire operatively coupled to the elongate inflatable element and configured to guide the elongate inflatable element under at least the portion of the native mitral valve. The wire may be fixed to the elongate inflatable element to prevent any sliding movement between the elongate inflatable element and the wire. The elongate inflatable element is configured for delivery through a mitral valve commissure and/or for implantation at least partially between the left ventricular wall and the chordae tendinae. The wire may be coupled to the elongate inflatable element in a manner allowing sliding movement between the elongate inflatable element and the wire.

A method for implanting an anchor for sealing and/or stabilizing a mitral valve prosthesis at the location of the native mitral valve comprises directing an elongate inflatable element under at least a portion of the native mitral valve and using a wire operatively coupled to the elongate inflatable element to guide the elongate inflatable element under the portion of the native mitral valve. The wire may be fixed to the elongate inflatable element, and using the wire further comprises guiding the elongate inflatable element without any sliding movement between the elongate inflatable element and the wire. Directing the elongate inflatable element further comprises implanting the elongate inflatable element at least partially between the left ventricular wall and the chordae tendinae and/or at least one of the native mitral valve leaflets. The wire may be coupled to the elongate inflatable element in a manner allowing sliding movement between the elongate inflatable element and the wire, and using the wire further comprises guiding the elongate inflatable element while sliding the elongate inflatable element along the wire. Directing the elongate inflatable element further comprises implanting the elongate inflatable element at least partially between the left ventricular wall and the chordae tendinae and/or at least one of the native mitral valve leaflets.

A system for replacing a native mitral valve of a patient with a mitral valve prosthesis, comprises an expansible mitral valve prosthesis configured to be delivered through a catheter to the position of the native mitral valve of a patient. The expansible mitral valve prosthesis includes anchoring arms on a lower portion thereof configured to bend upward to capture the native mitral valve leaflets upon deployment from the catheter and an inflatable structure capable of being inflated upon delivery at the position of the native mitral valve and engaging with the native mitral valve leaflets and/or the anchoring arms of the mitral valve prosthesis for stabilizing implantation of the mitral valve prosthesis at the position of the native mitral valve. The inflatable structure further comprises a discontinuous balloon structure extending at least partially around the mitral valve prosthesis. The inflatable structure further comprises discrete and separately inflatable balloons.

A system for replacing a native mitral valve of a patient with a mitral valve prosthesis, comprises an expansible mitral valve prosthesis configured to be delivered through a catheter to the position of the native mitral valve of a patient, the expansible mitral valve prosthesis including an expansible stent portion configured to be delivered to the position of the native mitral valve and then expanded and an inflatable structure that may be carried on the expansible stent portion and capable of being inflated upon delivery at the position of the native mitral valve and providing sealing and/or stabilization between the expansible mitral valve prosthesis and the native mitral valve of the patient. The inflatable structure further comprises first and second sealing balloons adapted to be positioned generally on opposite (diametrical) sides of the mitral valve prosthesis. The inflatable structure further comprises at least a pair of sealing balloons positioned adjacent to each other and configured to provide a seal at one commissure of the native mitral valve. The inflatable structure further comprises a continuous annular balloon adapted to be positioned in surrounding relation to the mitral valve prosthesis. The inflatable structure further comprises a discontinuous balloon structure configured to be positioned above and/or below the annulus of the native mitral valve. The inflatable structure further comprises a discontinuous balloon structure configured to be positioned generally around the mitral valve prosthesis. The system further comprises reinforcing structure coupled with the discontinuous balloon structure. The reinforcing structure further comprises wire and/or inflatable reinforcement balloons. First and second inflatable leaflet capturing members are coupled to the inflatable structure and configured to be inflated to capture and stabilize the native mitral valve leaflets. The system further comprises a mitral valve prosthesis and a plurality of anchoring arms coupled with the mitral valve prosthesis and configured to engage the inflatable structure and/or at least one of the native mitral valve leaflets. The anchoring arms further comprise hook-like members that may include fabric or other material to form a "paddle" shape.

A method of implanting an expansible mitral valve prosthesis in the heart of a patient comprises delivering an inflatable structure under at least one leaflet of the native mitral valve, delivering the expansible mitral valve prosthesis to the native mitral valve, inflating the inflatable structure, and anchoring the mitral valve prosthesis in place at least partially by using the inflatable structure. Delivering the inflatable structure under at least one leaflet further comprises guiding the inflatable structure with a wire. Guiding the inflatable structure with a wire further may comprise guiding the inflatable structure using a wire fixed to the inflatable structure such that there is no relative sliding movement between the wire and the inflatable structure. Guiding the inflatable structure with a wire further may instead comprise guiding the inflatable structure by sliding the inflatable structure along the wire. Delivering the inflatable structure under at least one leaflet further comprises directing the inflatable structure between the chordae tendonae and a wall of the left ventricle.

A method of implanting an expansible mitral valve prosthesis in the heart of a patient, wherein the mitral valve prosthesis includes a plurality of anchoring arms coupled to a lower portion thereof, and the method comprises delivering an inflatable structure under at least one leaflet of the native mitral valve, delivering the expansible mitral valve prosthesis to the native mitral valve, and engaging the anchoring arms with the inflatable structure and/or the at least one leaflet to anchor the expansible mitral valve prosthesis. The anchoring arms further comprise hook-like members and the method further comprises engaging the hook-like members with the inflatable structure and/or the at least one leaflet of the native mitral valve.

A system for replacing a native mitral valve of a patient with a mitral valve prosthesis, comprises an expansible mitral valve prosthesis configured to be delivered through a catheter to the position of the native mitral valve of a patient, the expansible mitral valve prosthesis including an expansible stent portion configured to be delivered to the position of the native mitral valve and then expanded, an inflatable structure capable of being delivered under at least one leaflet of the native mitral valve and anchoring the expansible mitral valve prosthesis with the native mitral valve of the patient, and a plurality of anchoring arms coupled with the mitral valve prosthesis and configured to engage the inflatable structure and/or the at least one native mitral valve leaflet. The anchoring arms further comprise hook-like members.

A system for anchoring a mitral valve prosthesis comprises a delivery catheter including a lumen and a distal opening communicating with the lumen, and an inflatable structure received in a collapsed form within the lumen of the delivery catheter and adapted to be delivered from the distal opening, the inflatable structure capable of being inflated upon delivery from the distal opening and formed as an inflated anchoring element positioned between the mitral valve prosthesis and the native mitral valve of a patient, wherein the inflatable structure is capable of being delivered from the distal opening to the native mitral valve position of the patient separately from the mitral valve prosthesis. A mitral valve prosthesis is capable of being delivered to the mitral valve position of the patient and expanded radially outward and into engagement with the inflatable element. The inflatable structure further comprises first and second sealing balloons adapted to be positioned on opposite sides of the mitral valve prosthesis and at least a pair of sealing balloons positioned adjacent to each other and configured to provide a seal at one commissure of the native mitral valve. The inflatable structure further comprises a continuous annular balloon adapted to be positioned in surrounding relation to the mitral valve prosthesis. The inflatable structure further comprises a discontinuous balloon structure including first and second portions adapted to be positioned generally on opposite sides of the mitral valve prosthesis, wherein the continuous annular balloon is configured to be positioned above the annulus of the native mitral valve and the discontinuous balloon structure is configured to be positioned below the annulus of the native mitral valve. Reinforcing structure is coupled with the discontinuous balloon structure and comprises wire and/or inflatable reinforcement balloons. First and second inflatable leaflet capturing members are configured to be inflated to capture and stabilize the native mitral valve leaflets. The system further comprises a mitral valve prosthesis and a plurality of anchoring arms coupled with the mitral valve prosthesis and configured to engage the inflatable structure and/or at least one of the native mitral valve leaflets. The anchoring arms further comprise hook-like members.

A method of implanting an expansible mitral valve prosthesis in the heart of a patient comprises delivering an inflatable structure to the native mitral valve, delivering the expansible mitral valve prosthesis to the native mitral valve separately from the inflatable structure, and anchoring the mitral valve prosthesis in position to replace the native mitral valve of the patient by inflating the inflatable structure and placing the inflatable element generally between the expansible mitral valve prosthesis and the native mitral valve. The method further comprises delivering the inflatable structure and the expansible mitral valve prosthesis percutaneously through the venous system of the patient to the native mitral valve. Delivering the inflatable structure further comprises delivering a first balloon of the inflatable structure below the mitral valve into the left ventricle of the heart and a second balloon of the inflatable structure above the mitral valve into the left atrium of the heart. The inflatable structure further comprises first and second sealing balloons and delivering the inflatable structure further comprises positioning the first sealing balloon on one side of the native mitral valve and positioning the second sealing balloon on the opposite (diametrical) side of the native mitral valve and sealing first and second commissures of the native mitral valve respectively with at least the first and second balloons. The inflatable structure further comprises third and fourth sealing balloons, and delivering the inflatable structure further comprises positioning one pair of the sealing balloons so as to provide a seal at one commissure of the native mitral valve and positioning another pair of the sealing balloons so as to provide a seal at the other commissure of the native mitral valve. The inflatable structure further comprises a continuous annular balloon, and delivering the inflatable element further comprises positioning the continuous annular balloon in surrounding relation to the mitral valve prosthesis. The inflatable structure further comprises a discontinuous balloon structure connected with the continuous annular balloon, and the delivering the inflatable structure further comprises positioning the continuous annular balloon above the annulus of the native mitral valve and positioning the discontinuous balloon structure below the annulus of the native mitral valve. The inflatable structure further comprises a discontinuous balloon structure and delivering the inflatable structure further comprises positioning the discontinuous balloon structure above or below the annulus of the native mitral valve. The method further comprises reinforcing the discontinuous balloon structure with wire and assisting the delivery of the discontinuous balloon structure using a wire. Delivering the inflatable structure further comprises delivering first and second inflatable leaflet capturing members and inflating the first and second inflatable leaflet capturing members to capture and stabilize the native mitral valve leaflets. The expansible mitral valve prosthesis further comprises a plurality of anchoring arms coupled to a lower portion thereof, and the method further comprises engaging the anchoring arms with the inflatable structure and/or at least one native mitral valve leaflet to assist with stabilizing the expansible mitral valve prosthesis. The anchoring arms further comprise hook-like members and the method further comprises engaging the hook-like members under the leaflets of the native mitral valve.

A system for replacing a native mitral valve of a patient comprises a mitral valve prosthesis including a generally tubular portion and a flange portion extending radially outward from the tubular portion, the flange portion configured to provide an anchor above the native mitral valve annulus in the left atrium of the patient, an inflatable structure configured to be positioned below at least a portion of the native mitral valve leaflets and a plurality of anchoring arms coupled with the mitral valve prosthesis and configured to engage the inflatable structure and/or at least one of the native mitral valve leaflets to assist with anchoring the mitral valve prosthesis in place. The anchoring arms further comprise hook-like members. The inflatable structure has a generally semi-annular, elongate shape for locating between the left ventricular wall and the chordae tendinae and/or the native mitral valve leaflets and to generally follow the curvature of the native mitral valve annulus. The system further comprises a wire operatively coupled to the inflatable element and configured to guide the inflatable element into position between the left ventricular wall and the chordae tendinae and/or the native mitral valve leaflets and to generally follow the curvature of the native mitral valve annulus. The wire may be fixed to the inflatable element to prevent any sliding movement between the inflatable element and the wire. The wire instead may be coupled to the inflatable element in a manner allowing sliding movement between the inflatable element and the wire.

A mitral valve prosthesis, comprises a generally tubular portion, a plurality of anchoring arms coupled with a lower section of the tubular portion and configured to be located below the native mitral valve leaflets bend upwards upon deployment and an inflatable structure coupled to the anchoring arms and configured to engage and trap the native mitral valve leaflets upon deployment of the anchoring arms. The mitral valve prosthesis further comprises a flange portion extending radially outward from the tubular portion, the flange portion configured to provide an anchor above the native mitral valve annulus in the left atrium of the patient.

A mitral valve commissure seal comprises an inflatable structure including a first portion extending in a first direction for passing through a commissure of a native mitral valve and being inflatable to prevent blood leakage through the commissure, and a second portion extending generally transverse to the first portion and configured to be positioned above or below the native mitral valve annulus and being inflatable to serve as an anchor for a mitral valve prosthesis.

A system for replacing a native mitral valve of a patient comprises a mitral valve prosthesis including a generally tubular portion and a flange portion extending radially outward from the tubular portion, the flange portion configured to provide an anchor above the native mitral valve annulus in the left atrium of the patient and an inflatable structure configured to be positioned at the position of at least one commissure of the native mitral valve and inflated to at least assist with sealing the commissure against blood leakage.

An inflatable structure that is shaped to generally follow a native mitral valve annulus and allows for a mitral valve prosthesis to be implanted, wherein the mitral valve prosthesis has a smaller diameter than the native mitral valve annulus. An inflatable anchor formed in a generally semi-annular elongate shape so as to be configured for positioning under at least one native mitral valve leaflet and in a plane generally parallel to the native mitral valve annulus and assists in anchoring a mitral valve prosthesis. The inflatable anchor is delivered via at least one anchoring arm of the mitral valve prosthesis and is capable of being delivered into position through a commissure of the native mitral valve. The inflatable anchor further comprises a portion thereof configured to seal a gap formed by a commissure of the native mitral valve. The portion extends generally transverse to another portion of the inflatable anchor and is configured to be implanted in position to extend through the commissure.

An inflatable anchor system for a mitral valve prosthesis comprises at least one inflatable anchor formed in a generally annular or semi-annular shape so as to be configured for positioning above and/or below the native mitral valve annulus to assist in anchoring a mitral valve prosthesis, and wherein the inflatable anchor includes a portion that is capable of being inflated at the location of a mitral valve annulus for sealing the commissure against blood leakage.

A strategy that improves the quality of mitral valve replacement and reduces the size of the prosthesis that is used, and uses leaflet tissue to cushion the implant and that tensions the leaflet-cordal system could be useful for catheter based mitral valve replacement. An inflatable system may be used to achieve such goals. In addition, the inflatable system can be adjusted to allow for different sized patients and different mitral valve and mitral annulus composition. The amount of inflation or the number of inflatables that are actually filled (some could be filled optionally) can provide considerable flexibility.

The drawing figures that follow show how inflatable anchor components can be used to, for example:
  reduce the annulus diameter and to reduce the need for a large valve prosthesis;
  provide natural leaflet pledgetting around the prosthetic valve;
  tension the leaflet-chordal apparatus to reduce prosthesis movement and reduce the risk of disruption and failure;
  improve left ventricle (LV) function by tensioning the leaflets and chordae
  improve sealing of the prosthetic valve to prevent leak;
  adjust filling of the inflatable anchor to adapt to different sizes of valve diameter, leaflet and chordate;
  fold leaflet and tension chordal tissue; and/or
  trap leaflet and chordal tissue.

In another embodiment, the invention provides a system for replacing a native mitral valve of a patient with a mitral valve prosthesis including an inflatable mitral valve prosthesis and an inflatable stabilizing structure. The inflatable mitral valve prosthesis is configured to be delivered through a catheter to the position of the native mitral valve of a patient. The inflatable stabilizing structure is capable of being inflated upon delivery at the position of the native mitral valve and engaging with native tissue for stabilizing implantation of the mitral valve prosthesis at the position of the native mitral valve.

In another embodiment, the invention provides a system for replacing a native mitral valve of a patient with a mitral valve prosthesis including an inflatable mitral valve prosthesis and an inflatable stabilizing structure. The inflatable mitral valve prosthesis is configured to be delivered through a catheter to the position of the native mitral valve of a patient. The inflatable mitral valve prosthesis includes an inflatable portion configured to be delivered to the position of the native mitral valve and then expanded. The inflatable stabilizing structure is carried on the inflatable portion and is capable of being inflated upon delivery at the position of the native mitral valve and providing sealing and/or stabilization between the inflatable mitral valve prosthesis and the native mitral valve of the patient. The inflatable stabilizing structure may further comprise first and second sealing balloons adapted to be positioned generally on opposite sides of the inflatable mitral valve prosthesis. The inflatable stabilizing structure may further comprise a continuous annular balloon adapted to be positioned in surrounding relation to the inflatable mitral valve prosthesis. The inflatable stabilizing structure may further comprise a discontinuous balloon structure configured to be positioned above and/or below the annulus of the native mitral valve.

The inflatable stabilizing structure may further comprise a discontinuous balloon structure configured to be positioned generally around the inflatable mitral valve prosthesis. The system may further comprise reinforcing structure coupled with the discontinuous balloon structure. The reinforcing structure may further comprise wire. The system may further comprise first and second inflatable leaflet capturing members coupled to the inflatable mitral valve prosthesis and/or the inflatable stabilizing structure and configured to be inflated to capture and stabilize the native mitral valve leaflets.

The invention, in another aspect, further provides a method of implanting an inflatable mitral valve prosthesis in the heart of a patient. The method includes delivering an inflatable stabilizing structure under at least one leaflet of the native mitral valve. The inflatable mitral valve prosthesis is delivered to the native mitral valve. The inflatable stabilizing structure is inflated, and the inflatable mitral valve prosthesis is anchored in place at least partially by using the inflatable stabilizing structure. Delivering the inflatable stabilizing structure under at least one leaflet may further comprise guiding the inflatable structure with a wire.

In another embodiment, the invention provides a system for repairing a native mitral valve of a patient with a mitral valve prosthesis including a mitral clip and an inflatable sealing structure. The mitral clip is configured to be delivered through a catheter to the position of the native mitral valve of a patient. The mitral clip is configured to capture and clip together the native leaflets of the mitral valve. The inflatable sealing structure is capable of being inflated upon delivery at the position of the native mitral valve and engaging with native tissue for sealing leaks through the native mitral valve. The inflatable sealing structure may be independent of, or physically coupled to the mitral clip. The inflatable sealing structure may be physically coupled to the mitral clip by an inflatable connecting structure.

In another aspect, the invention provides a method of applying a mitral clip to the native mitral valve of a patient. The method includes delivering the mitral clip under the leaflets of the native mitral valve, and capturing the leaflets with the mitral clip. An inflatable sealing structure is delivered to the native mitral valve. The inflatable sealing structure is inflated into engagement with native tissue to seal one or more leaks through the native mitral valve. As with any of the methods herein, the steps or portions of each method may be performed in any order depending on the application and/or desires of the person performing the method.

Various additional advantages and features will become more readily apparent to those of ordinary skill in the art upon review of the following detailed description of the illustrative embodiments taken in conjunction with the accompanying drawings.

BRIEF DESCRIPTION OF THE DRAWINGS

FIG. 15A is a perspective view illustrating another alternative embodiment for a lower, discontinuous inflatable element portion including a guidewire incorporated therewith, and showing the inflatable element in an uninflated condition.

FIG. 15B is similar to FIG. 15A, but illustrates the inflatable element in its inflated condition.

FIG. 16A is a cross sectional view showing the tip of an inflatable element similar to that shown in FIGS. 15A and 15B, but illustrating the end of the wire encapsulated within the balloon element, and the balloon element in its uninflated condition.

FIG. 16B is a cross sectional view similar to FIG. 16A, but illustrating the inflatable element in its inflated condition.

DETAILED DESCRIPTION

Figure 1:
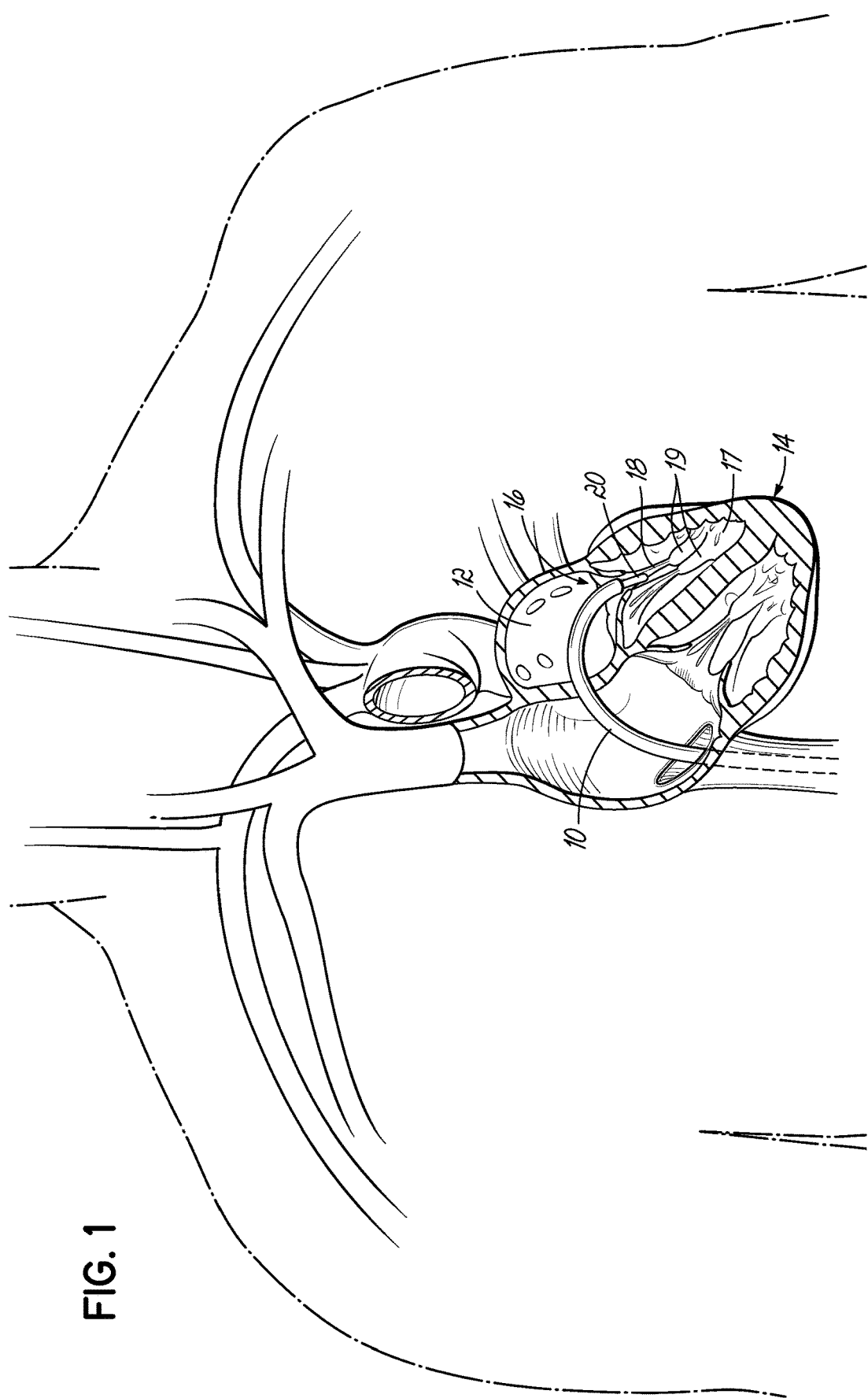
FIG. 1 is a schematic view showing the heart of a patient in cross section and one exemplary approach for delivering devices in accordance with various embodiments of this invention.

In all of the various embodiments shown and described herein, like structure will be indicated in the drawings using like reference numerals. Therefore, respective description of such like elements is not needed and will not generally be included in this written description.

FIG. 1 illustrates one approach to a mitral valve procedure usable in connection with the various devices, systems and methods disclosed herein. A catheter 10 having a lumen and a distal opening is advanced in a peripheral vein, such as the femoral vein. Here, the catheter 10 is advanced up the inferior vena cava and across the interatrial septum into the left atrium 12 of the heart 14. The distal tip of the catheter 10 is traversing the native mitral valve 16. The heart 14 further includes a left ventricle 17 with chordae tendinae 18 coupling mitral leaflets 16a, 16b with papillary muscles 19. the leaflets 16a, 16b extend from a mitral annulus 16c. Inside the catheter 10, which may be considered a delivery catheter, is a mitral valve prosthesis 20, for example, that may be coupled with or used and implanted independently from an anchor and/or a seal for mitral valve replacement such as described further herein.

Figure 2A:
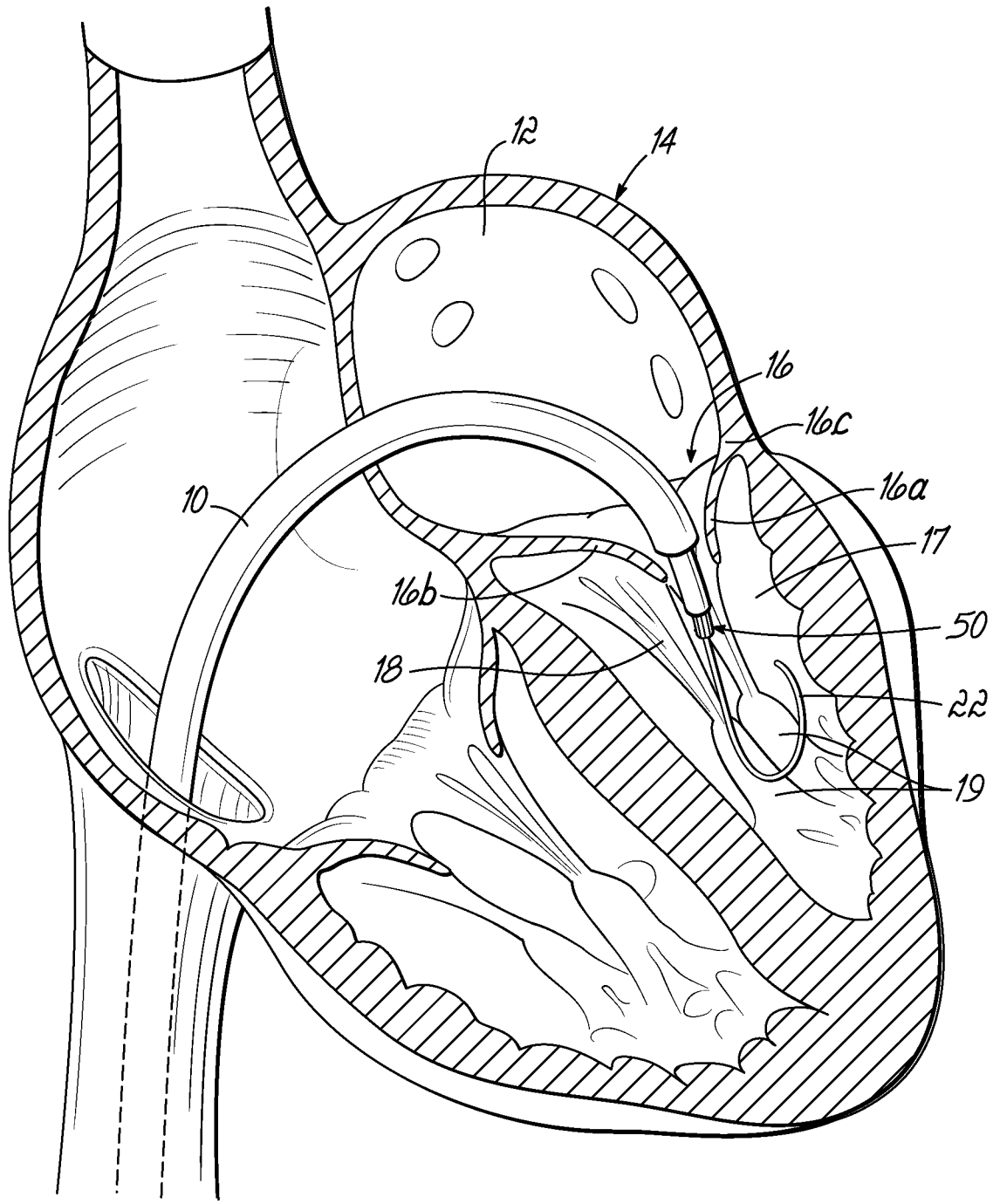
FIG. 2A is an enlarged cross sectional view of the heart showing the introduction of a catheter assembly into the left atrial chamber or atrium of the heart and through the mitral valve into the left ventricle.

FIG. 2 illustrates an enlarged view of the distal delivery catheter 10 within the heart. A guidewire 22 with a U-turn has been advanced under the mitral valve leaflets 16a, 16b of the native mitral valve 16. There are other approaches that may be taken to reach the native mitral valve 16. For example, the native mitral valve 16 may be accessed directly through a surgical procedure, and may be accessed via the apex of the heart. This figure is focused on a transseptal approach, but it will be understood that the various embodiments of this invention may be practiced by using other approaches to the native mitral valve 16 with catheters, or catheter assemblies.

Figure 3:
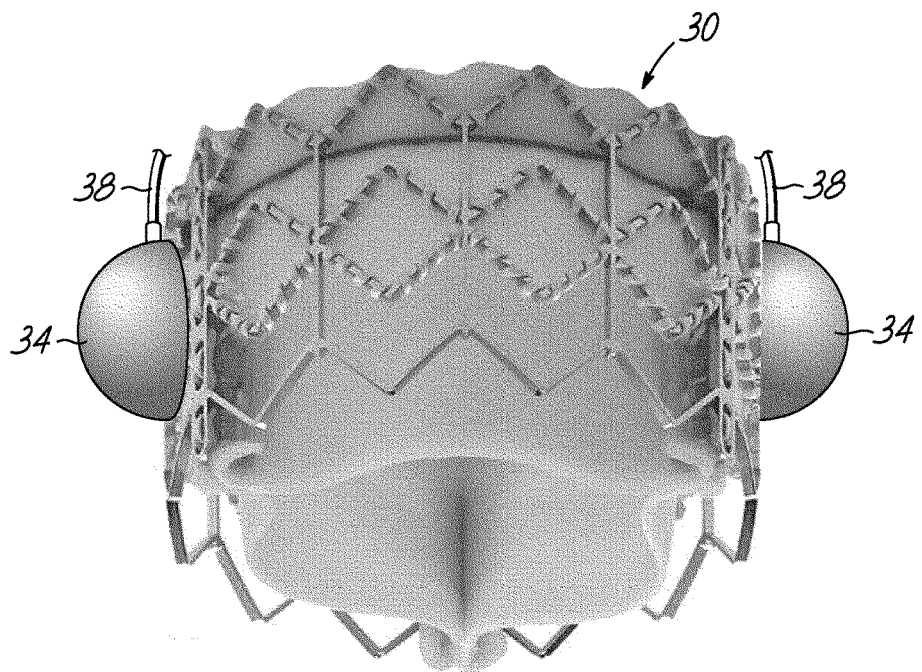
FIG. 3 is a cross sectional view showing an expansible mitral valve prosthesis including a stent and a pair of inflatable sealing balloons.

FIG. 3 illustrates an embodiment of the invention showing a prosthetic heart valve 30 that is normally used in aortic valve procedures. This prosthetic valve is a stent valve, and attached to the stent valve are inflatable sealing balloons 34. A stent valve 30 such as this may be implanted directly if there are extreme calcification conditions of a native mitral valve 16. Alternatively, this stent valve 30 may be implanted in a docking station or unit that is affixed to the native mitral valve and retains this stent valve 30 in place. More commonly, a mitral valve prosthesis for implantation via a catheter has an integrated anchoring mechanism. The sealing balloons 34 may be made from, for example, a polymer and deflated or collapsed for delivery. The sealing balloons 34 can have any shape or size that is useful to the procedure. Attached to the balloons are catheters or tubes 38 that allow delivery of gas or fluids to fill the balloon. The catheters 38 may be detachable leaving a seal on the balloon 34 such that the gas or fluid may not escape. Known in the art are threaded mechanisms to attach these catheters or fluid/gas delivery tubes 38 and this also allows detachment of the fluid or gas delivery tube 38. Initially these fluid or gas delivery tubes or catheters 38 are used to delivery contrast material that is visible on X-ray. Once it is confirmed that the mitral valve prosthesis 30 is in position, the contrast material is replaced with a hardenable fluid material, such as a suitable known polymer, that stays permanently inside the sealing balloon 34. This inflatable sealing balloon 34 may be used not only to seal at the commissure location (with another sealing balloon at the other commissure location), but may also assist with holding the mitral valve prosthesis 30 in place for implantation purposes. An inflatable element, such as the sealing balloons 34, may have a limited use, for example, the treatment of a local leak. The most common site for a leak after mitral valve replacement is at the commissures. But leaks may also occur anywhere and these inflatable elements may be useful at other places for at least that reason. The sealing balloons 34 illustrated in FIG. 3 may be directed so that the sit at the site of the commissures. The sealing balloons 34 may be directly affixed to the mitral valve prosthesis 30, or used with an attached anchoring system (not shown). Such a balloon or inflatable element 34 may even be used on aortic valve procedures. The location or locations of the sealing balloons 34 may be varied, and there may be different numbers of balloons depending on the desired uses. The shapes may also vary.

Figure 4A:
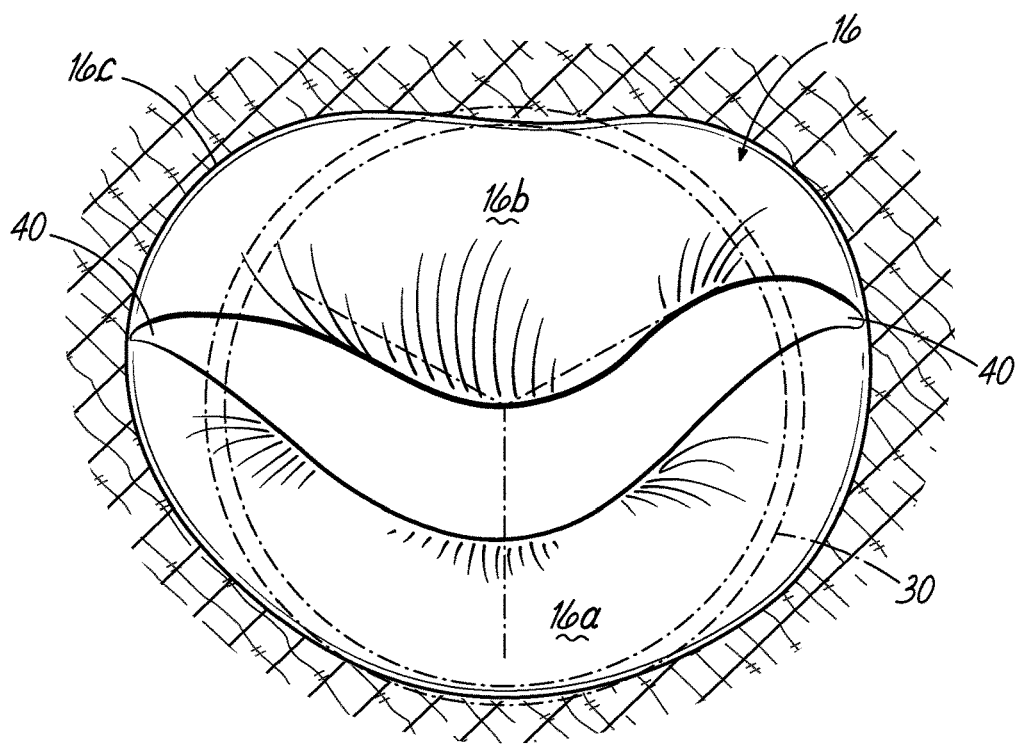
FIG. 4A is a top view of the native mitral valve with the mitral valve prosthesis in dash-dot lines.

FIG. 4A illustrates a mitral valve prosthesis 30 that has been delivered to the location of the native mitral annulus and is viewed from above, i.e., in the left atrium. As shown, gaps 40 may be formed between the leaflets 16a, 16b at the commissures and these represent locations where possible blood leakage may occur, i.e., the flow of blood past the mitral valve prosthesis 30. As shown further in FIGS. 4B and 4C, the two sealing balloons 34 are positioned so that they will locate at the respective commissures. The sealing balloons 34 may be inflated routinely or in response to evidence during the procedure that the valve has a leak around it. Inflating the balloons 34 at the commissures will close or stop up the gap 40 between the leaflets 16a, 16b, thereby preventing or at least lessening the leakage of blood past the mitral valve prosthesis 30. The sealing balloons 34 as shown have a semi-spherical shape. However, the sealing balloon 34 does not have to have this shape and any convenient or desirable shape may be used instead. There may be multiple balloons 34 on a valve prosthesis 30 and the operator may decide which balloon or balloons to inflate depending on the circumstances. Providing multiple sealing balloons 34 may make it easier to implant the prosthesis 30 as the prosthesis may be inserted with any orientation relative to the commissures and then the most appropriate balloon or balloons 34 may be inflated for sealing and/or anchoring purposes. It would also be possible to have a balloon or inflatable element that extends around much more of the circumference of the valve 30 to stop blood leakage. The balloon 34 may also sit or be located higher or lower on the prosthesis 30 than shown by way of illustration.

Figure 4B:
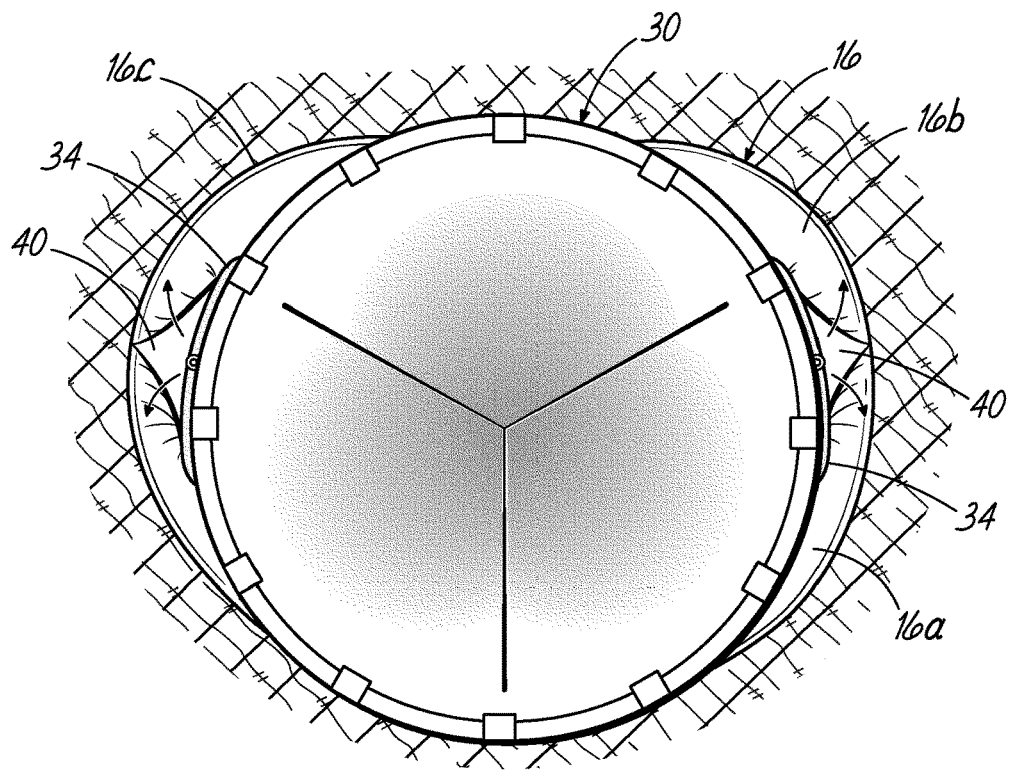
FIG. 4B is a top view of the native mitral valve with the mitral valve prosthesis in place.
Figure 4C:
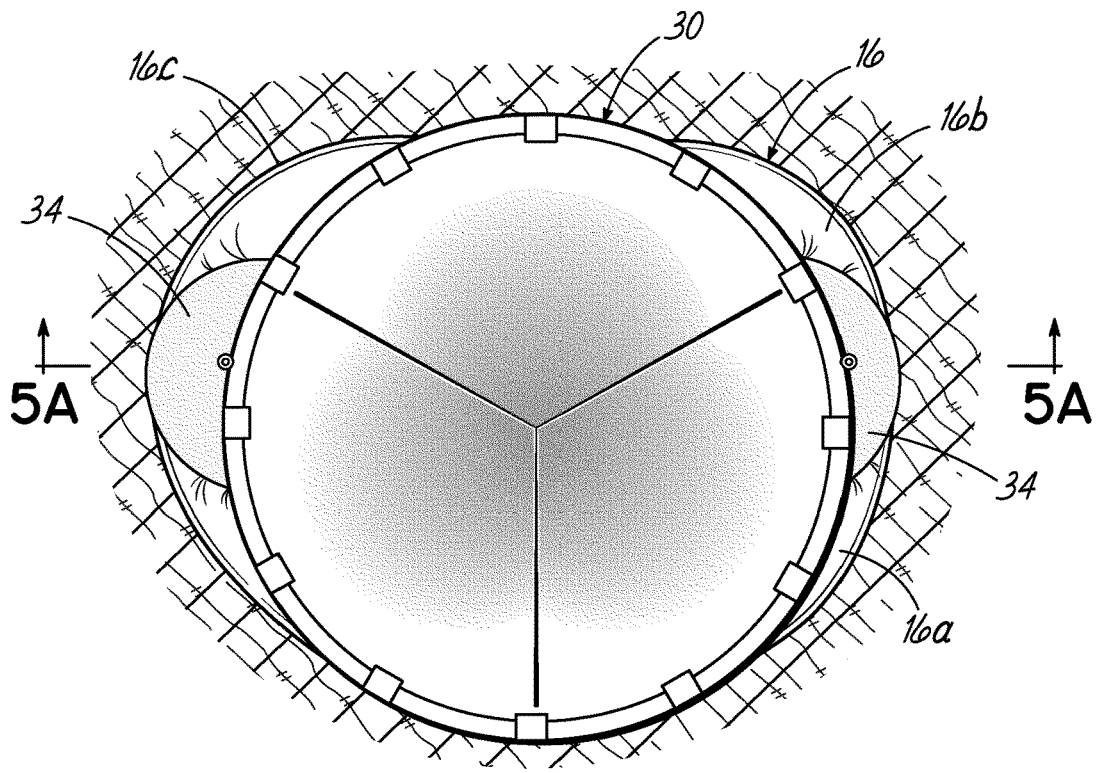
FIG. 4C is a top view similar to FIG. 4B, but showing the two sealing balloons in their inflated conditions.

FIG. 4B illustrates the inflated conditions of the sealing balloons 34. The sealing balloons, in their inflated conditions, expand to the native mitral annulus to completely close off the gap 40 such that there is no significant blood leakage possible. The mitral valve prosthesis 30 is shown for clarity without a docking station or mechanism and without anchoring mechanisms. However, it will be appreciated that various types of docking stations or mechanisms may be provided for anchoring the mitral valve prosthesis 30, such as those that are described hereinbelow.

Figure 5A:
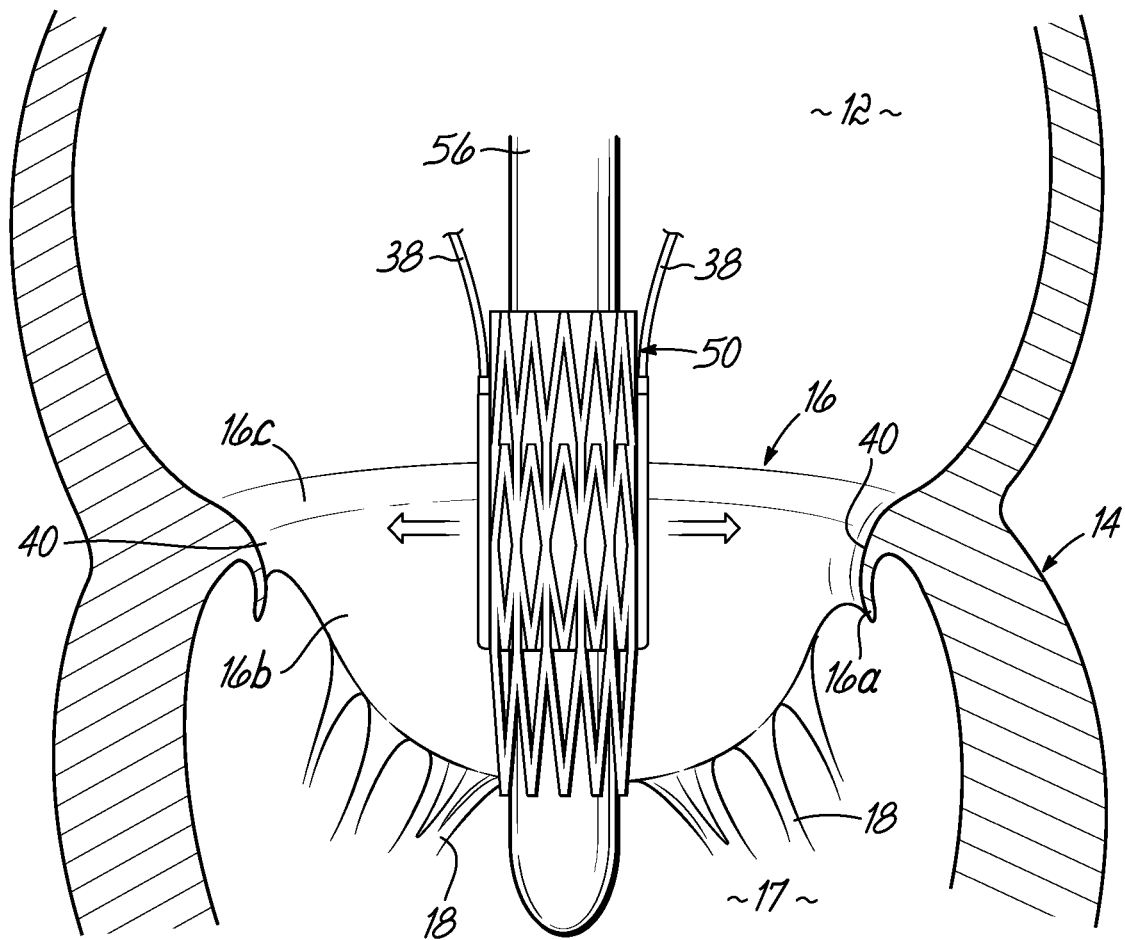
FIG. 5A is a cross sectional view of the native mitral valve taken generally along line 5A-5A of FIG. 4C, but illustrating the expansible stent valve in an unexpanded condition.
Figure 5B:
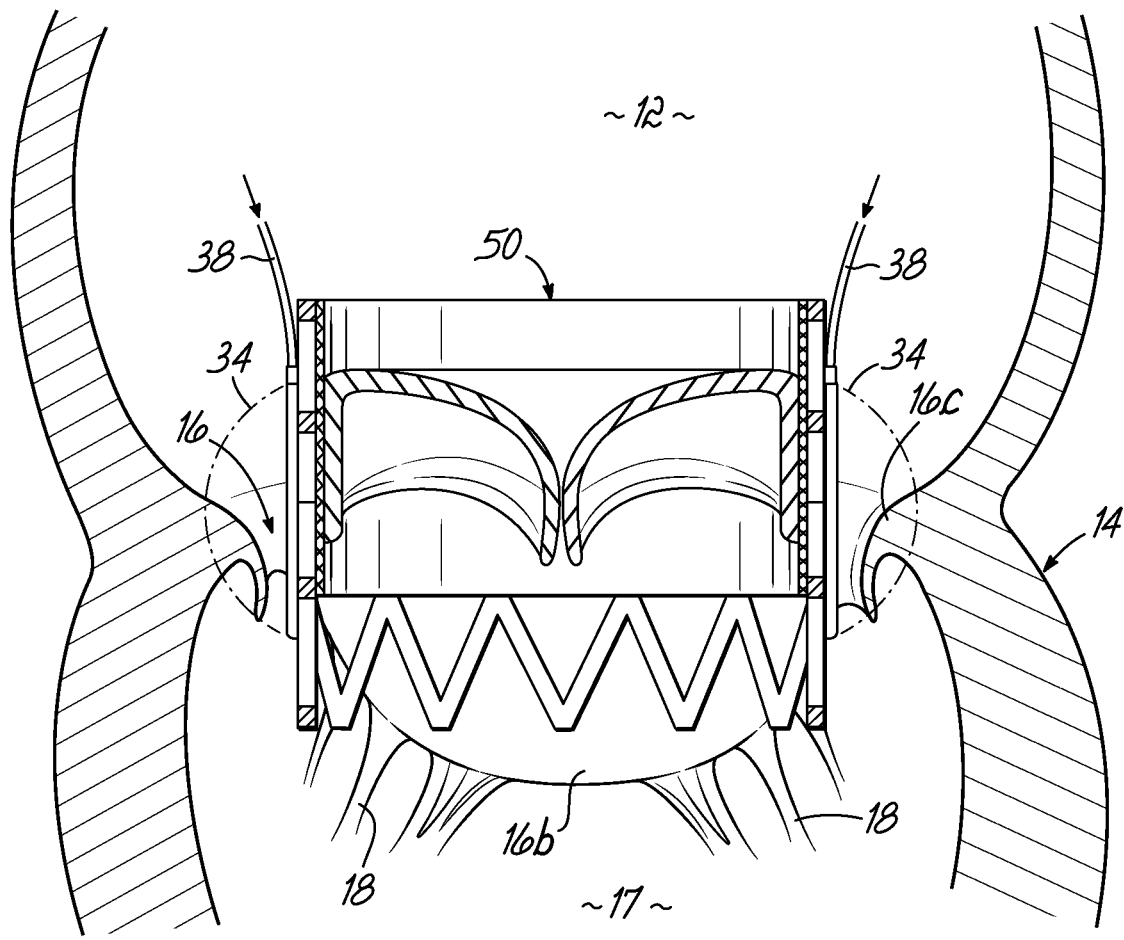
FIG. 5B is a cross sectional view similar to FIG. 5A, but illustrating the expansible stent valve in its expanded condition, and the balloon sealing elements in dash-dot lines.
Figure 5C:
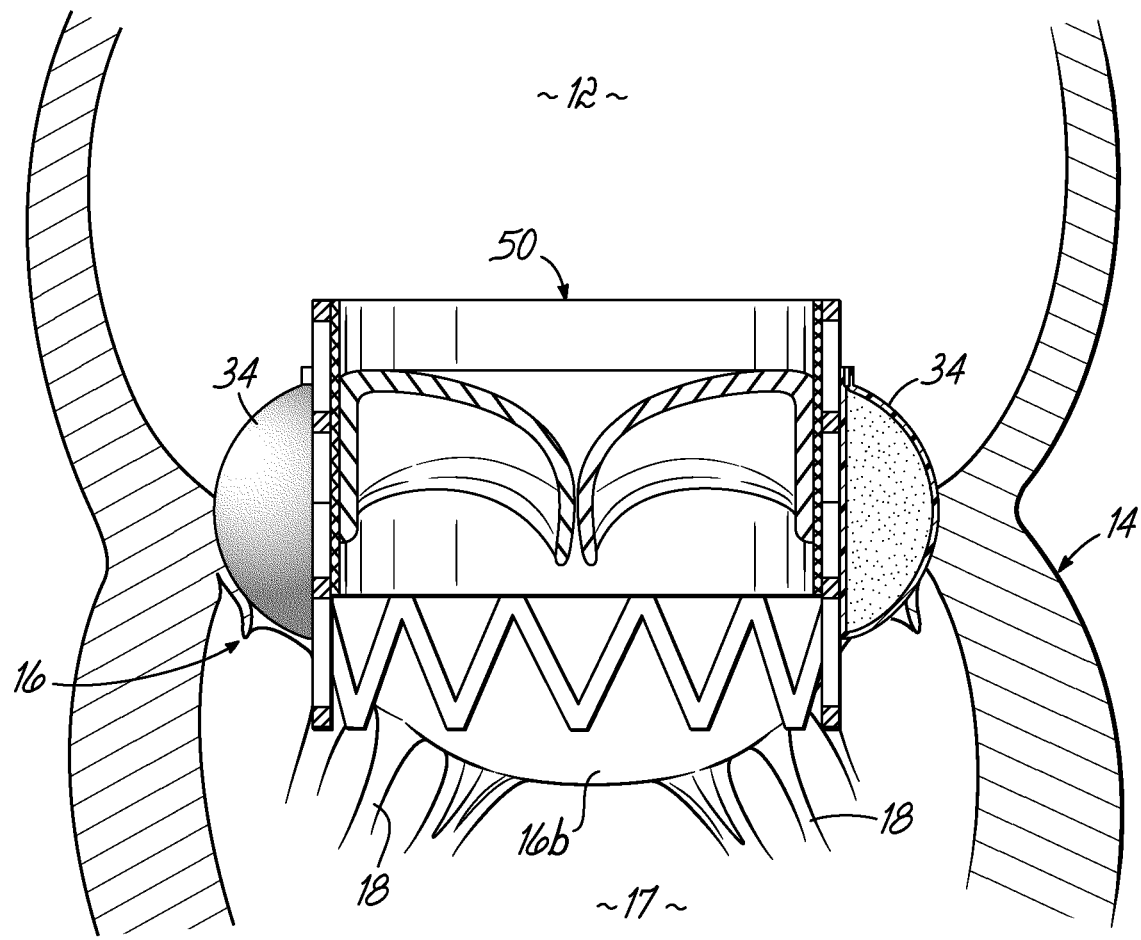
FIG. 5C is a cross sectional view similar to FIG. 5B, but illustrating the inflatable balloons in their inflated and sealing conditions.

FIGS. 5A, 5B and 5C illustrate a mitral valve prosthesis 50, in the form of a stent valve being delivered inside the native mitral valve. As shown in FIG. 5A, the delivery catheter is carrying an expandable stent valve prosthesis 50 that may be inflated to its operating size. Some stent valves are self-expanding and this concept of adding inflatable elements may also be used with such prostheses. The arrows indicate the stent holding the valve is being expanded with a large balloon 56. The inflatable sealing balloons 34 are shown on generally opposite sides of the mitral valve prosthesis 50 in a deflated or collapsed condition for delivery purposes. Attached to the sealing balloons 34 are gas or fluid delivery tubes 38 that will be used to inflate the sealing balloons. FIG. 5B illustrates the mitral valve prosthesis 50 now expanded to its operating size. Again, for clarity there is no docking station or other anchoring mechanism shown, but it will be understood that such a system or mechanism may be used in addition to the sealing balloons 34. The arrows illustrate that fluid or gas is directed into the sealing balloons and the balloons 34 will expand to the size shown in the dash-dot lines. FIG. 5C illustrates that the balloons 34 have been inflated to fill the gaps at the commissures and seal any blood leakage around the mitral valve prosthesis 50. The balloon 34 on the right is shown in cross section to illustrate that it is filled with a hardenable material such as a known polymer that will maintain the shape of the balloon permanently.

Figure 6A:
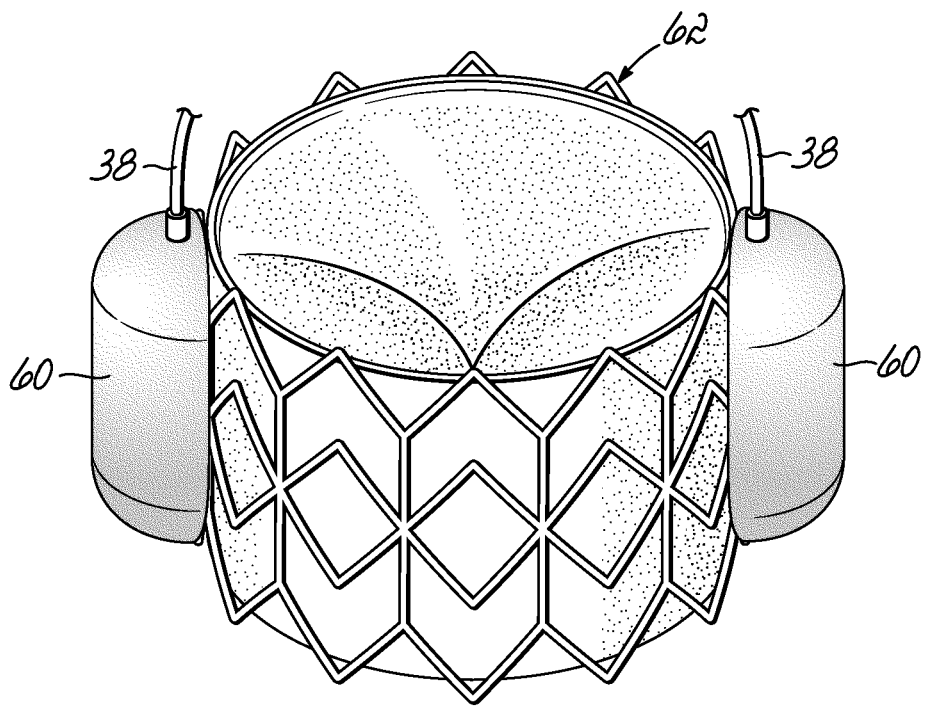
FIG. 6A is a perspective view showing an alternative embodiment for the inflatable sealing balloons on the expansible stent valve.
Figure 6B:
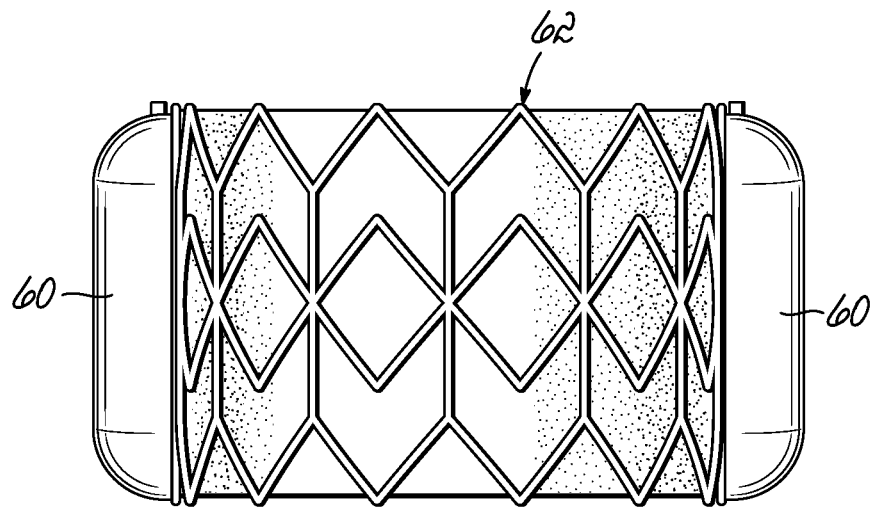
FIG. 6B is a side elevational view of FIG. 6A.
Figure 6C:
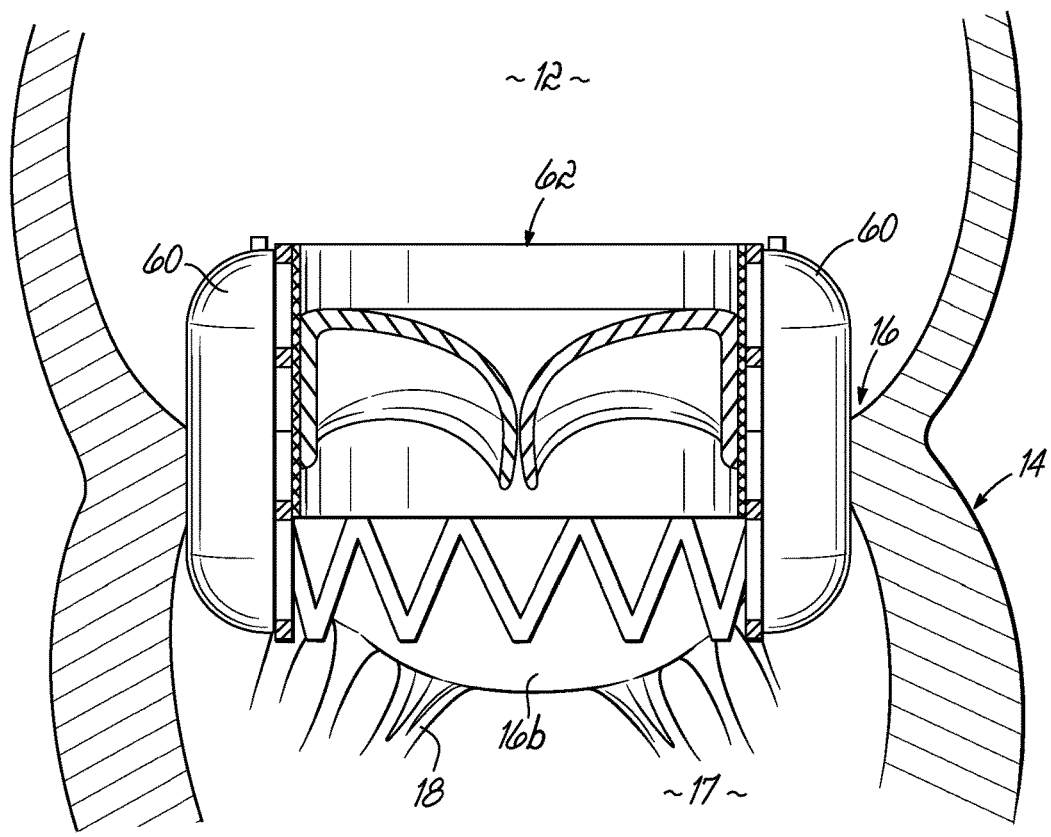
FIG. 6C is a cross sectional view showing the expansible stent valve and balloon sealing elements implanted at the position of a native mitral valve.
Figure 6D:
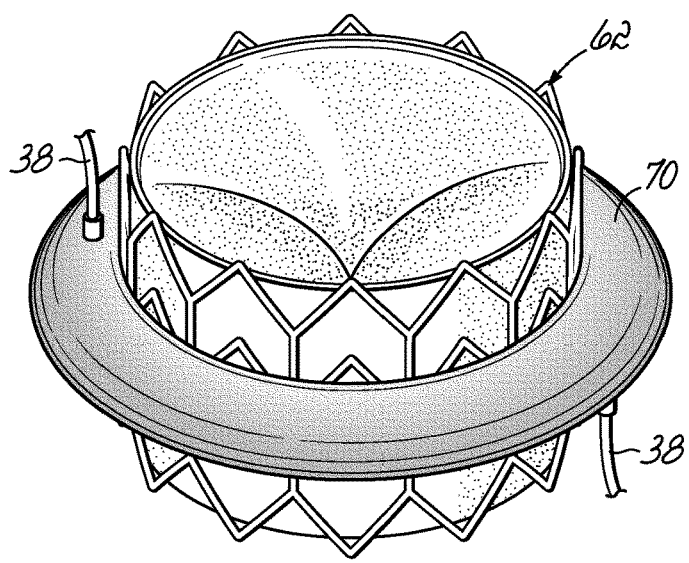
FIG. 6D is a perspective view of an expansible stent valve with an alternative inflatable element in the form of a continuous annular balloon in surrounding relation to the expansible stent valve.

FIGS. 6A through 6D illustrate alternative shapes for sealing balloons 60. FIGS. 6A, 6B and 6C illustrate sealing balloons 60 that have a generally semi-cylindrical shape. The sealing balloons 60 may be attached anywhere on the mitral valve prosthesis 62, or to a valve prosthesis anchoring system (not shown) to stop blood leakage. As shown best in FIGS. 6B and 6C, the sealing balloons 60 may extend along the entire height of the stent valve or other mitral valve prosthesis 62, or they may be shorter than the full height of the valve 62, or even extend beyond one or both upper and/or lower edges of the valve prosthesis 62. The sealing balloons 60 may be attached to the valve prosthesis 62, or may simply reside between the valve prosthesis 62 and the native tissue. Any attachment may be at discrete points on the valve prosthesis 62, or along the entire extent of the sealing balloon 60. The sealing balloon 60 or other inflatable element may be integrated with any part of a docking or anchoring mechanism for the valve prosthesis 62 or to a valve retention mechanism that is attached to the valve prosthesis 62. In other words, the inflatable elements or sealing balloons 60 as described generally may or may not be physically coupled to the valve prosthesis, and may or may not be physically coupled to a separate docking system or anchoring mechanism associated with the valve prosthesis for holding the prosthesis within the native mitral valve. FIG. 6C illustrates a cross sectional view at the location of the native mitral valve. The longer sealing balloon 60, as shown, may be more secure in stopping or sealing any leaks at the commissures. Sometimes leaks may occur at other locations such as clefts in the native mitral valve or in calcified parts of the valve, or where the valve anchoring mechanism tends to produce a leak. These inflatable elements, such as sealing balloons as shown, may be used in different locations to solve any flood leakage problems. FIG. 6D illustrates another alternative inflatable element 70 in the form of a circular or annular inflatable element that generally surrounds the prosthetic valve. Such a structure may be used for sealing and/or anchoring purposes.

Figure 7:
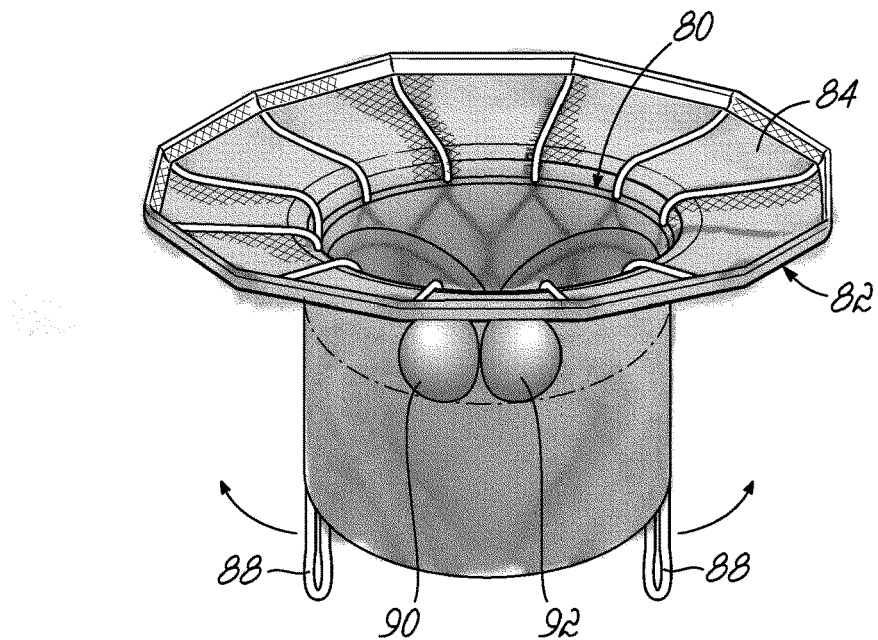
FIG. 7 is a perspective view of another alternative, expansible stent valve for mitral valve replacement, including inflatable balloons for sealing at the commissure locations of the native mitral valve.

FIG. 7 illustrates another example of a type of valve prosthesis that has been used clinically for mitral valve replacement. In this case, a prosthetic valve 80 is contained within an anchoring structure 82. A large skirt or flange 84 is fashioned to sit within the left atrium and create a seal and anchoring structure. At the other end of the valve prosthesis 80, anchoring arms 88 are provided and flip or bend upwardly as indicated by the arrows during deployment and wrap around the native anterior and posterior leaflets 16a, 16b of the mitral valve 16 to keep the prosthetic valve 80 in proper position. These arms 88 are straight during delivery through a catheter and then turn or bend around the leaflets 16a, 16b to perform an anchoring function. FIG. 7 also illustrates a pair of side-by-side sealing balloons 90, 92. This is further shown in FIGS. 8A through 8D, described below.

Figure 8A:
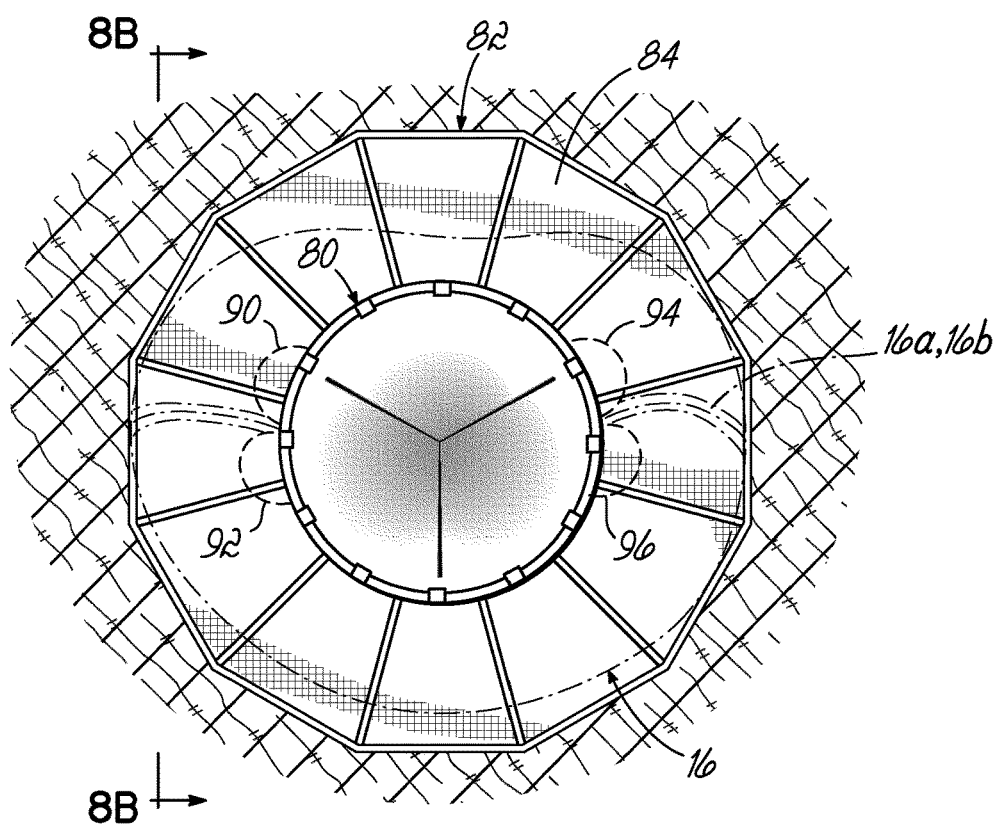
FIG. 8A is a top view of the expansible stent valve of FIG. 7 and shown at the position of the native mitral valve.
Figure 8B:
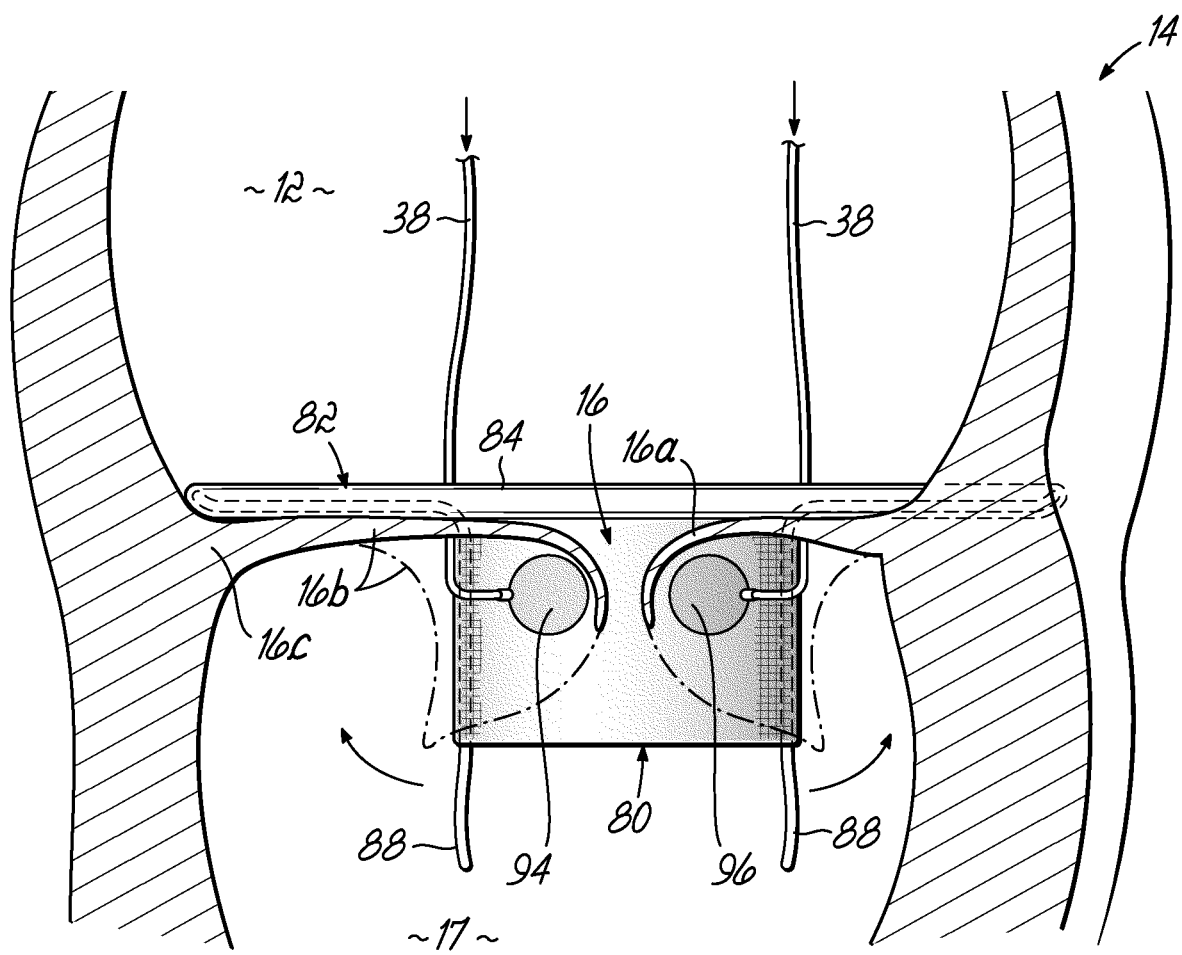
FIG. 8B is a cross sectional view showing the implantation of the expansible stent valve of FIGS. 7 and 8A, prior to full deployment of a pair of arms used to trap the native mitral valve leaflets.
Figure 8C:
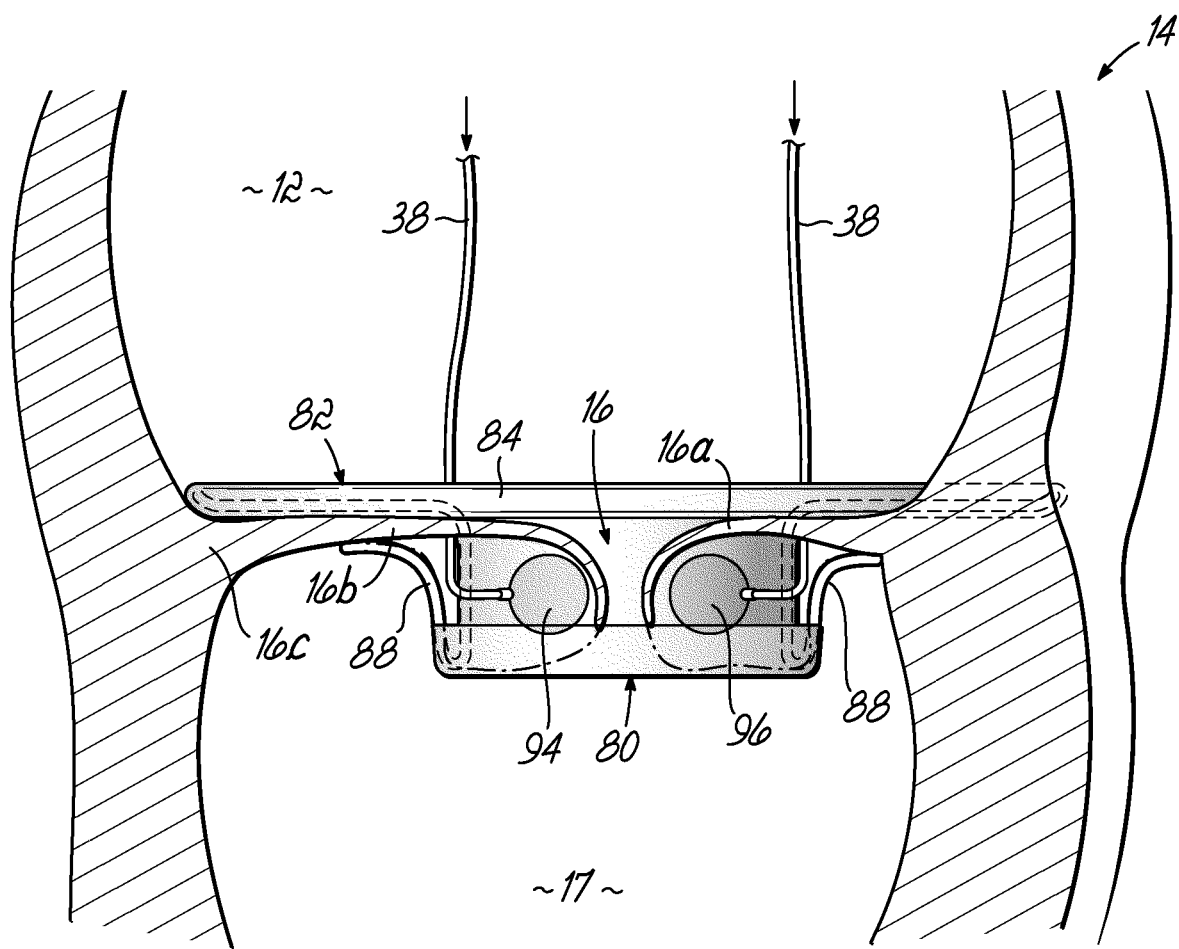
FIG. 8C is a cross sectional view similar to FIG. 8B, but illustrating full deployment of the arms.
Figure 8D:
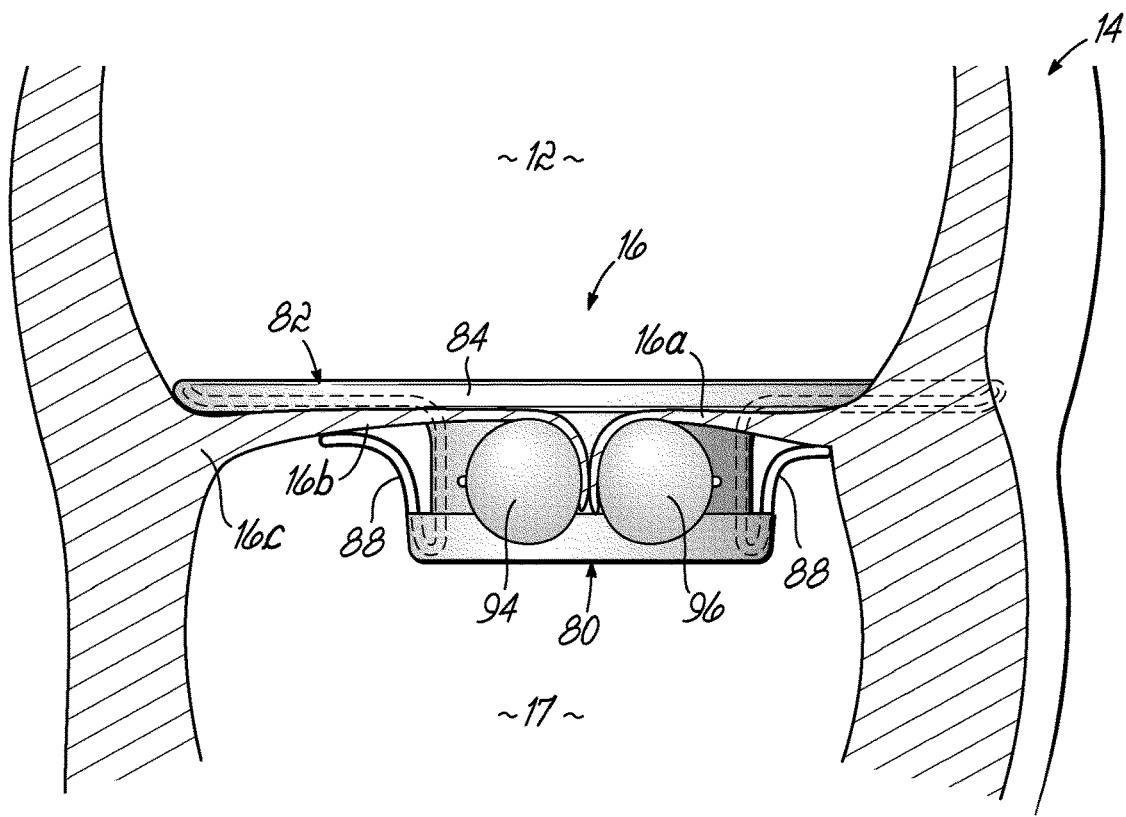
FIG. 8D is a cross sectional view similar to FIG. 8C, but illustrating inflation of one of two pairs of sealing balloons at the commissure locations of the native mitral valve.

FIG. 8A illustrates two pairs of sealing balloons 90, 92, 94, 96 positioned on opposite sides of the mitral valve prosthesis 80. In prior figures, single sealing balloons have been shown as stopping or closing a gap between the anterior and posterior leaflets 16a, 16b at a commissure. In this figure, respective pairs 90, 92, 94, 96 of sealing balloons are inflated under each of the anterior and posterior leaflets 16a, 16b to push the leaflets together and seal the gap for purposes of preventing blood leakage past the valve prosthesis 80. The sealing balloons will be delivered through the commissures (when the procedure is performed from the left atrium) so that they are located below the level of the native mitral valve. Inflation tubes 38 are also shown. The arms 88 are shown before they have wrapped around the leaflets 16a, 16b and the arrows show the arms 88 while wrapped around the anterior and posterior leaflets near their midpoints. The leaflets are shown in dash-dot lines. FIG. 8B illustrates the sealing balloons 90, 92, 94, 96 being inflated through the fluid or gas delivery tubes 38. The anchoring arms 88 on the valve prosthesis 80 have engaged the anterior and posterior leaflets 16a, 16b in a deeper plane than this drawing illustrates for clarity, around the central parts of the anterior and posterior leaflets 16a, 16b. The pair of sealing balloons 94, 96 shown in FIG. 8B at this time sit under the natural leaflets 16a, 16b of the native mitral valve 16. One is located under the anterior leaflet and the other is located under the posterior leaflet. There is a gap between the two leaflets at the commissure as indicated by the comment "leak at commissure." FIG. 8C illustrates the two sealing balloons 94, 96 under the leaflets 16a, 16b being inflated and the two leaflets 16a, 16b being pushed together to stop or plug the leak. The use of a pair of sealing balloons in this manner may also make the valve prosthesis 80 more secure and less inclined to shift position as the heart beats and subjects the valve to high pressure loads and millions of cardiac cycles. FIG. 8D illustrates the fully inflated condition of the sealing balloons 94, 96 and the sealing of the gap between the natural leaflets at the commissure. The same process and result will be used at the opposite commissure as necessary or desired to prevent blood leakage in a similar manner.

Figure 8E:
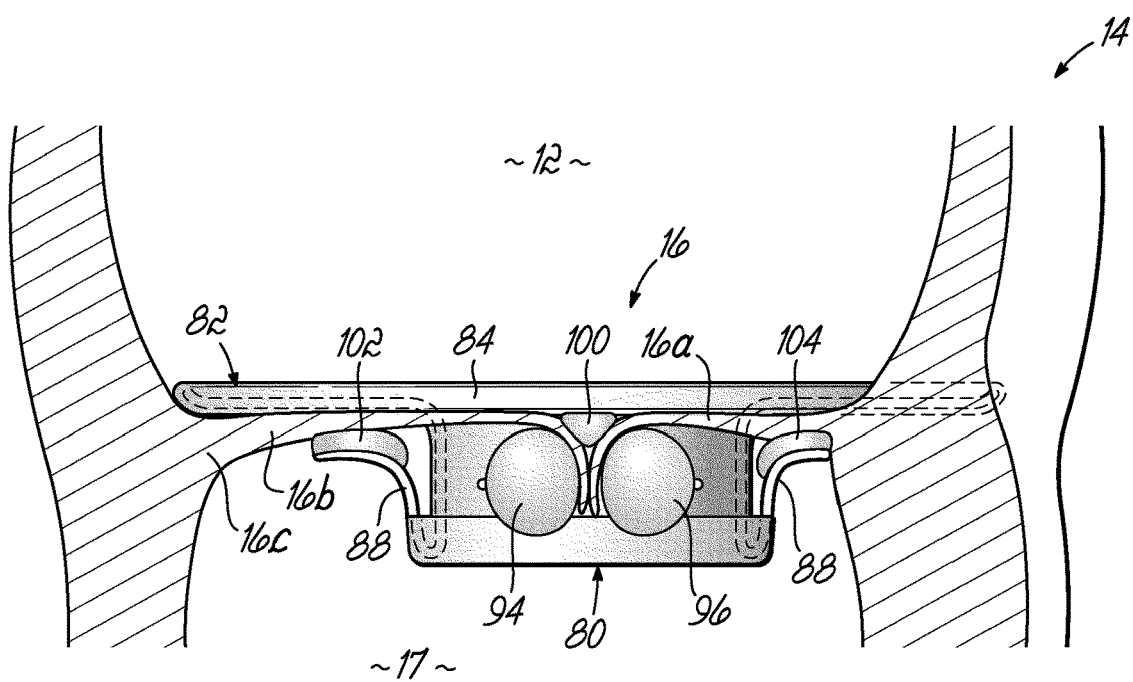
FIG. 8E is a cross sectional view similar to FIG. 8D, but illustrating another embodiment using additional inflatable balloons.

As illustrated in FIG. 8E, it is also possible to have an arrangement of inflatable elements to seal a leak that involves the use of one or more balloons on the atrial and ventricular sides of the annulus. For example, this figure illustrates a third balloon 100 that is located at a higher plane than the previous two sealing balloons 94, 96 that are located below the leaflets at one of the commissures. This increases the trapping of the leaflets 16a, 16b and further guarantees the security of the leak prevention. This third balloon 100 could be larger or smaller, or different in shape, but the key feature is that it can help to trap the leaflets on each side of the native mitral valve 16. This arrangement with sealing balloons 94, 96, 100 above and below the leaflets 16a, 16b also helps to anchor the valve 80. This arrangement would make it difficult for the valve prosthesis 80 to slip out of position and, in fact, it is conceivable that a valve prosthesis 80 could be anchored alone with just fixation at the commissures, such as illustrated. The sealing balloons would ideally be larger to ensure that the valve 80 does not slip for anchoring purposes. FIG. 8E illustrates the three balloons 94, 96, 100 attached to the valve prosthesis 80, however, it will be appreciated that one or more of these balloons may be used separately and independently from the valve prosthesis 80. For example, after a valve prosthesis 80 is implanted a leak may occur and these three balloons may be implanted at a commissure and inflated to seal the leak. The balloons in that case would likely have to be joined together. FIG. 8E further illustrates inflatable elements or balloons 102, 104 attached with the anchoring arms 88 for additional securement and anchoring ability.

Figure 8F:
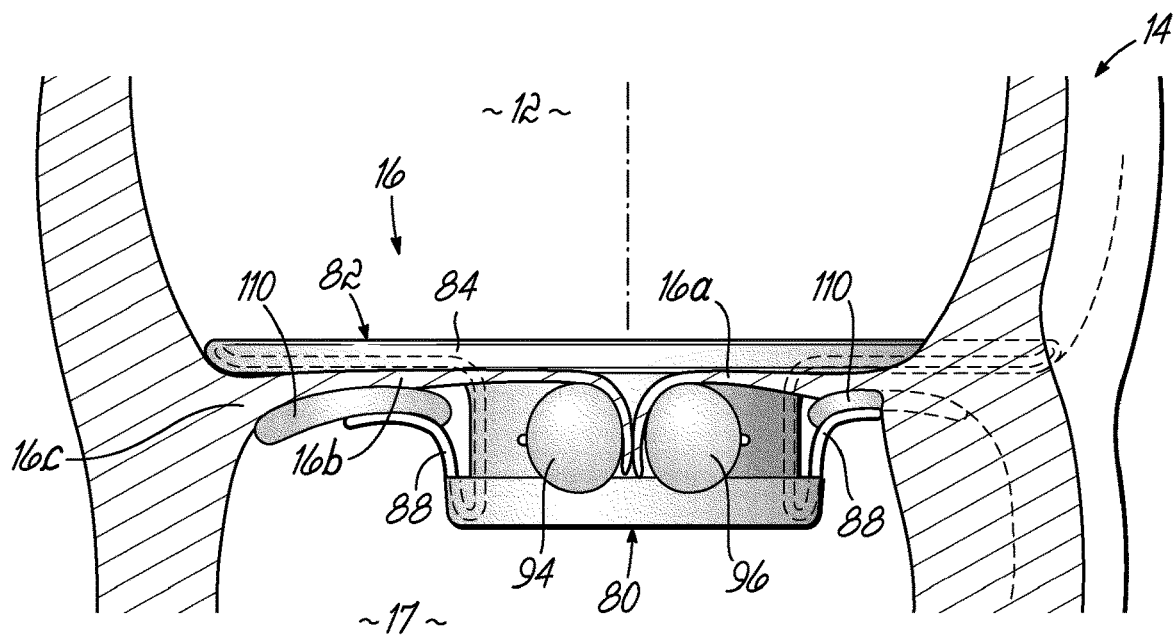
FIGS. 8F and 8G are cross sectional views similar to FIG. 8E, but illustrating embodiments using alternative inflatable balloons.
Figure 8G:
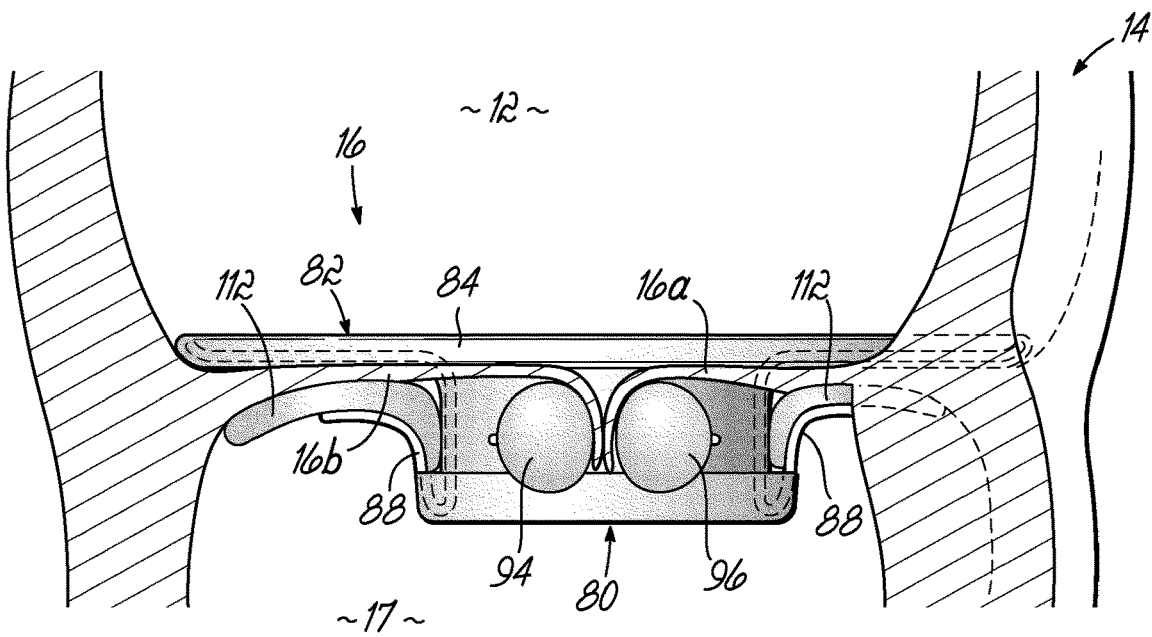

FIGS. 8F and 8G illustrate alternative embodiments with larger sealing and/or anchoring balloons 110, 112 attached to the arms 88 for purposes of even better stabilization of the valve prosthesis 80.

Figure 9A:
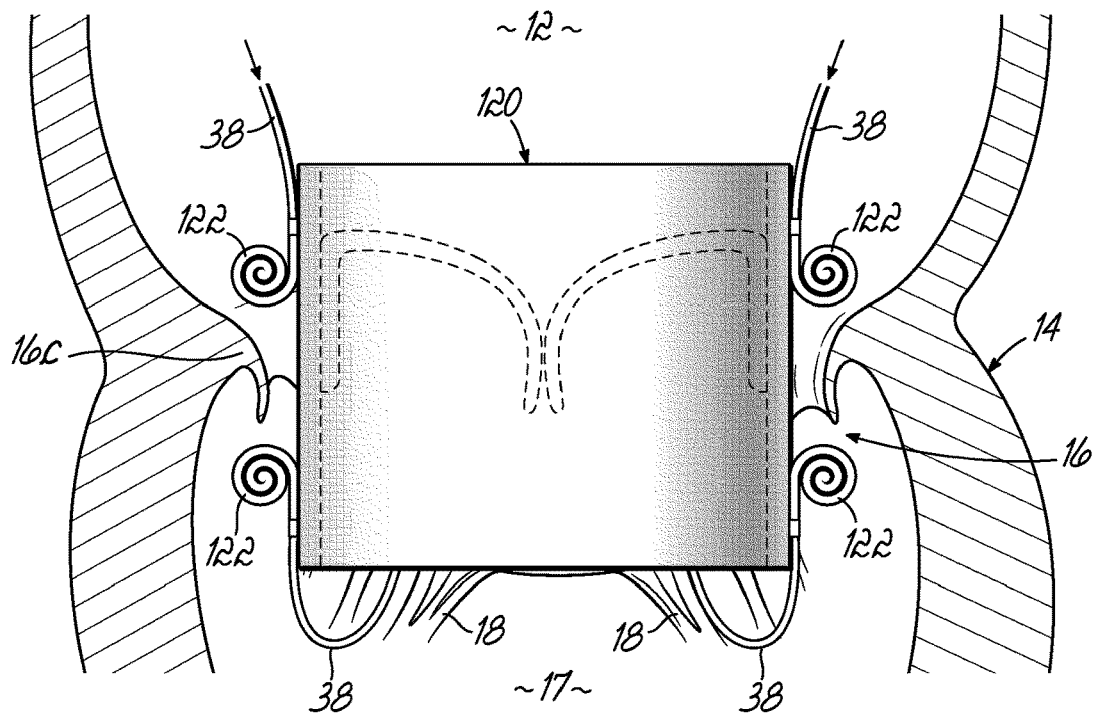
FIG. 9A illustrates a cross sectional view of another embodiment showing a mitral valve prosthesis including inflatable elements for stabilizing and anchoring the position of the mitral valve prosthesis at the location of the native mitral valve.
Figure 9B:
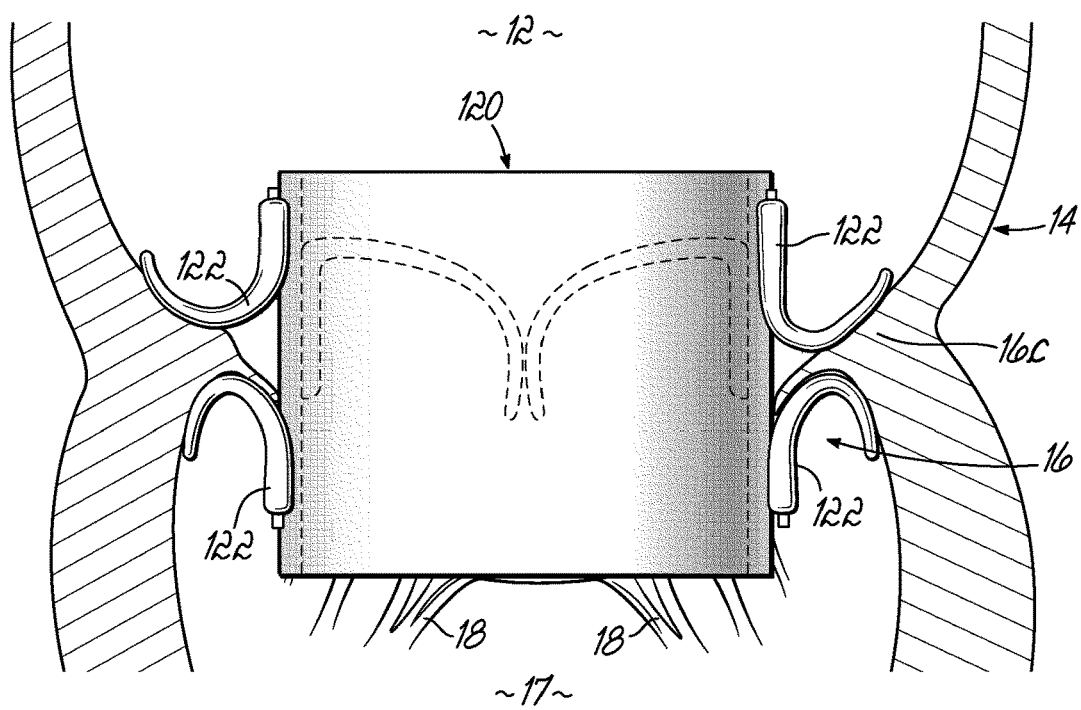
FIG. 9B is a cross sectional view of the native mitral valve location, similar to FIG. 9A, but showing the inflatable elements in their inflated conditions.

FIGS. 9A and 9B illustrate a mitral valve prosthesis 120 having anchoring and/or sealing balloons 122 attached to it and, when inflated, these balloons or inflatable elements 122 extend beyond the valve prosthesis 120. For example, the balloons 122 may be initially in a collapsed condition such as a rolled up condition as shown. This will allow for delivery through a catheter. The balloons 122 are unfurled or extended by injecting fluid or gas into the fluid delivery tubes 38 as shown in FIG. 9A to form the inflatable elements 122 into their expanded and inflated conditions shown in FIG. 9B. In these expanded conditions, the inflatable elements 122 may be used for sealing and/or anchoring purposes. The unfurling or expansion of the inflatable elements 122 moves the balloons into their sealing and/or anchoring positions, as desired. There may be any number of inflatable elements, and the inflatable elements may be used at any position along the valve prosthesis 120. In the example shown, there are four separate balloons 122 or inflatable elements with two located above the native mitral valve annulus 16c and two located below the native mitral valve annulus 16c. It would also be possible to create a circumferential balloon or inflatable element. For example, the two balloons 122 shown above the native mitral valve annulus could be replaced by a balloon that extends circumferentially around the prosthetic valve 120. By extending beyond the margin of the prosthetic valve 120, the inflatable elements 122 are able to take on greater roles in anchoring. The balloons 122 below the native annulus 16c could extend from the commissures and wrap around the valve prosthesis 120 below the native annulus to hold the prosthesis 120 in position.

Figure 10A:
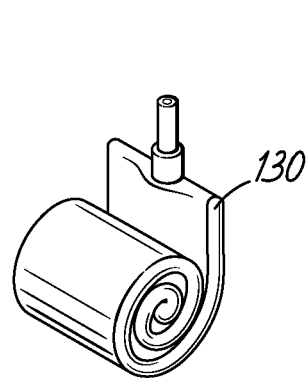
FIGS. 10A-10D are perspective views illustrating various additional embodiments of inflatable elements usable in connection with mitral valve prostheses.
Figure 10B:
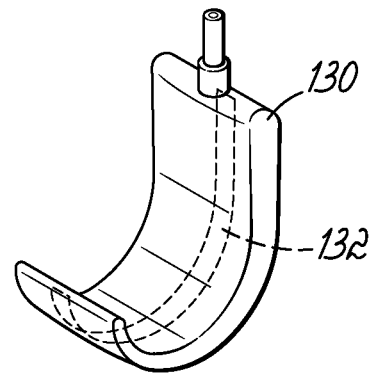
Figure 10C:
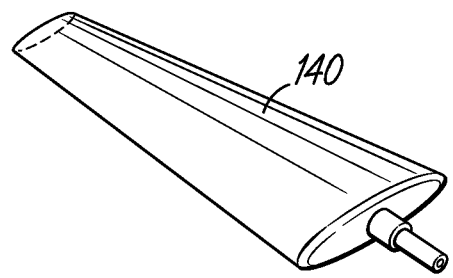
Figure 10D:
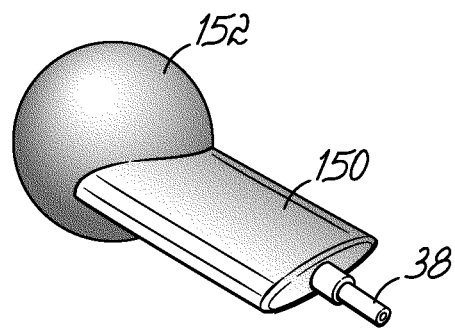

FIGS. 10A and 10B illustrate an inflatable element 130 that is rolled up in a collapsed position (FIG. 10A) and then deployed into an operative position by way of inflation, as previously described. In this embodiment, a superelastic wire 132 is embedded or otherwise affixed to the inflatable element 130 to initially retain the inflatable element 130 in the collapsed condition shown in FIG. 10A. FIG. 10C illustrates another of many possible inflatable element shapes, i.e., a sealing element and/or anchor 140 that extends longitudinally in essentially a linear orientation after inflation. FIG. 10D illustrates yet another possible shape that is more complex. Here, there is a linear inflatable element 150 with an enlarged balloon portion 152 at the distal end.

Figure 11A:
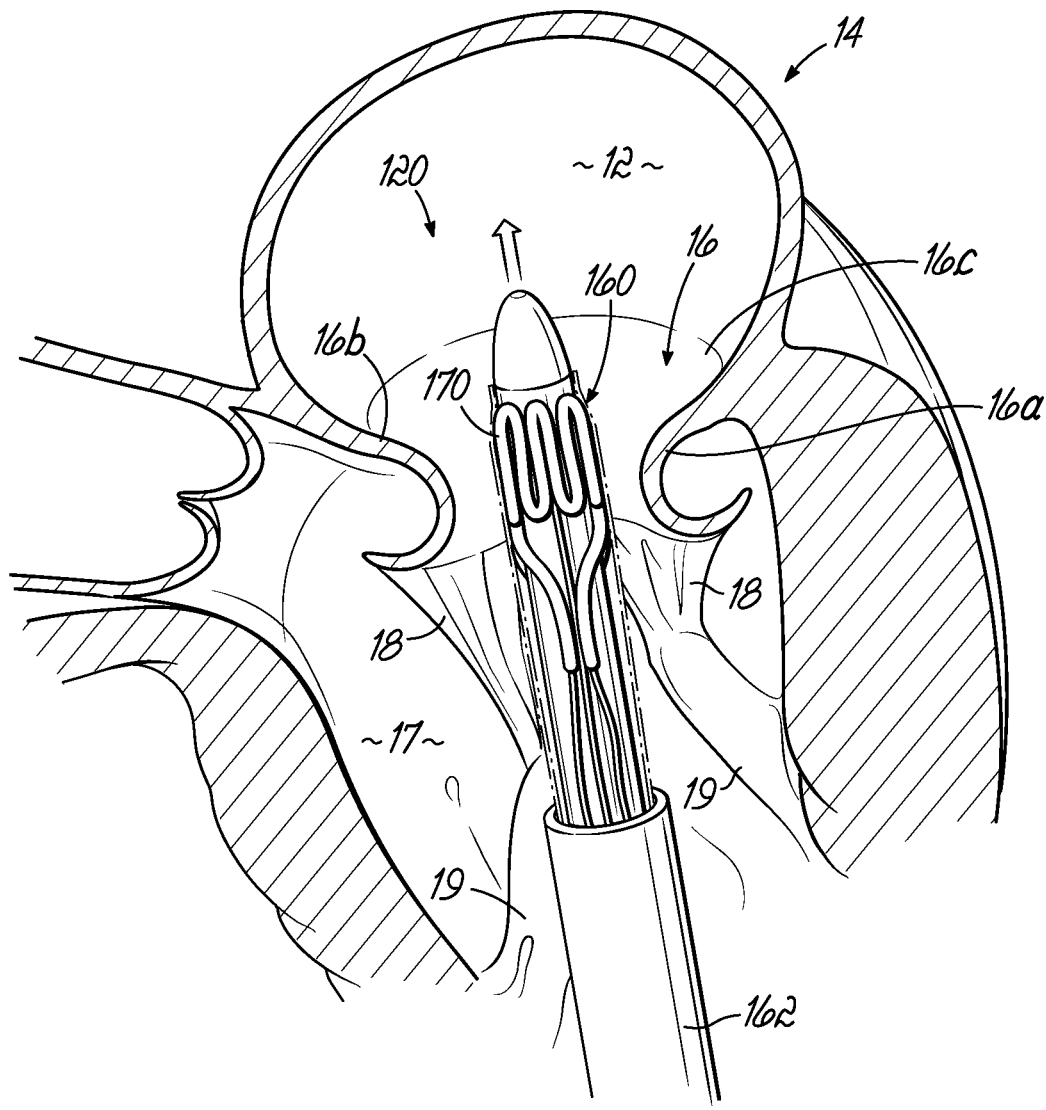
FIG. 11A is a cross sectional view of the native mitral valve location together with a perspective view of a delivery catheter generally showing an approach from below the native mitral valve.
Figure 11B:
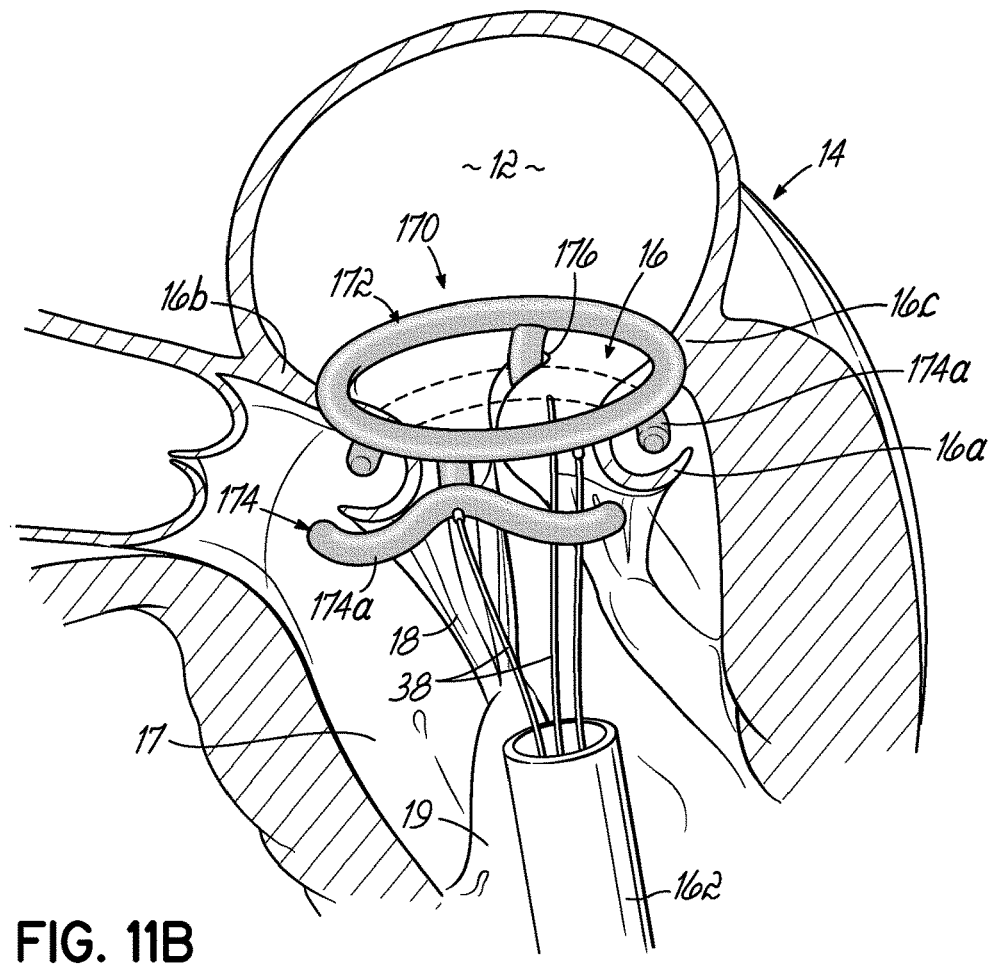
FIG. 11B is a cross sectional view similar to FIG. 11A, but illustrating the delivery of an inflatable anchoring and/or sealing element at the position of the native mitral valve.

FIG. 11A illustrates another method for implantation of a mitral valve prosthesis 160 using catheter technologies. Here, the valve prosthesis 160 is being directed to the location of the native mitral valve 16 through the apex of the heart via a delivery catheter 162. Previous embodiments have shown a valve prosthesis implanted via the left atrium. The procedure in the figures below may also be performed from the left atrium. A valve prosthesis 160 and its implantation or delivery catheter 162 has been advanced from the left ventricle across the native mitral valve 16 and the tip of the system resides in the left atrium. In this embodiment, an inflatable anchoring and/or sealing system 170 is shown including an upper portion 172 for residing above the native mitral valve 16 and a portion 174 below the native mitral valve 16 (FIG. 11B). As shown in FIG. 11B, following deployment, the upper portion 172 includes a circular or continuous annular inflatable element, while the lower portion 174 includes a discontinuous inflatable structure. In other words, the lower portion includes discrete inflatable elements 174a separated from one another, such as by gaps. It will be appreciated that the upper portion 172 could likewise include discrete inflatable elements and, therefore, be a discontinuous inflatable structure as opposed to the continuous inflatable element as shown by way of example. Also, FIG. 11B illustrates the inflatable structure coupled to inflation tubes or catheters 38 and does not show the valve prosthesis 160 for clarity. It will be appreciated that the inflatable structure 170 may be coupled to the valve prosthesis 160 during delivery, or the inflatable structure 170 may be delivered first and then the valve prosthesis 160 delivered subsequently to a location within the inflatable structure 170 and expanded as previously described thereby using the inflatable structure 170 for anchoring and/or sealing. The inflatable elements 174a that are located below the native mitral valve 16 are introduced at each of the commissures and have extensions that lie under the anterior and posterior leaflets 16a, 16b. The upper portion 172 and the lower portions 174a are connected together at and through the commissure locations 176. The previous series of figures illustrate how the anchors and/or sealing balloons may be delivered in a closed or collapsed configuration and then expanded outward to achieve a configuration such as the configuration shown in FIG. 11B.

Figure 11C:
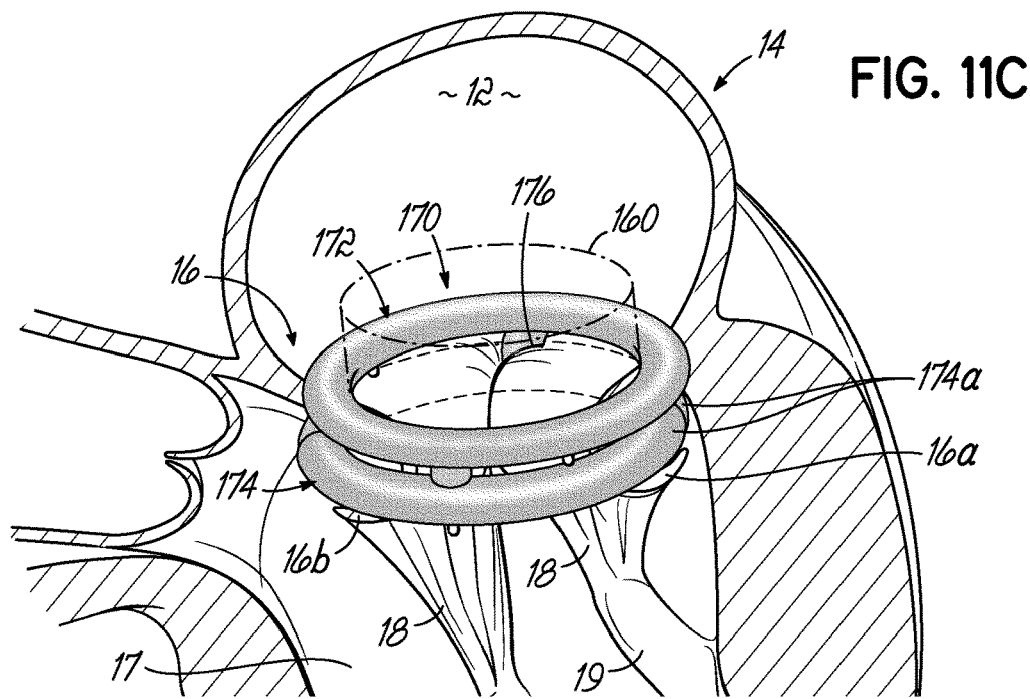
FIG. 11C is a cross sectional view similar to FIG. 11B, but illustrating an alternative embodiment of an inflatable element used for anchoring and/or sealing a mitral valve prosthesis.

FIG. 11C illustrates the valve prosthesis 160 in dash-dot lines but has been positioned inside the inflatable docking/ anchoring system 170. This valve prosthesis 160 will be very securely implanted since it is supported by upper and lower inflatable anchoring portions 172, 174 including ring/annular shaped and/or semi-ring shaped elements that reside on each side of the native mitral valve 16. The leaflets 16a, 16b are trapped or engaged between the inflatable elements 174a and this creates a very secure attachment. The upper ring 172 is continuous and closed in this example, while the lower inflatable elements 174a consist of essentially two semi-annular inflatable elements that are not directly attached to one another. It is important to note that the inflatable elements may be pre-attached to a valve prosthesis. This would allow for a one step procedure of delivering the valve prosthesis 160 and its anchoring and/or sealing components 172, 174. It is notable that this may require less material than is currently used with solid anchoring systems such as those formed from metallic materials. Inflatable elements that more fully surround the valve prosthesis can provide for better anchoring than the discrete balloons shown in previous embodiments on opposite sides of a valve prosthesis. It will also be appreciated that the valve prosthesis may be suitably anchored and sealed using the sealing balloons as previously described at the commissure locations and using additional inflatable element or elements below the native mitral valve annulus 16c, such as those shown in FIG. 11B or 11C. FIG. 11C illustrates full inflation of the structure shown in FIG. 11B and a valve prosthesis 160, in dash-dot lines, expanded within the inflatable sealing/anchoring system 170.

Figure 11D:
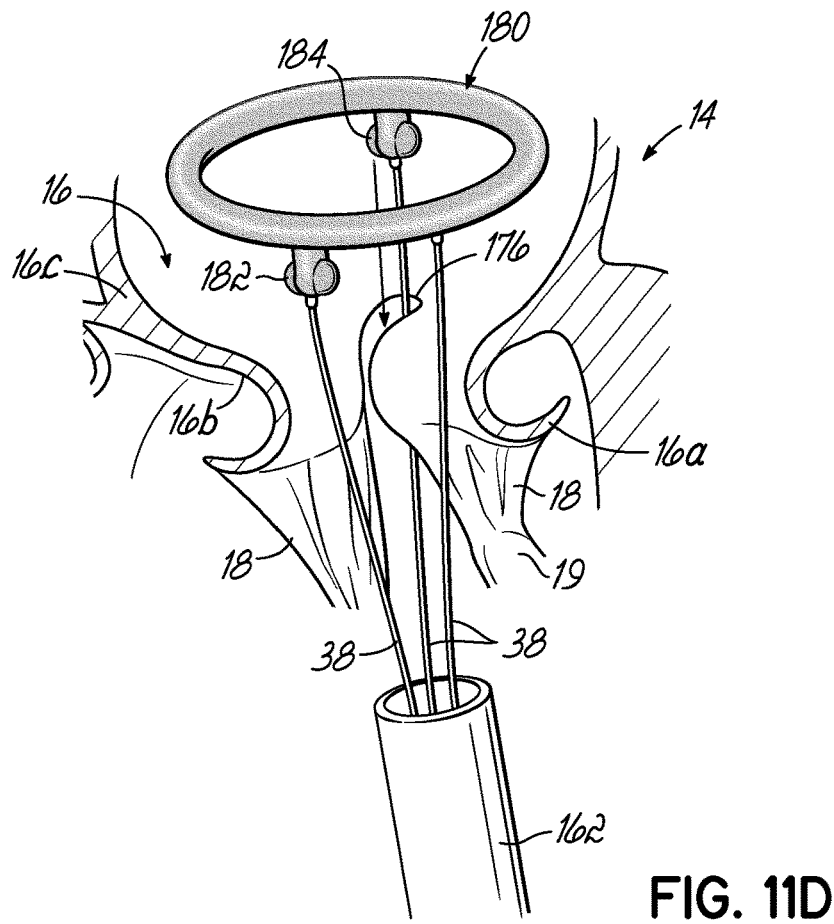
FIG. 11D is a cross sectional view similar to FIGS. 11B and 11C, but illustrating another embodiment of an inflatable element for anchoring and/or sealing a mitral valve prosthesis with respect to the native mitral valve.
Figure 11E:
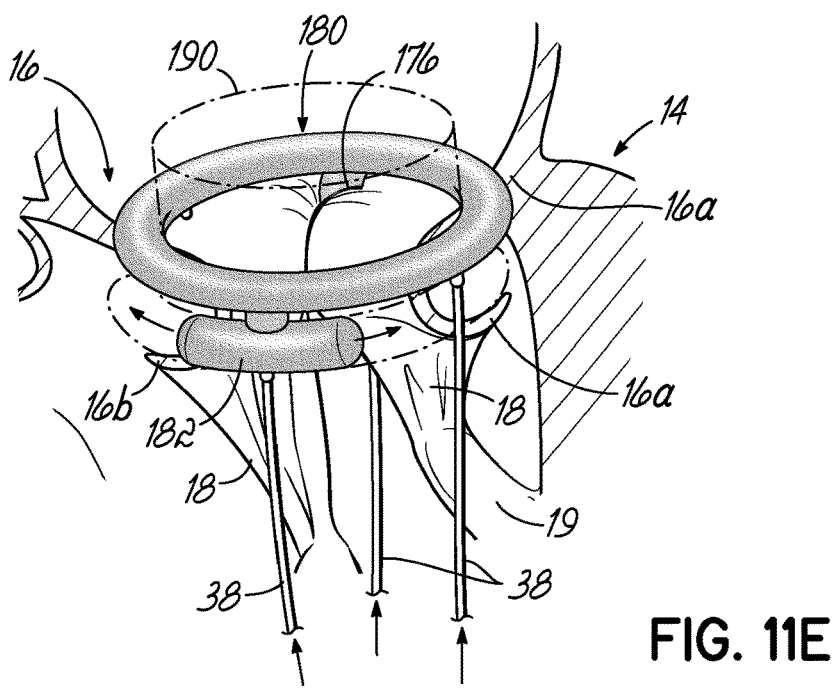
FIG. 11E is a cross sectional view similar to FIG. 11D, but illustrating a further step in the delivery method for inflating the inflatable element, including the portion delivered below the native mitral valve.
Figure 11F:
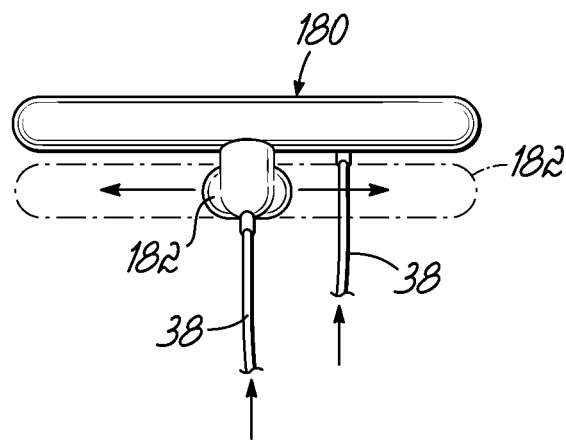
FIGS. 11F and 11G are respective side views of the inflatable element shown in FIGS. 11D and 11E, and respectively showing the inflation and deployment process for the lower, discontinuous portion of the inflatable element configured to be deployed below the native mitral valve leaflets.
Figure 11G:
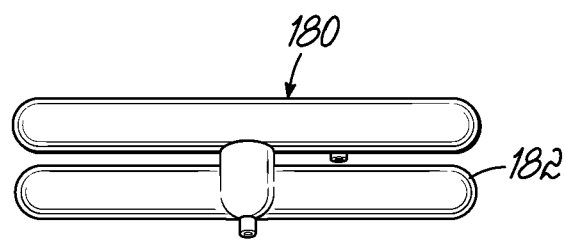

FIGS. 11D through 11G illustrate another alternative embodiment for deploying one or more balloon elements. In this regard, balloon elements 182, 184 are shown on the lower portion of the inflatable structure 180 for purposes of being implanted below the native mitral valve 16. In this implantation position, in which the lower portion of the inflatable structure 180 has been inserted through the native mitral valve 16 at the commissure locations 176 as shown in FIG. 11D, the lower inflatable elements 182, 184 are then deployed from their respective collapsed conditions (FIG. 11D) to expanded positions in which they are directed beneath the respective anterior and posterior native mitral leaflets 16a, 16b. As will be described below, these inflatable portions 182, 184 may have tapered distal end shapes and even include integrated guidewire systems for purposes of assisting the guidance of the inflatable element past the chordae tendinae 18 and beneath the native leaflets 16a, 16b. The deployment process is shown in FIG. 11E and FIG. 11F and the full deployment is shown in FIG. 11G. As further shown in FIG. 11E, the expandable mitral valve prosthesis 190 is then deployed within the annular space of the inflatable anchoring/sealing system 180 and the valve prosthesis 190 is firmly anchored into position. As another alternative, the inflatable anchoring/sealing system 180 may be preattached to the valve prosthesis 190 and the entire assembly may be implanted through a single delivery catheter system.

Figure 12A:
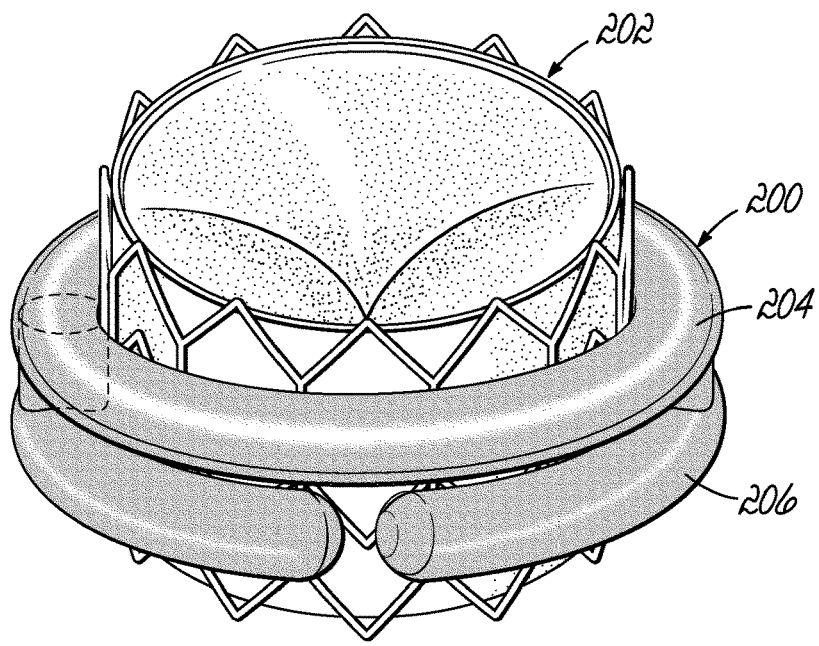
FIG. 12A is a perspective view illustrating an expansible stent valve, used as a mitral valve prosthesis, in combination with the inflatable element such as shown in FIGS. 11D through 11G.
Figure 12B:
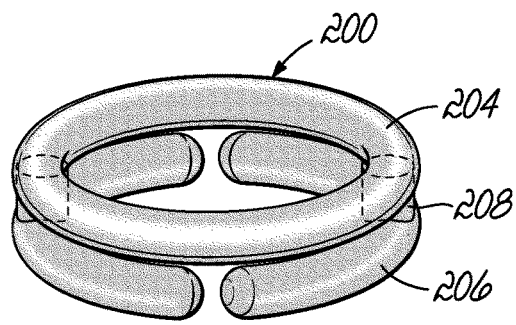
FIG. 12B is a perspective view illustrating the inflatable element of FIG. 12A in isolation.

FIG. 12A illustrates an inflatable prosthetic valve anchoring/sealing system 200 with a mitral valve prosthesis 202 within the system. The native mitral valve leaflets are not shown. An upper inflatable ring 204 is closed and continuous, while the lower inflatable ring 206 has two gaps, one under the anterior leaflet and one under the posterior leaflet. The upper and lower inflatable elements or rings 204, 206 trap the native mitral leaflets and provide a very secure anchoring for the prosthesis 202. If the inflatable system 200 is preattached to the valve prosthesis 202, it would not be necessary to configure the upper and lower inflatable elements 204, 206 as completely or near completely circumferential. Instead, the inflatable elements may be attached around the perimeter of the valve prosthesis in discrete inflatable segments and without forming a complete or even a near complete circle around the prosthesis. FIG. 12B illustrates the inflatable structure of FIG. 12A in more complete form. It will be appreciated that the connecting portions in dotted lines in FIG. 12B pass through the commissures and join the upper and lower inflatable elements of the structure. It will also be appreciated that one or more inflatable elements may be used in combination with a mechanical anchoring structure instead of with other inflatable structure.

Figure 12C:
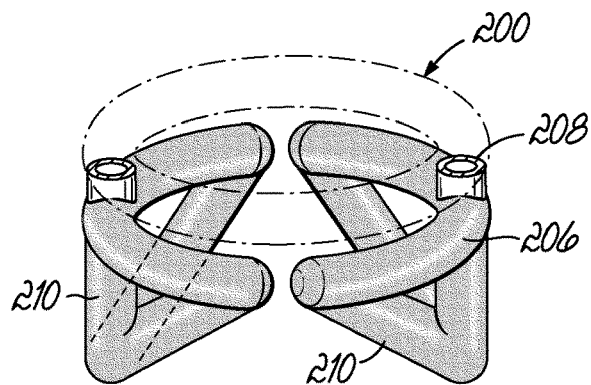
FIG. 12C is a perspective view showing another embodiment of an inflatable element including reinforcement structure for supporting the lower, discontinuous portion of the inflatable or balloon element.

FIG. 12C illustrates another alternative embodiment in which reinforcement structure 210 is added to the lower inflatable elements. This reinforcement structure 210 comprises additional inflatable elements for purposes of providing additional strength to anchor the inflatable elements beneath the mitral valve annulus. The portion of the inflatable elements 206 closest to the connector portion 208 with the upper inflatable element 204 will quite stable. However, the portions extending therefrom and especially the free ends 206a will not be as stable. Therefore, to increase the stability of the lower anchor/sealing portions 206, under the native mitral valve leaflets, a suitable reinforcement structure is or may be desirable. The two ends of each of the lower inflatable elements 206 continue downward into the left ventricle in a triangular arrangement that increases their stability and their ability to compress against the upper inflatable element. Other reinforcement structures may also be used instead or in addition to this structure.

Figure 12D:
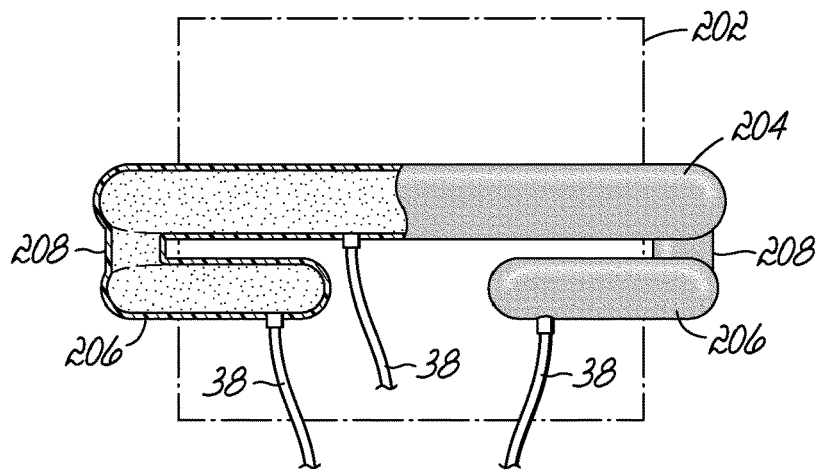
FIG. 12D is a partially fragmented side elevational view of the balloon inflatable element of FIGS. 12A and 12B, showing inflation inputs and fluid in the form of a material that can solidify.

FIG. 12D illustrates a partial cross section of the structure shown in FIG. 12B, to illustrate the outer shell of the inflatable element, which may be comprised of a suitable polymer for implant purposes, and the interior being filled with a hardenable fluid, as previously described. This figure also shows catheters or fluid delivery tubes 38 which allow entry and removal of the fluid. These catheters 38 can vary in their attachment site to the inflatable element and in their number. As previously described, these fluid delivery catheters or tubes 38 may be attached with a screw mechanism. A valve may be placed inside the balloon to retain the fluid or polymeric resin at the site of the removal of the catheter. The fluid delivery catheter 38 could frustrate the valve when it is in place. Other systems have described removing catheters or fluid delivery tubes and making a heat seal in a polymer to seal the exit or outlet site.

Figure 12E:
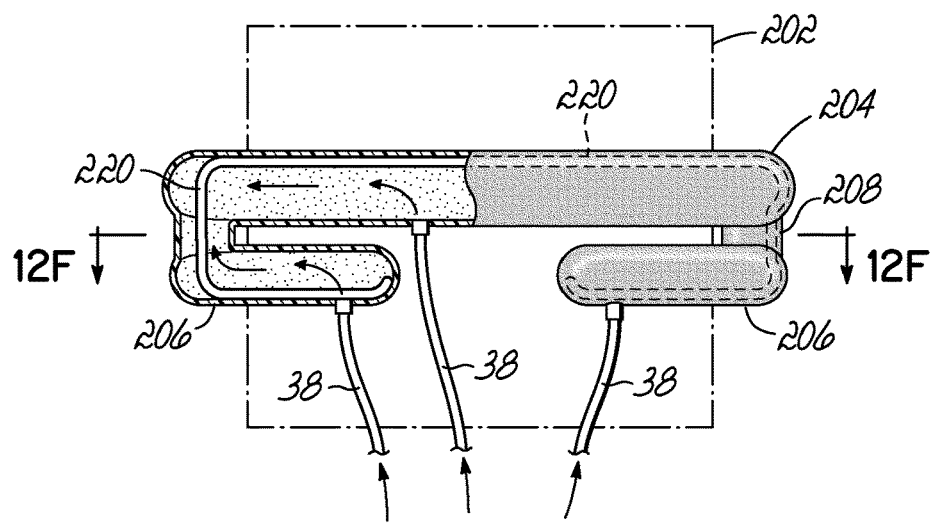
FIG. 12E is a partially fragmented, side elevational view similar to FIG. 12D, but illustrating another embodiment of the inflatable element including reinforcing structure in the form of a wire frame.
Figure 12F:
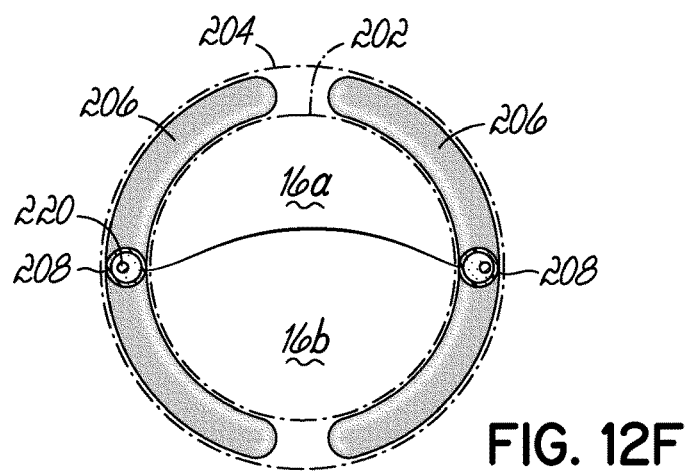
FIG. 12F is a top view showing the placement and orientation of the lower, discontinuous portion of the inflatable element relative to the native mitral valve.

FIG. 12E illustrates that the inflatable structure may have additional support or reinforcement in the form of a frame or wire 220, as shown. The wire may be superelastic, such as a Nitinol wire or other shape memory material, may be added to the structure within or otherwise as a part of the inflatable element. The wire or other reinforcement structure may extend beyond the end of the balloon for those lower portions that will need to be directed in a more accurate manner, such as described further below. FIG. 12F is a view from below the inflatable structure shown in FIGS. 12D and 12E.

Figure 12G:
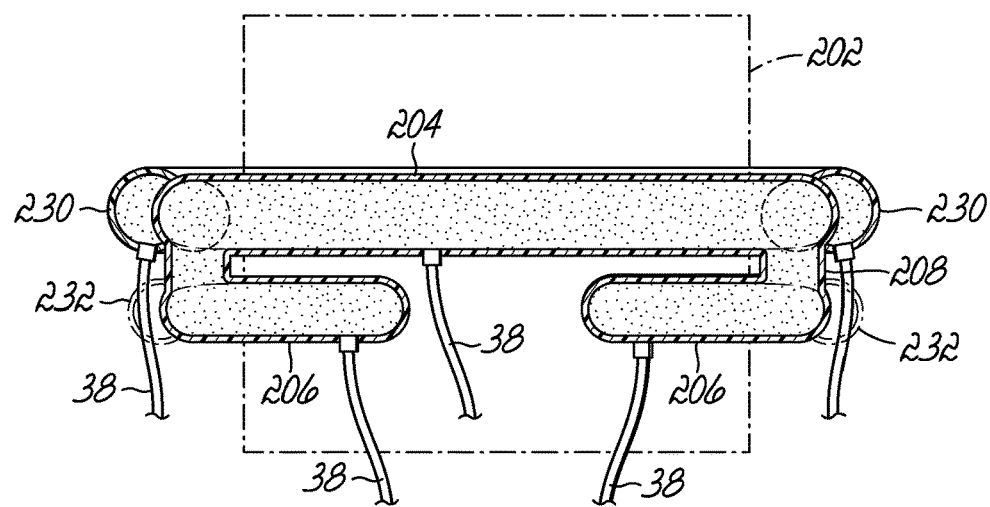
FIG. 12G is a side cross sectional view of an inflatable element configured in accordance with another embodiment.

FIG. 12G illustrates another alternative embodiment similar to FIG. 12D, however, the upper inflatable portion includes an additional outer balloon element 230 to tighten the fit and/or increase the anchoring ability especially for accommodating anatomy and/or valve prostheses of differing sizes. In a similar manner, an outer balloon or inflatable element 232 may be added to the lower inflatable portion, as shown. It will be appreciated that discrete balloon or inflatable elements may be added at various locations around the circumference of the structure. This may be a desirable alternative for allowing the use of a smaller sized valve prosthesis in a larger sized natural or native mitral valve annulus. For accommodating a smaller valve, additional inflatable rings may be inflated or the rings may be inflated with additional hardenable fluid.

Figure 12H:
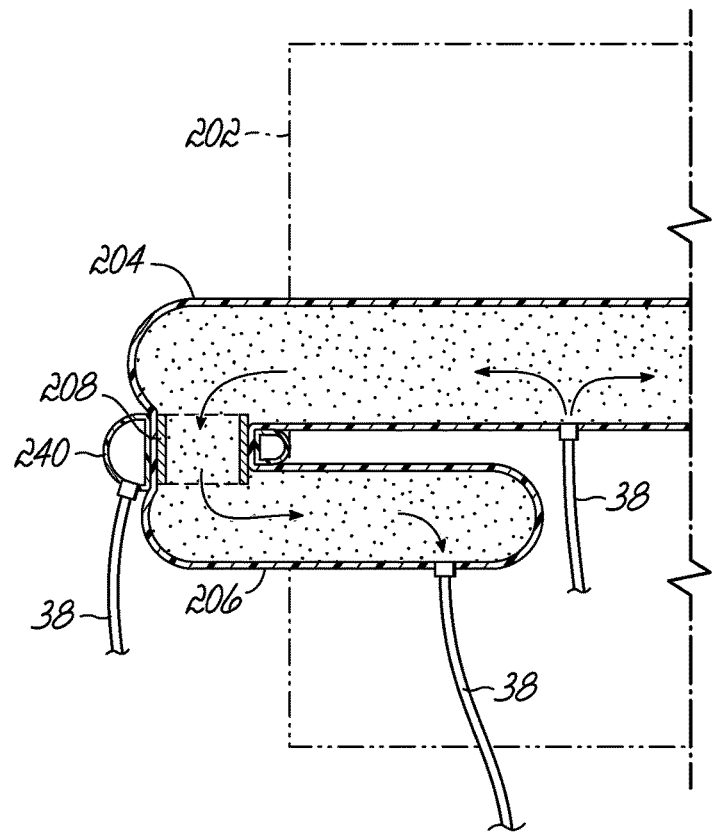
FIG. 12H is an enlarged cross sectional view of the inflatable element similar to FIG. 12C, but showing the use of further sealing balloons.

FIG. 12H illustrates another alternative embodiment to the structure shown in FIG. 12G. In this embodiment, additional inflatable elements or balloons 240 may be placed at the positions of the posts or connecting portions for sealing purposes at the commissure locations. These inflatable elements may be separate elements, as shown, or integrated and inflated with one or more of the other balloons.

Figure 13A:
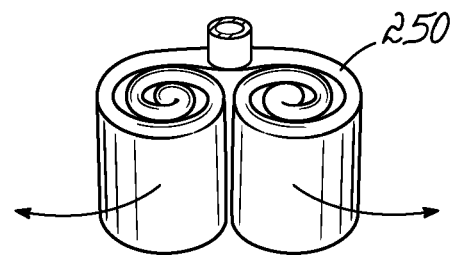
FIGS. 13A-13E are perspective views showing alternative embodiments of inflatable elements used for sealing and/or anchoring mitral valve prosthesis in accordance with the invention.
Figure 13B:
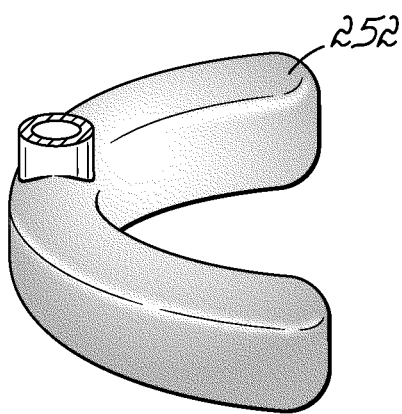
Figure 13C:
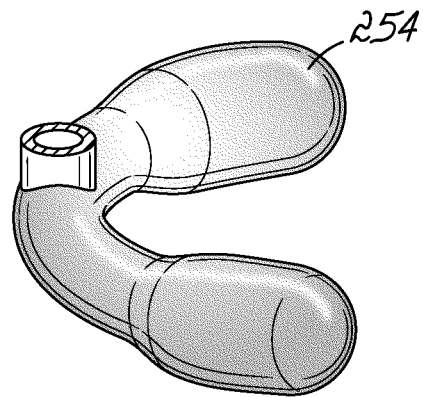
Figure 13D:
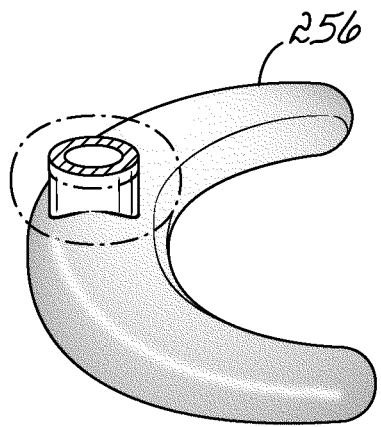
Figure 13E:
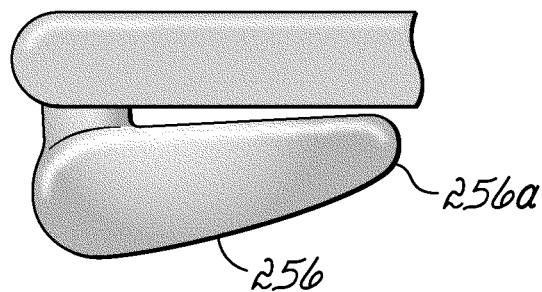

FIGS. 13A through 13E illustrate further alternative embodiments for inflatable elements used for sealing and/or anchoring purposes, especially at locations beneath the native mitral valve. As previously discussed, the inflatable elements may be delivered in a collapsed condition, and this collapsed condition may be a rolled up condition as shown with the element 250 in FIG. 13A or any other suitable, collapsed condition. FIGS. 13B through 13E illustrate various semi-annular shapes 252, 254, 256 that may be used for the lower inflatable elements beneath the native anterior and posterior mitral leaflets. The embodiments shown in FIGS. 13D and 13E are preferred being that the distal ends 256a are tapered in shape to allow for better and more accurate direction of the balloon element past the chordae tendinae (see, e.g. FIGS. 11A through 11E) and beneath the native leaflets.

Figure 14A:
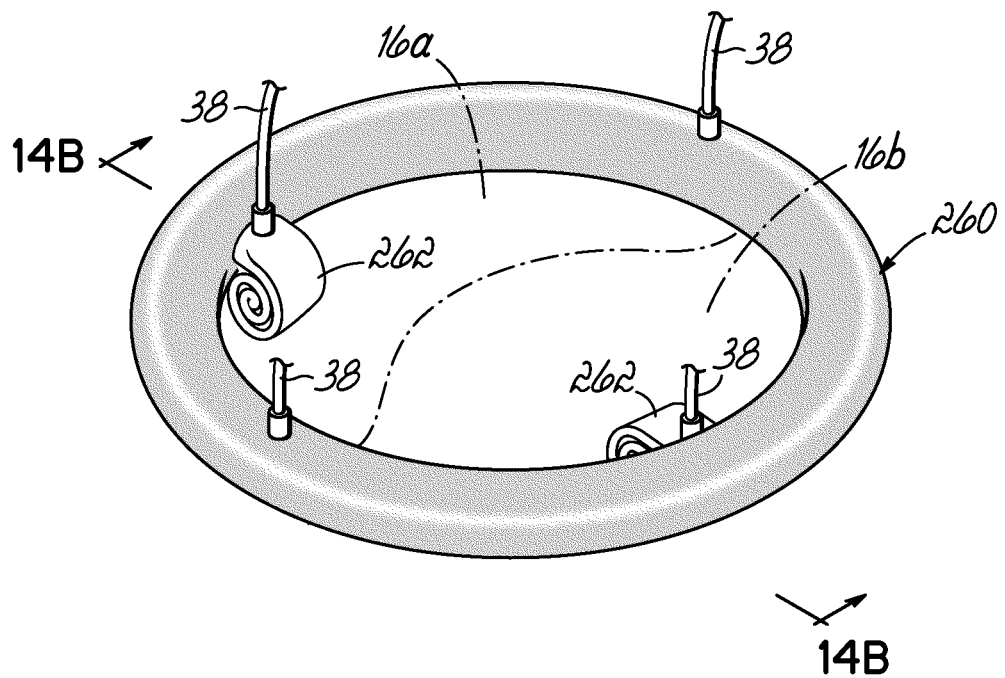
FIG. 14A is a perspective view showing another alternative embodiment of an inflatable element used for anchoring and/or sealing a mitral valve prosthesis.
Figure 14B:
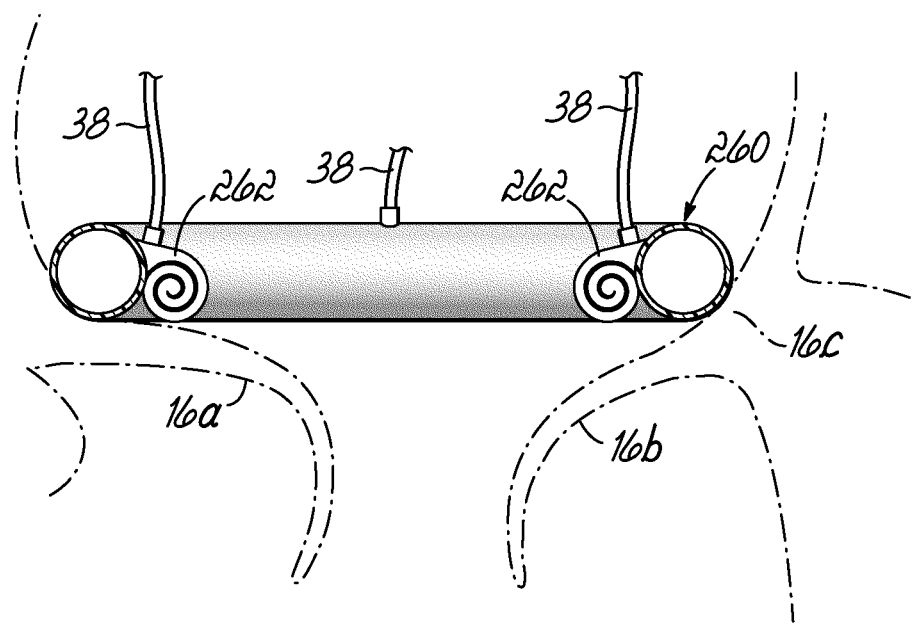
FIG. 14B is a cross sectional view showing the native mitral valve in dash-dot lines and an initial delivery and deployment of the inflatable element shown in FIG. 14A, generally taken along line 14B-14B.
Figure 14C:
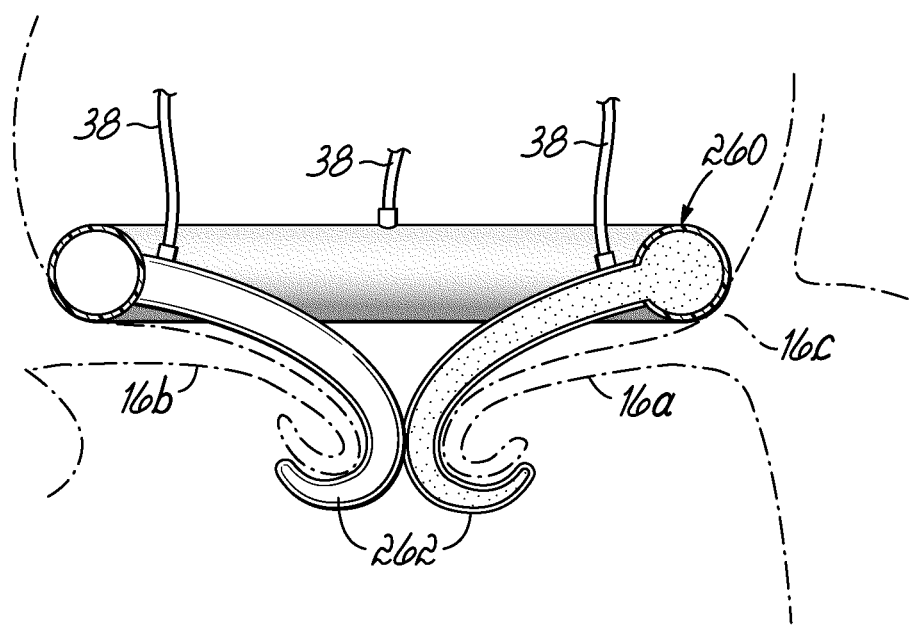
FIG. 14C is a cross sectional view similar to FIG. 14B, but showing deployment of inflatable leaflet capturing elements or extensions.
Figure 14D:
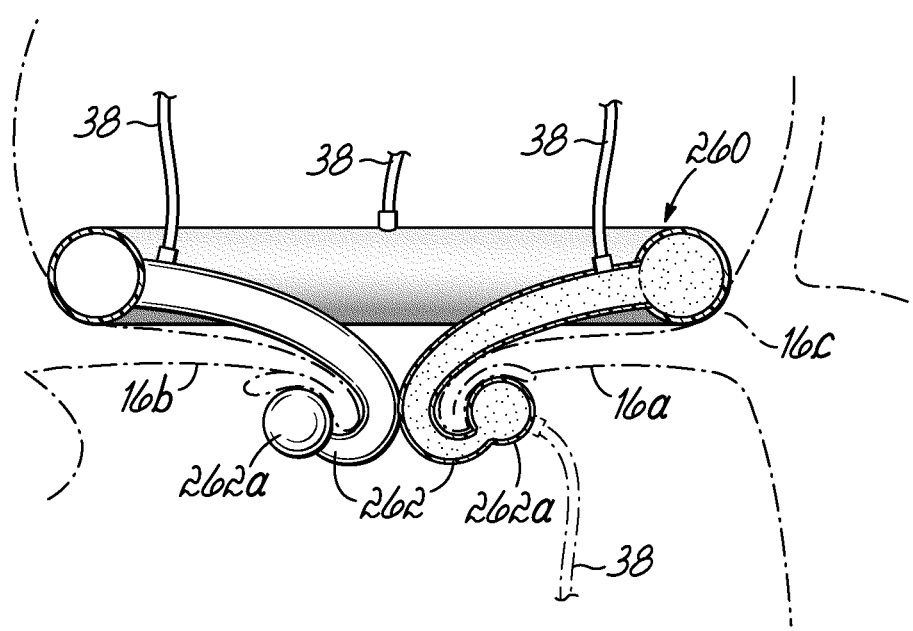
FIG. 14D is a cross sectional view similar to FIG. 14C, but illustrating an alternative embodiment for the leaflet capturing elements or arms.
Figure 14E:
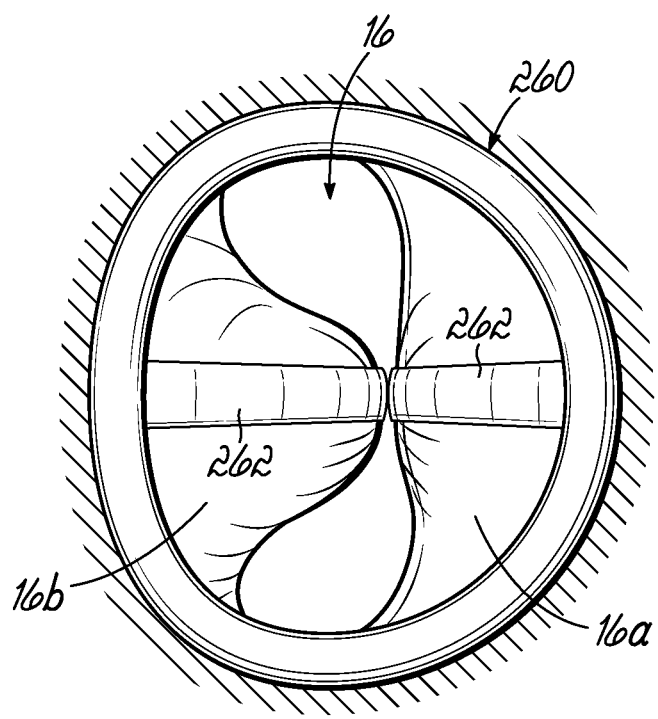
FIG. 14E is a top view of FIGS. 14C and 14D.

FIGS. 14A through 14E illustrate additional embodiments for inflatable elements. In this embodiment, the upper inflatable element 260 is again a complete, continuous annular element, but includes two inflatable extension elements 262 that are initially in a collapsed condition, such as a coiled condition as shown in FIGS. 14A and 14B. When inflated, these inflatable extension portions 262 wrap around the anterior and posterior native mitral leaflets 16a, 16b as shown in FIG. 14C. FIG. 14D illustrates another alternative embodiment in which the distal ends 262a of these inflatable extension elements 262 have bulbous portions for increased leaflet retention purposes. FIG. 14E illustrates the inflated condition as viewed from above. The mitral valve prosthesis (not shown) is directed and deployed within the continuous, annular inflatable element and then expands the inflated extension elements also with the native mitral leaflets radially outward generally in a manner as previously shown and discussed herein.

FIGS. 15A and 15B illustrate an embodiment similar to FIGS. 13D and 13E, however, a guidewire is used for more accurately directing the inflatable element 270 during delivery. In this regard, the wire 272 may be a superelastic or other shape memory material, such as Nitinol. The balloon 270 preferably covers the entire wire or frame, however, a portion 272a of the wire 272 preferably extends from the distal ends of the inflatable element 270 to assist with guiding the distal ends of the inflatable element 270 into place beneath the native mitral valve leaflets (not shown). The guidewire 272 may be fixed to the inflatable element 270 such that no sliding movement is possible between the wire and the inflatable element, or the wire may be used as a guide within, for example, a channel as discussed below.

FIGS. 16A and 16B illustrate another embodiment similar to FIGS. 15A and 15B, however, the distal end or ends 272a of the wire 272 are encapsulated within the shell of the inflatable element 270. Again, the inflatable element 270 is filled with a hardenable fluid, such as a suitable resin material as it known in the art.

Figure 16C:
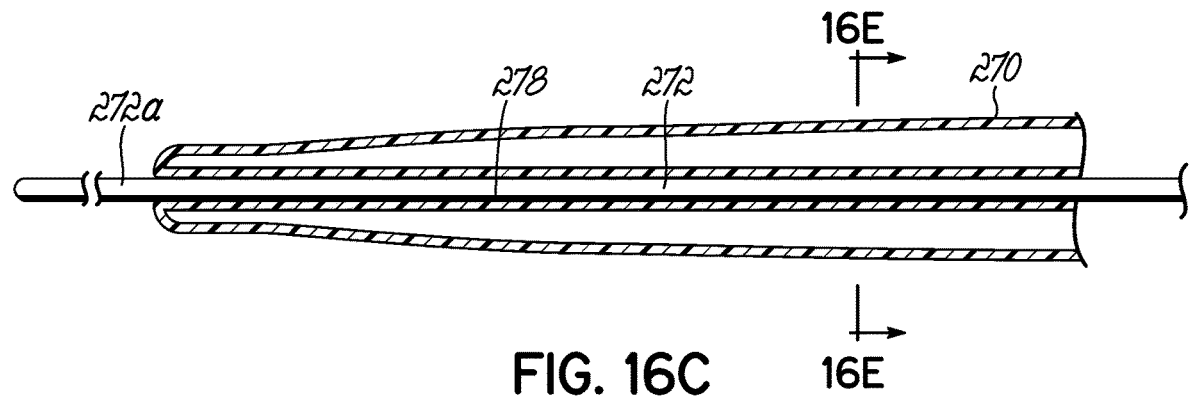
FIG. 16C is a cross sectional view showing an enlarged portion of the inflatable element and guidewire similar to that shown in FIGS. 15A and 15B, with the inflatable element in its uninflated condition.
Figure 16D:
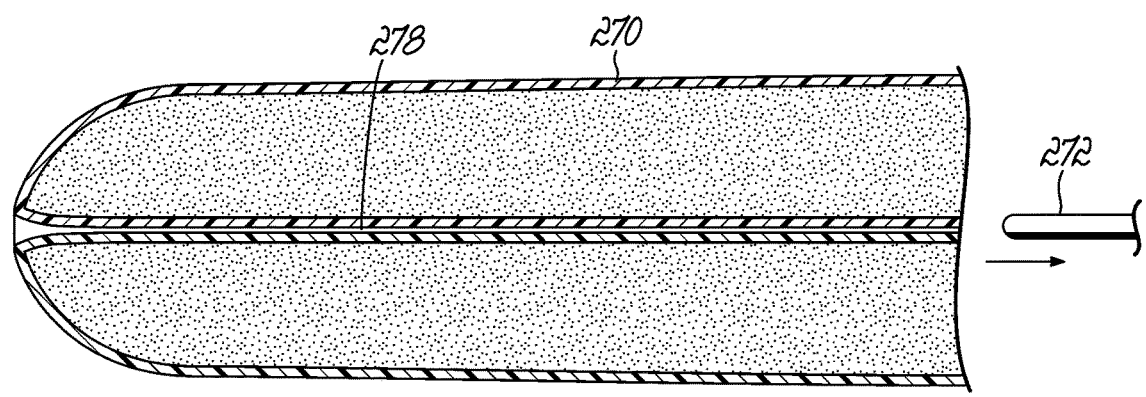
FIG. 16D is an enlarged cross sectional view similar to FIG. 16C, but illustrating the inflatable element in its inflated condition and withdrawal of the guidewire.
Figure 16E:
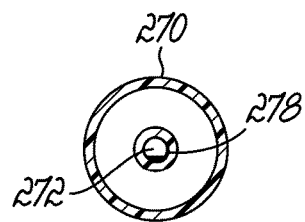
FIG. 16E is a cross sectional view generally taken along line 16E-16E of FIG. 16C.

FIGS. 16C through 16E illustrate another embodiment in which the guidewire 272 is contained within a channel 278 to allow sliding movement between the guidewire 272 and the inflatable element 270 as the inflatable element is directed into place, for example, beneath the mitral valve leaflets of the native mitral valve (not shown).

Figure 17A:
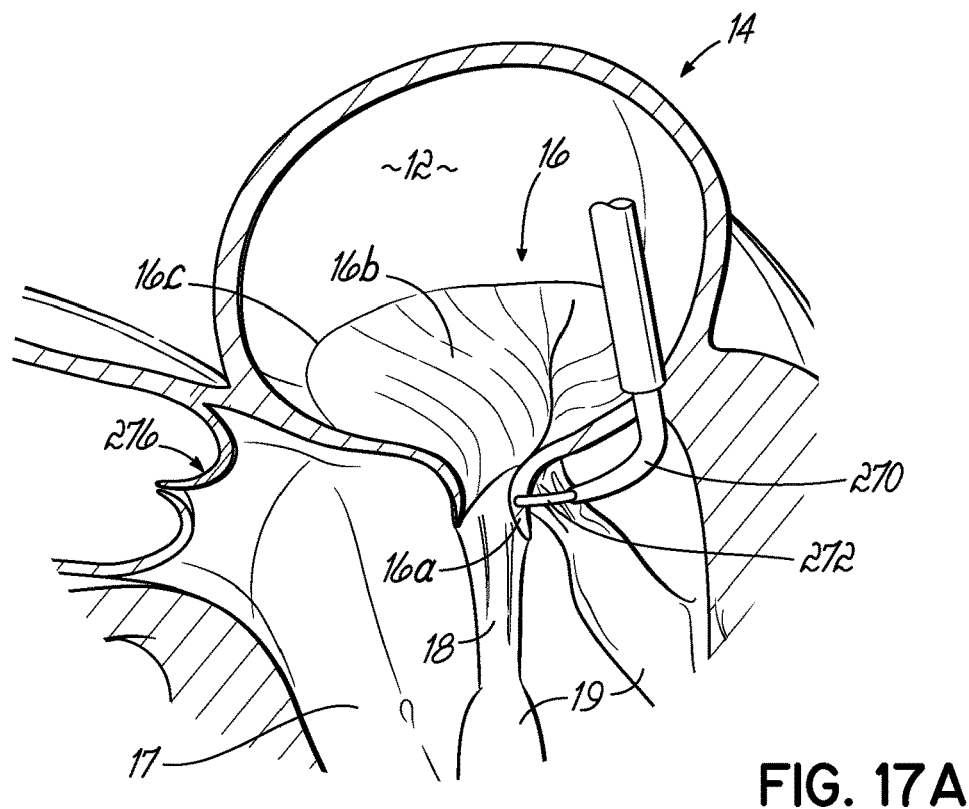
FIGS. 17A and 17B are respective cross sectional views of the native mitral valve showing deployment of an inflatable anchoring and/or sealing element below the leaflets of the native mitral valve.
Figure 17B:
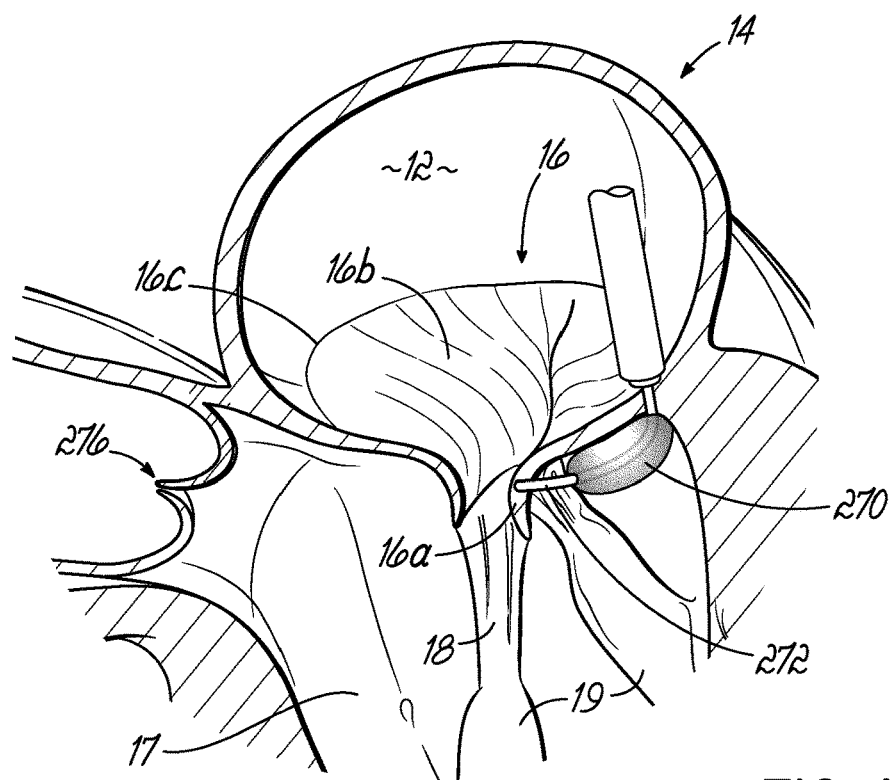

FIGS. 17A and 17B illustrate one example of an inflatable element 270 being directed beneath the native mitral valve leaflets 16a, 16b using a guidewire 272, either rigidly affixed with the inflatable element 270 or slidable with respect to the inflatable element 270. these figures also illustrate the aortic valve 276.

Figure 18A:
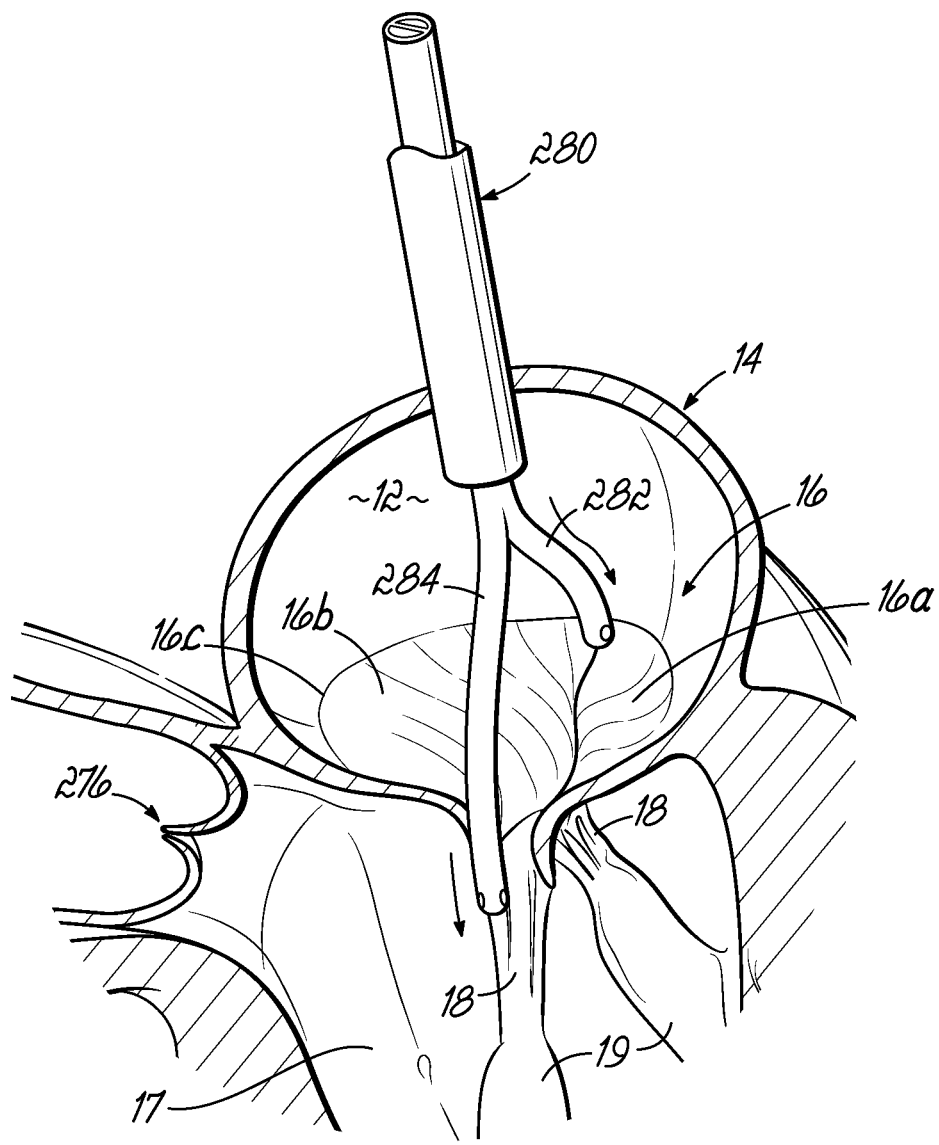
FIGS. 18A-18C are cross sectional views of the native mitral valve showing another method for deploying one or more inflatable elements below the native mitral valve, including initial introduction of guidewires.
Figure 18B:
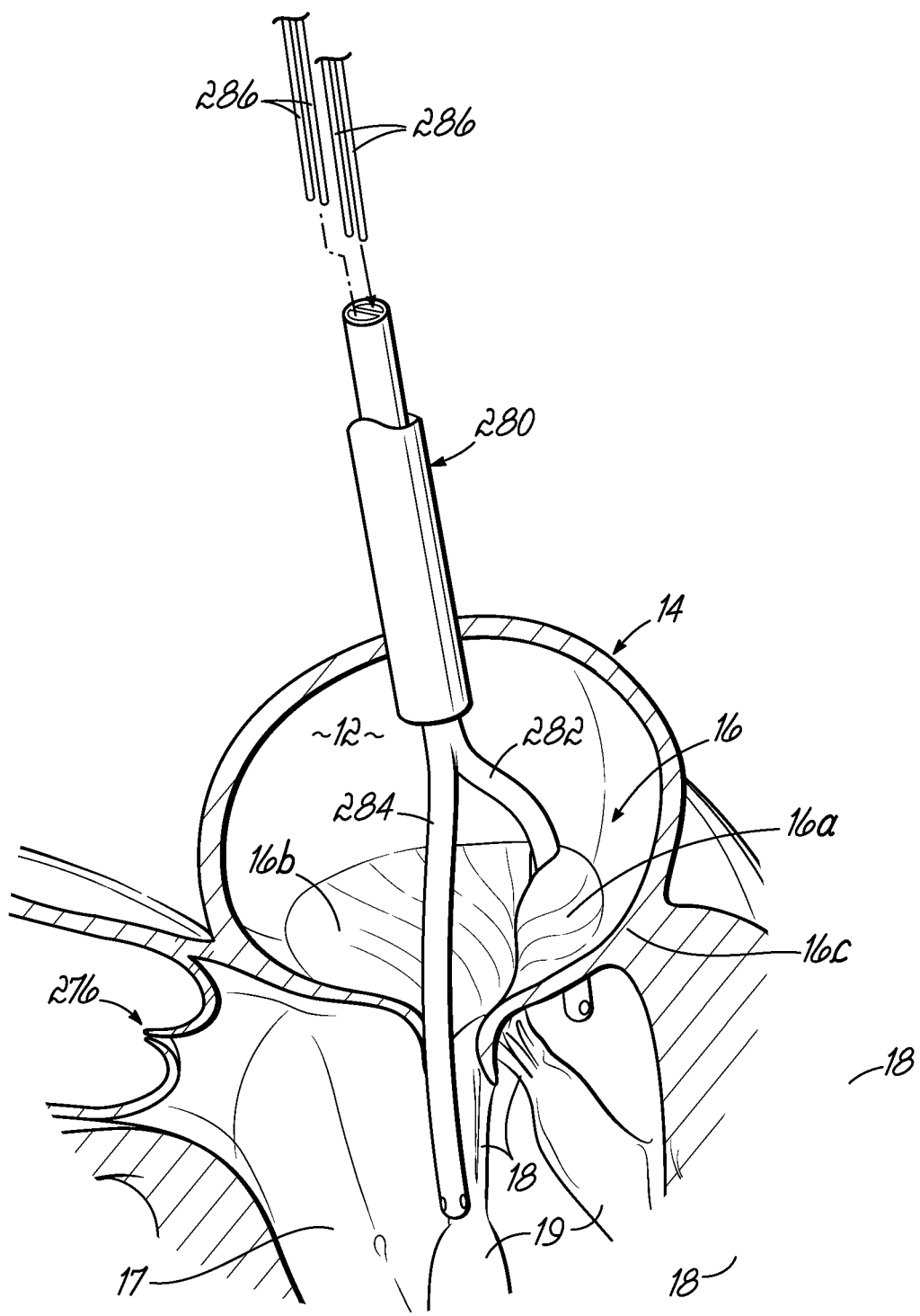
Figure 18C:
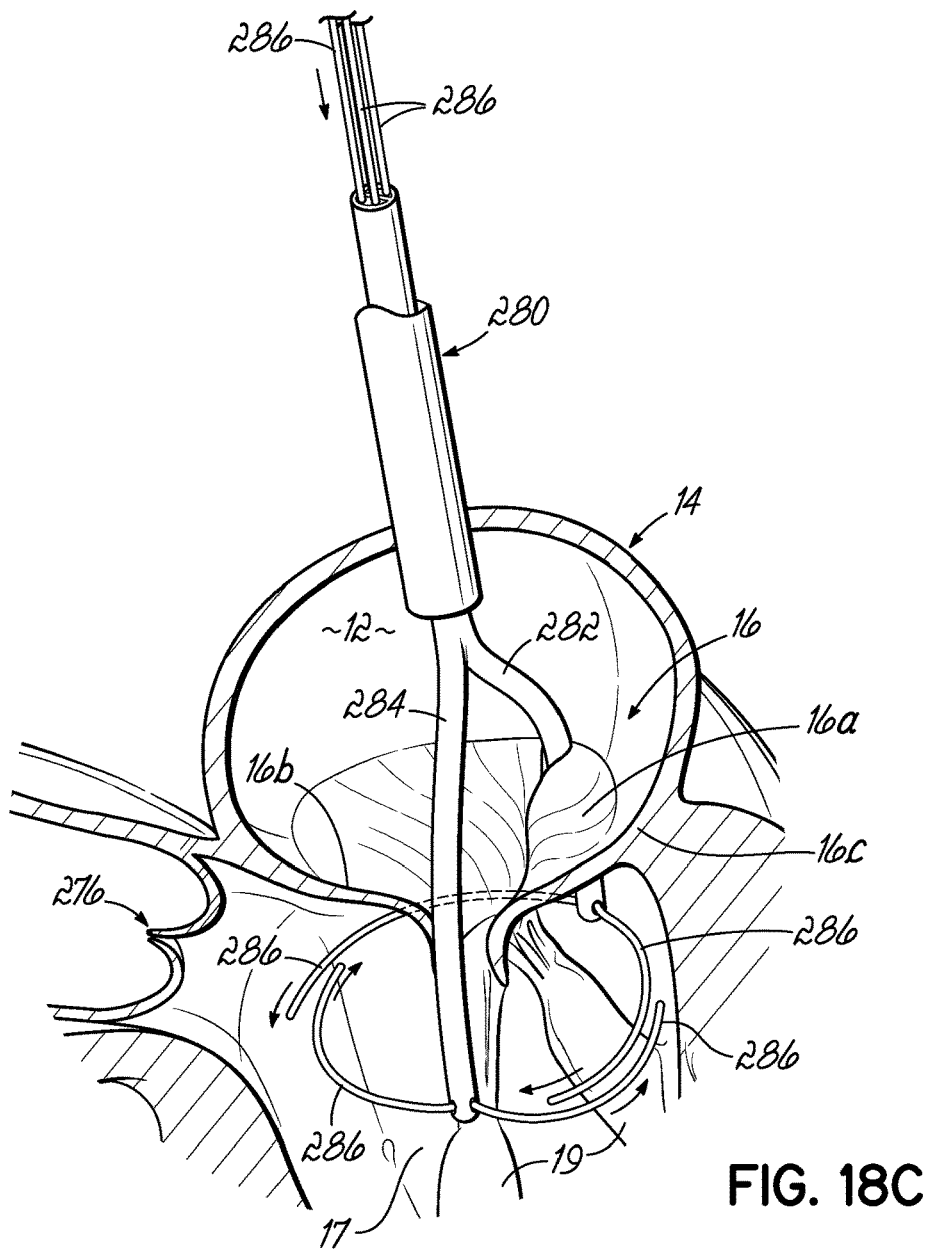
Figure 18D:
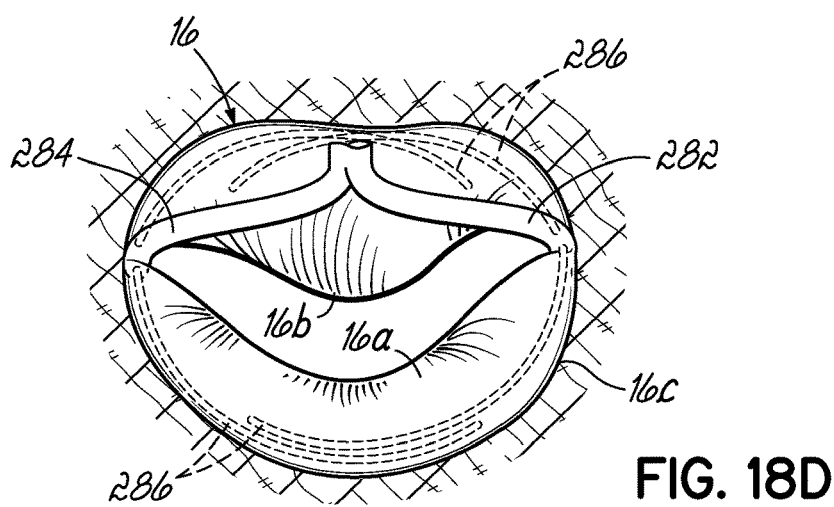
FIG. 18D is a top view illustrating the deployment step of FIG. 18C.
Figure 18E:
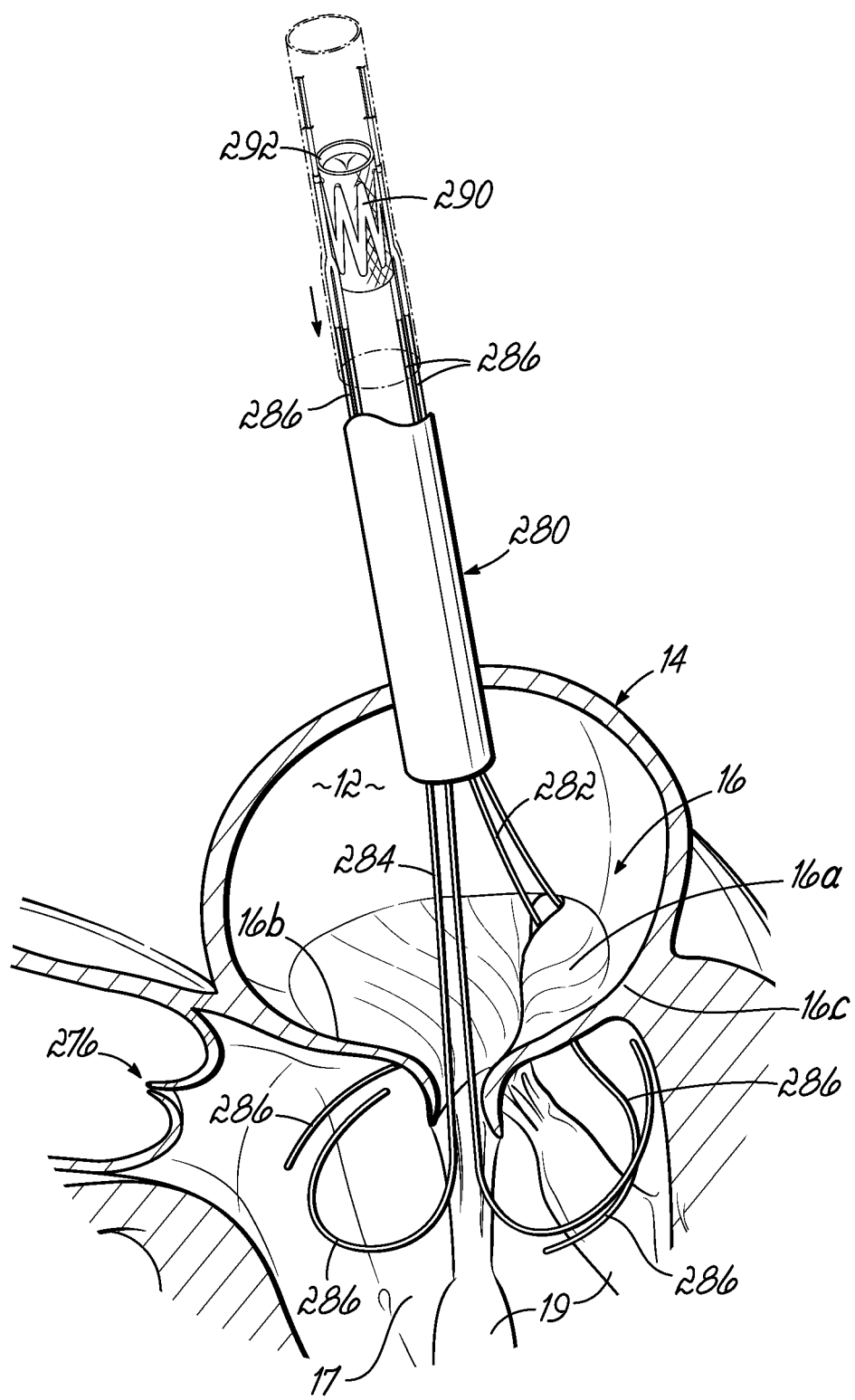
FIG. 18E is a cross sectional view showing a further step in the deployment process.
Figure 18F:
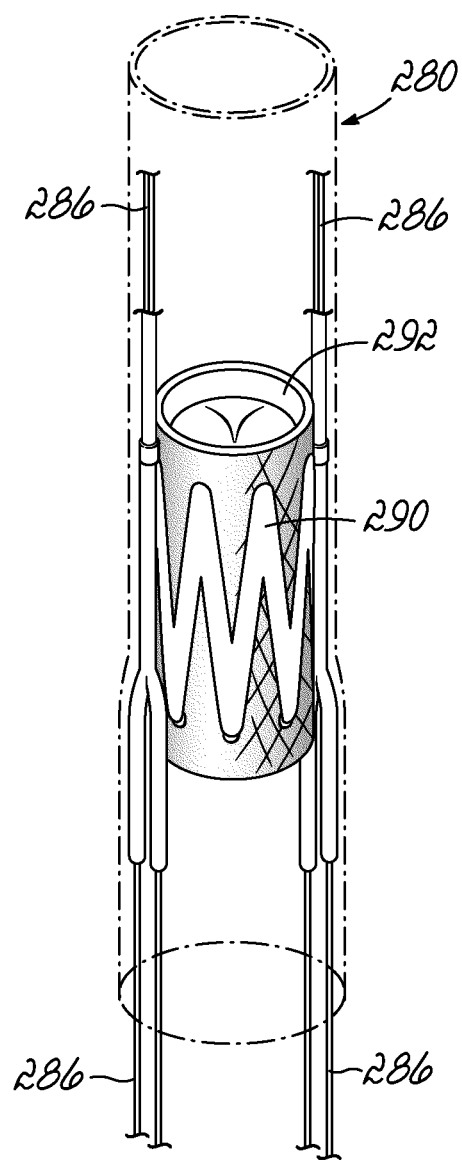
FIG. 18F is a perspective view showing the mitral valve prosthesis and inflatable element in their collapsed conditions within a delivery catheter.
Figure 18G:
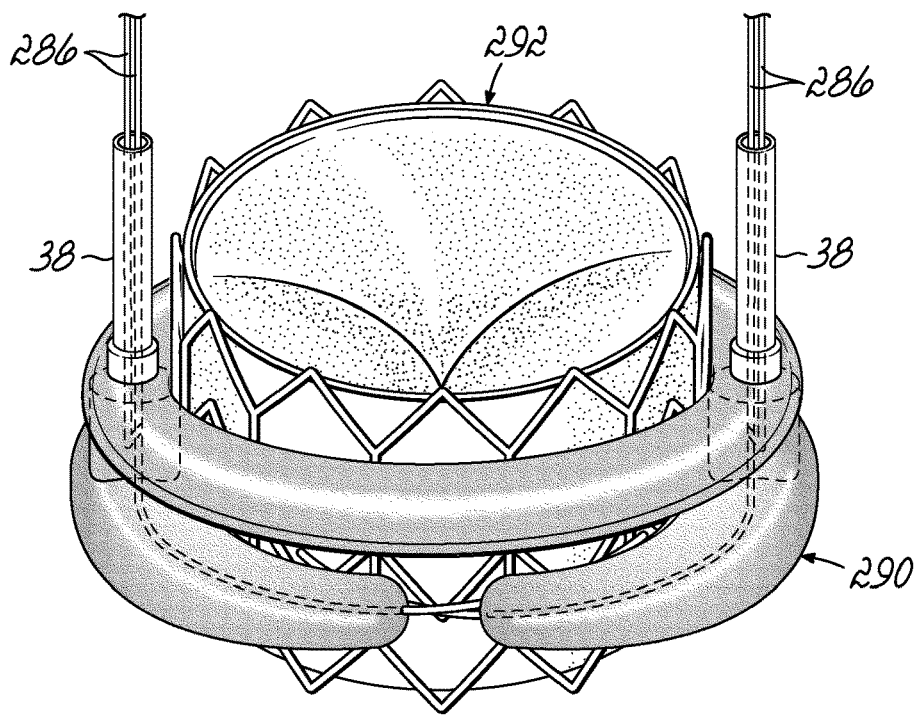
FIG. 18G shows another step in the deployment or delivery process whereupon the expansible mitral valve prosthesis is deployed and expanded with the inflatable element also expanded or inflated, but before withdrawal of the guidewires.
Figure 18H:
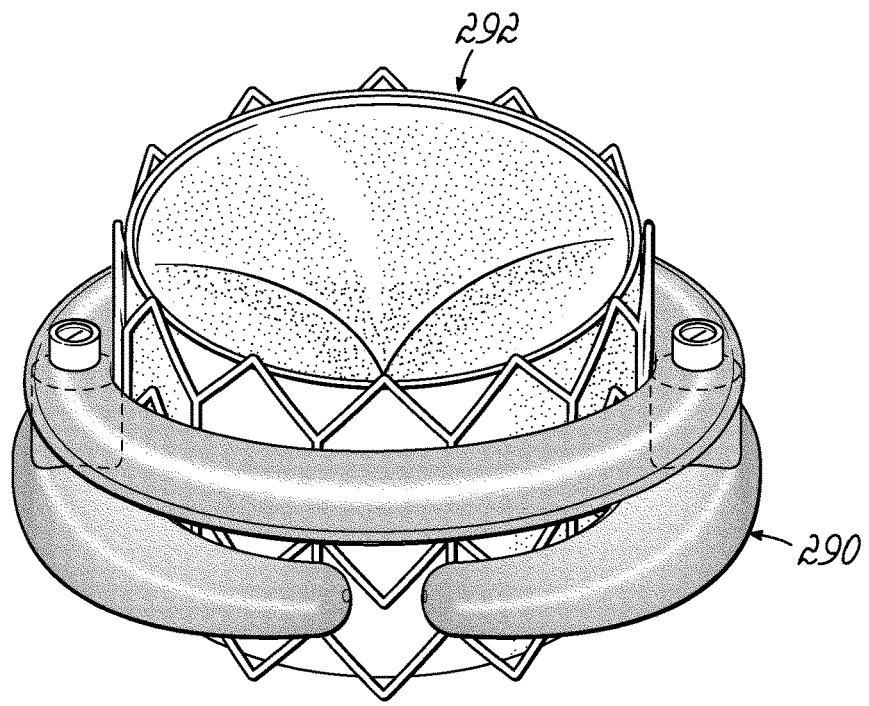
FIG. 18H is a perspective view similar to FIG. 18G, but showing withdrawal of the delivery catheters and guidewires.

FIGS. 18A through 18G illustrate one possible method for implanting an inflatable anchoring and/or sealing structure in accordance with an embodiment of the invention. In this regard, as shown in FIG. 18A, a delivery catheter system 280 is used from above and has two catheter extension portions 282, 284 for entering at the commissure locations and being deployed below the native mitral valve 16 as shown in FIG. 18B. Four guidewires 286 are inserted and deployed through the catheter extensions 282, 284 and naturally follow predetermined paths as shown in FIG. 18C. A view from above is shown in FIG. 18D with the guidewires 286 partially circumscribing the native mitral valve 16 beneath the anterior and posterior native leaflets 16a, 16b. The catheter extensions 282, 284 are withdrawn leaving the guidewires 286 in place as shown in FIG. 18E. The inflatable structure 290 is initially contained within a delivery catheter in a collapsed condition with or without a mitral valve prosthesis 292, as shown (FIG. 18F). The inflatable structure 290 is then inserted and deployed over the guidewires 286 as shown in FIG. 18G and either simultaneously or in a subsequent step, the mitral valve prosthesis 292 is deployed within the inflatable anchoring/sealing system 290 as shown in FIG. 18G. The inflatable elements are inflated with hardenable fluid as described above and shown in FIG. 18H, and the guidewires 286 are removed along with the catheter extensions 282, 284. Respective fluid retention valves are sealed to retain the hardenable fluid within the inflatable elements.

FIGS. 19A through 19D illustrate use of the previously described valve 80 shown in FIG. 7 with one or more inflatable elements 300 beneath the native mitral valve leaflets 16a, 16b for additional sealing and/or anchoring securement. In this regard, when the anchoring arms 88 flip or bend upwardly as indicated by the arrows in FIGS. 19A and 19B the anchoring structure including the arms 88 will trap the inflatable elements 300 against the natural mitral leaflets 16a, 16b and/or against the flange 84 for a high level of stabilization and anchoring. Any number of anchoring arms 88 may be used however, they may generally be used at the midpoints of the natural mitral leaflets 16a, 16b and, if desired, also at locations spaced 90 degrees therefrom or at the commissure locations for additional securement and sealing purposes. It will be appreciated that a valve mounted on an inflatable frame may be substituted for the mechanical prosthetic valve structure 80 shown in these figures. The large flange 84 at the upper or inflow end of the prosthetic valve 80, which resides in the left atrium, improves sealing in the region of the native mitral valve inflow. This type of device is commonly used in mitral valve implants used for catheter procedures. This upper flange 84 may be comprised of a Nitinol (i.e., shape memory material) frame, elastomeric components and a fabric cover, or any other suitable structure. It may instead be comprised of an inflatable material that expands and covers the lower part of the left atrium in the native mitral valve inflow region. The prosthetic valve includes leaflets 80*a*, 80*b*, as shown.

Inflatable elements or members 300 on the left ventricular side or underside of the native mitral valve leaflets are shown in FIGS. 19A through 19D. These inflatable elements 300 may be inserted through the commissures of the native mitral valve 16 (see, e.g., FIGS. 11A through 11E). As shown previously, the inflatable elements 300 may be narrow prior to being inflated so that they slip under the chordae 18 at the commissures of the native mitral valve 16. "Bull horn" shaped or tapered inflatable members 300 may be of various lengths depending on the needs or desires of the application. Ideally, these inflatable elements 300 will engage the mitral valve prosthesis 80 by positioning the native mitral valve leaflets 16*a*, 16*b* between the flange 84 on the upper end and the inflatable element or elements 300 below. The inflatable elements 300 taper to a reduced width or diameter toward their ends. It may be useful for the inflatable elements 300 to instead become larger at the ends. Particularly with reference to the inflatable element 300 or anchor component that sits under the posterior native mitral valve leaflet 166, a large end on an anchor of this type may fill the space under the native posterior leaflet 16*b* and lead to very stable prosthetic valve fixation. Filling the space under the native leaflet 16*b* and at the base of the left ventricle in the region of the attachment of the native posterior leaflet 16*b* may allow insertion of a smaller prosthetic valve 80. It will also lead to greater stability of the implant or valve 80. When surgeons replace the mitral valve, the posterior leaflet 16*b* is frequently folded in sutures to create a pledget that reduces the native mitral annulus diameter and buttresses the valve prosthesis or implant 80. An inflatable implant or prosthesis (not shown in this embodiment) can perform the same function. Inflatable element or elements can also spread the load across a larger area to reduce the risk of valve dehiscence and tissue tearing. In an alternative (not shown) the discontinuous inflatable elements 300 could instead be formed as a continuous annular shape or loop. These designs are, for example, shown in other embodiments herein. These designs could also be used in conjunction with the discontinuous "bull horn" elements 300 shown in this embodiment, or instead of the discontinuous inflatable structure shown. The annular inflatable element or loop could travel along the course of the native leaflets 16*a*, 16*b*, roughly along the same path or course of the inflatable elements 300 shown in FIGS. 19A and 19B, for example, and the continuous inflatable element or loop could extend downward into the left ventricle with, for example, the highest point of the inflatable element or loop impacting or engaging against the underside of the native mitral leaflets 16*a*, 16*b*.

In any of the embodiments shown and described herein, including the present embodiment of FIGS. 19A to 19D, the amount of inflation or filling of the inflatable element or elements, such as elements 300, may be adjusted to achieve a desired size, fit, force application or other effect(s). Also, as has been shown in the above described embodiments, there could be multiple chambers or multiple inflatable elements that may be filled or inflated. In addition, or alternatively, some inflatable chambers or elements may be filled and some may be unfilled or partially filled to achieve a desired size and shape for the inflatable anchoring and/or sealing elements. The anchoring arms 88 may wrap around the anterior and posterior native mitral valve leaflets 16*a*, 16*b*. These arms 88 are typically made from Nitinol or other superelastic materials so that they may be straightened for insertion in a catheter and then spontaneously or automatically bend around the native mitral leaflets 16*a*, 16*b* to anchor the valve prosthesis 80.

Figure 19A:
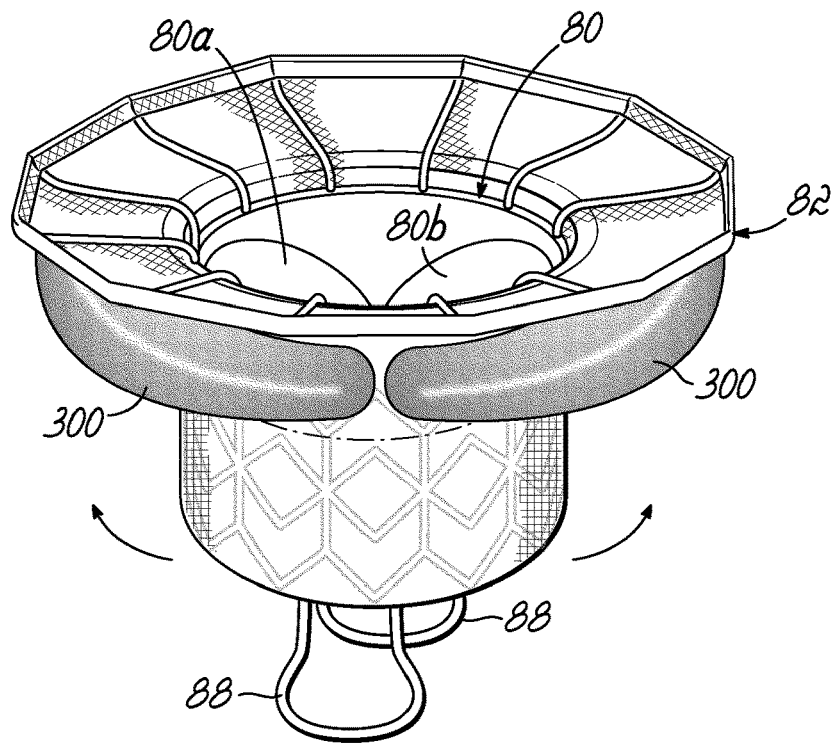
FIG. 19A is a perspective view of another alternative embodiment illustrating a mitral valve prosthesis with anchoring arms in combination with inflatable balloon anchors.
Figure 19B:
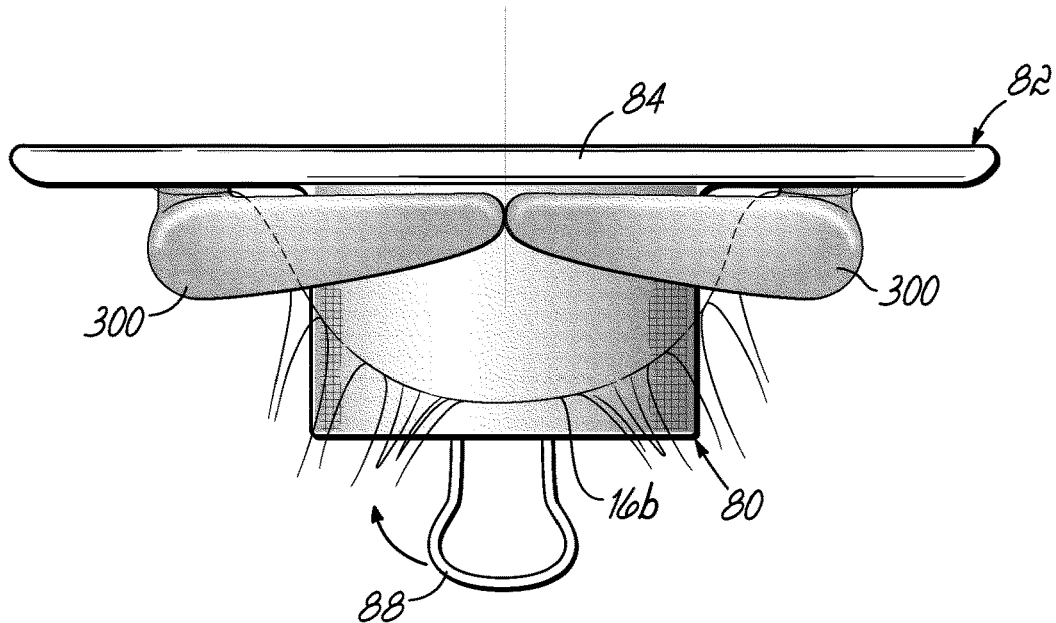
FIG. 19B is a side elevational view of the system illustrated in FIG. 19A.
Figure 19C:
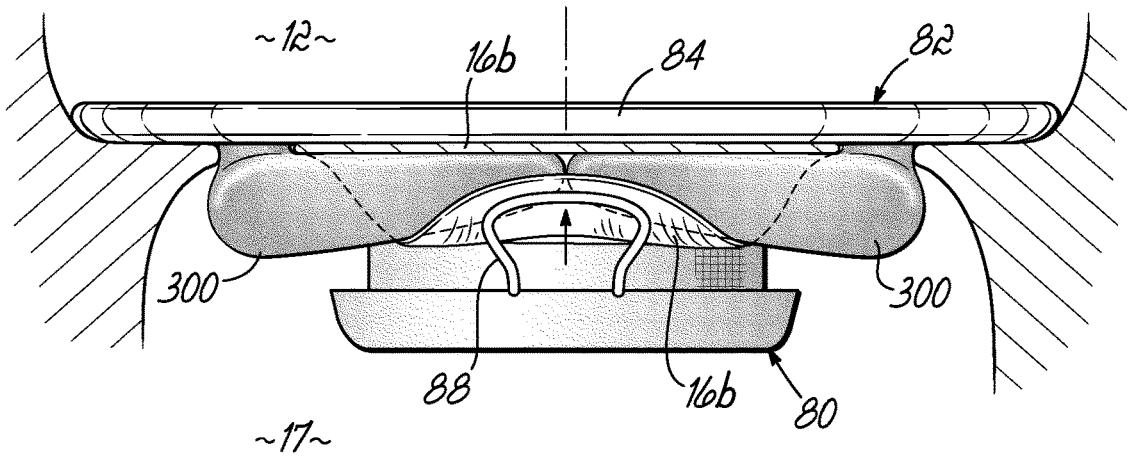
FIG. 19C is a side elevational view of the system shown in FIG. 19B, implanted at the position of the native mitral valve.
Figure 19D:
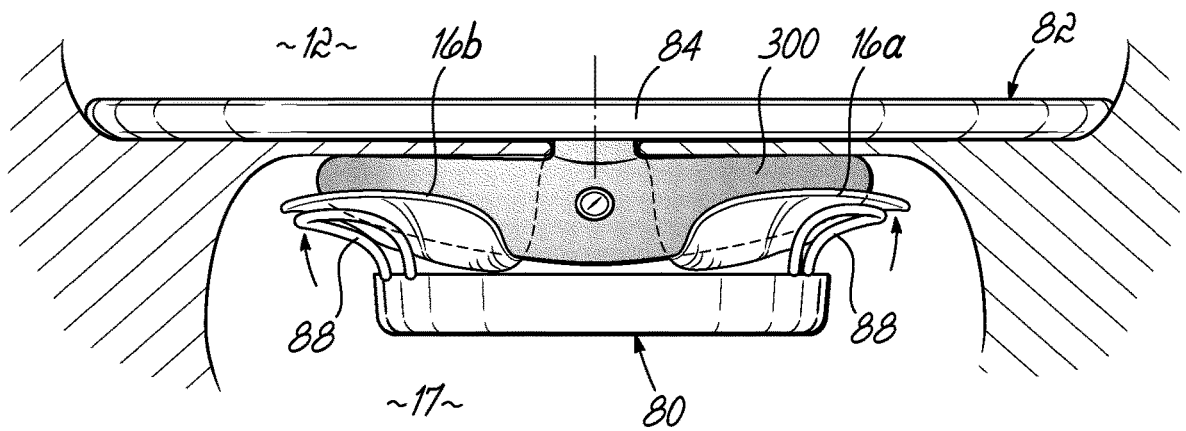
FIG. 19D is a side view of the implanted system shown in FIG. 19C, but viewed from a perspective rotated 90 degrees therefrom.

As shown best in FIG. 19D, the inflation path of the inflatable elements 300 passes through the natural mitral valve commissures 176. The inflatable elements 300 are designed to inflate from the commissure locations 176 and travel toward the middle scallop of both the anterior and posterior native mitral valve leaflets 16*a*, 16*b*. While the inflatable elements 300 are shown with their ends touching in, for example, FIG. 19B, these inflatable elements 300 could be shorter and, therefore, may not engage. Alternatively, the inflatable elements 300 could be longer and, therefore, overlap.

FIG. 19C illustrates a position of the mitral valve prosthesis 80 after it has been delivered over the native mitral leaflets 16*a*, 16*b*. The anchoring arms 88 and the native mitral leaflets 16*a*, 16*b* may engage against the inflatable structure 300. Engagement between the anchoring arms 88 and the inflatable structure 300 is desirable. First, this creates a more solid and stable implant. Second, the ends of the "bull horn" inflatable elements 300 are not attached to each other, so that pressing the native mitral valve 16 and the anchoring arms 88 against the inflatable elements 300 will reduce movement of the ends of the two inflatable elements 300. A large inflatable end (not shown) of the inflatable elements 300 may promote the interaction of the components. It may also have advantages previously described under the posterior native mitral leaflet 16*b* of reducing the native mitral annulus size and stabilizing the overall implant attachment. This will produce a similar effect to the surgeon leaving native posterior leaflet 16*b* behind and passing sutures from the native mitral annulus 16*c* through the plicated posterior mitral leaflet 16*b* into a valve prosthesis 80. Filling space under the native posterior leaflet 16*b* may be particularly useful. The left ventricular wall sits behind the native posterior leaflet 16*b*. The inflatable structure 300 will contact the leaflet 16*b* as well as the annulus 16*c* and the posterior left ventricular wall thereby providing a large surface to absorb the shock that occurs with each contraction of the heart. Also, an inflatable element 300 that fills the space at this location will not obstruct the ejection of blood from the heart. An inflatable element that resides near the native anterior leaflet, and is too large, may result in obstruction to the ejection of blood.

FIG. 19D illustrates a view essentially from native mitral commissure to native mitral commissure, i.e., rotated approximately 90 degrees from FIG. 19C. A portion of the inflatable structure 300 passes through the commissure 176. This also links the inflatable anchoring and/or sealing element (not shown) that may reside above the native mitral leaflets 16*a*, 16*b* on the atrial side with the inflatable portion 300 that resides generally under the native mitral leaflets 16*a*, 16*b* on the ventricular side. The inflation path is shown as a narrow, short tubular structure 302. The part 302 of the inflatable element 300 that passes through the commissure 176 could be much larger. It could also be more spherical or have suitable portions that assist with closing off or sealing the commissure 176 by acting as a "cork" or sealing structure, or by forcing the native leaflet edges 16*a*, 16*b* together at the commissure 176. The inflatable elements 300 are shown wrapping around the native mitral valve leaflets 16*a*, 16*b*. The engagement of the inflatable elements 300 with the native leaflets 16*a*, 16*b* and the anchoring arms 88 may be improved by increasing the size of the inflatable elements 300. For example, the inflatable elements 300 could extend farther below the native mitral leaflets 16*a*, 16*b* and deeper into the left ventricle. In many cases, it will not be possible to tension the chordae 18 (see FIGS. 19E and 19F) enough to make this contact. More generally, stability of the overall implant may be improved by having two anchoring components. One anchoring component may be positioned at the level of the native mitral leaflets 16a, 16b and the native mitral annulus 16c, and a second component may wrap around the native mitral leaflet margins. The stability of the overall implant may be further improved by having these two anchoring components engage or connect to one another.

Figure 19E:
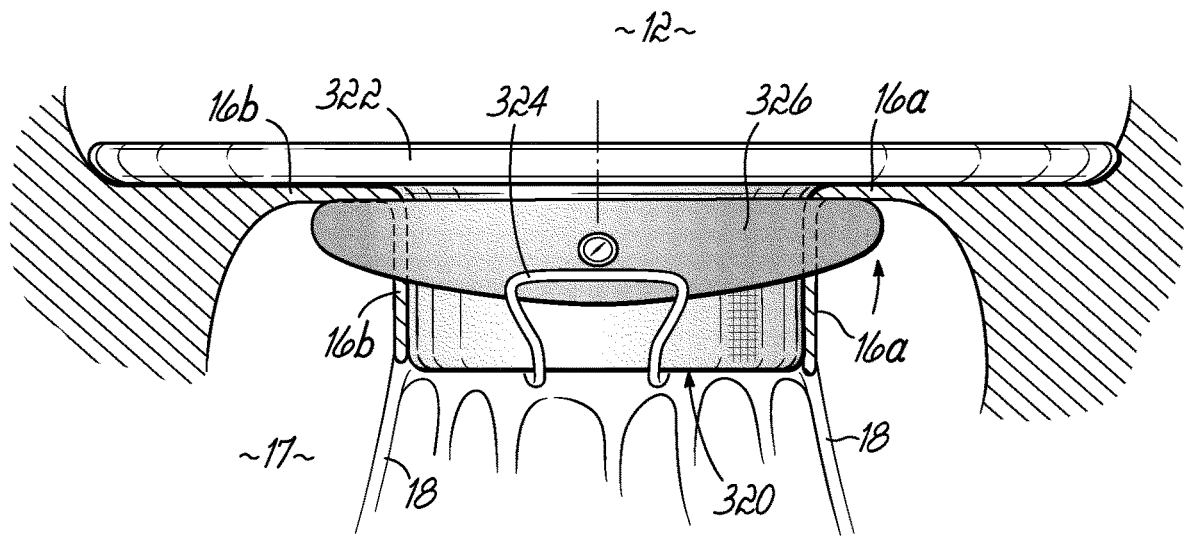
FIG. 19E is a side elevational view of another alternative embodiment in which an inflatable element or balloon is secured to an anchoring arm of the mitral valve prosthesis.
Figure 19F:
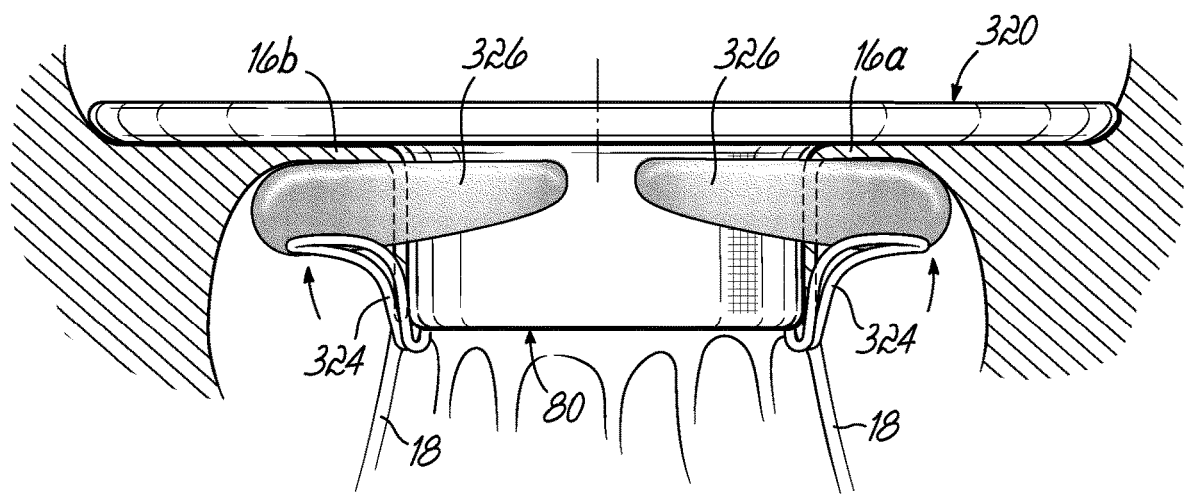
FIG. 19F is a side elevational view of the system shown in FIG. 19E, but from a perspective rotated 90 degrees therefrom.

FIGS. 19E and 19F illustrate another alternative embodiment of a mitral valve prosthesis 320 including a flange portion 322 and anchoring arms 324 as previously described. However, in this embodiment, the anchoring arms 324, which again may include a fabric or other covering to form more of a "paddle" configuration, include balloon anchoring elements 326 secured thereto. In this manner, when the arms 324 flip upwardly as best viewed in FIG. 19F, the inflatable elements 326 also flip upwardly and trap the native mitral leaflets 16a, 16b against the mitral valve prosthesis 320. The balloon elements 326 may be in a deflated condition during delivery and as the arms 324 flip upwardly, and then the balloons 326 may be inflated by a suitable amount to further secure the implantation of the prosthesis 320. These balloon elements 326, as shown in FIGS. 19E and 19F extend substantially beyond the perimeter of the anchoring arms 324 such that they bear against significant portions of the mitral leaflets 16a, 16b and/or portions of the mitral valve prosthesis 320 for anchoring purposes. These arms 324 may extend all the way to the commissures 176, and may have various shapes. For example, extended paddle shaped inflatable elements may be secured to the mechanical anchoring arms 324 to provide more surface area contact between the inflatable arms and the mitral leaflets 16a, 16b and/or the mitral valve prosthesis 320. The balloon elements 326 may be secured to the mechanical anchoring arms 324 by any suitable manner, such as adhesive. This embodiment is especially suitable for a situation where there is very little native mitral leaflet. In this situation, the anchoring arms 324 contact the inflatable elements 326 that are positioned beneath the native mitral valve leaflets 16a, 16b.

Figure 20A:
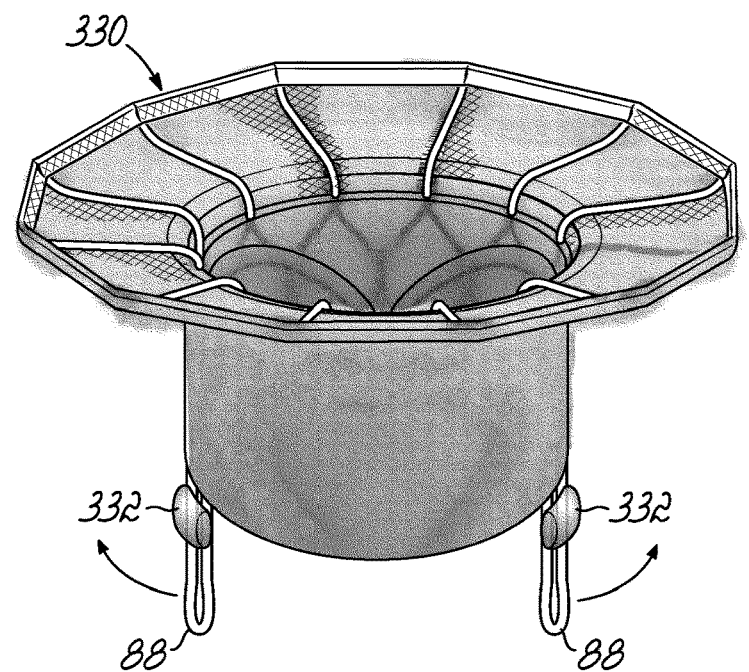
FIG. 20A is a perspective view of another alternative embodiment illustrating a mitral valve prosthesis with anchoring arms, similar to the embodiment of FIG. 19A, but including inflatable elements on the anchoring arms.

FIG. 20A illustrates a mitral valve prosthesis 330 that is similar to the embodiment described in connection with FIG. 19A. An inflatable element 332 is fixed to each of the anchoring arms 88. The attachment of each inflatable element 332 is shown to be on the inside of and at the hinge or bending location of each anchoring arm 88. That is, the inflatable element 332 is located generally at a location where the anchoring arms 88 bend to wrap around the native mitral leaflets 16a, 16b. Of course, the specific attachment may be different than that shown in the figures. Many examples of inflatable elements attached to the anchoring arms 88 are possible. Inflatable elements 332 may be completely attached to the anchoring arms 88, or the inflatable elements 332 may be attached to the anchoring arms 88 at one portion, and the other portion or portions of the inflatable elements 332 may extend beyond the anchoring arms 88. The attachments may be made in various manners, such as by having the inflatable elements 332 adhered along outer surfaces thereof to the anchoring arms 88, or by other methods, such as passing the anchoring arms 88 through the inflatable elements 332.

Figure 20B:
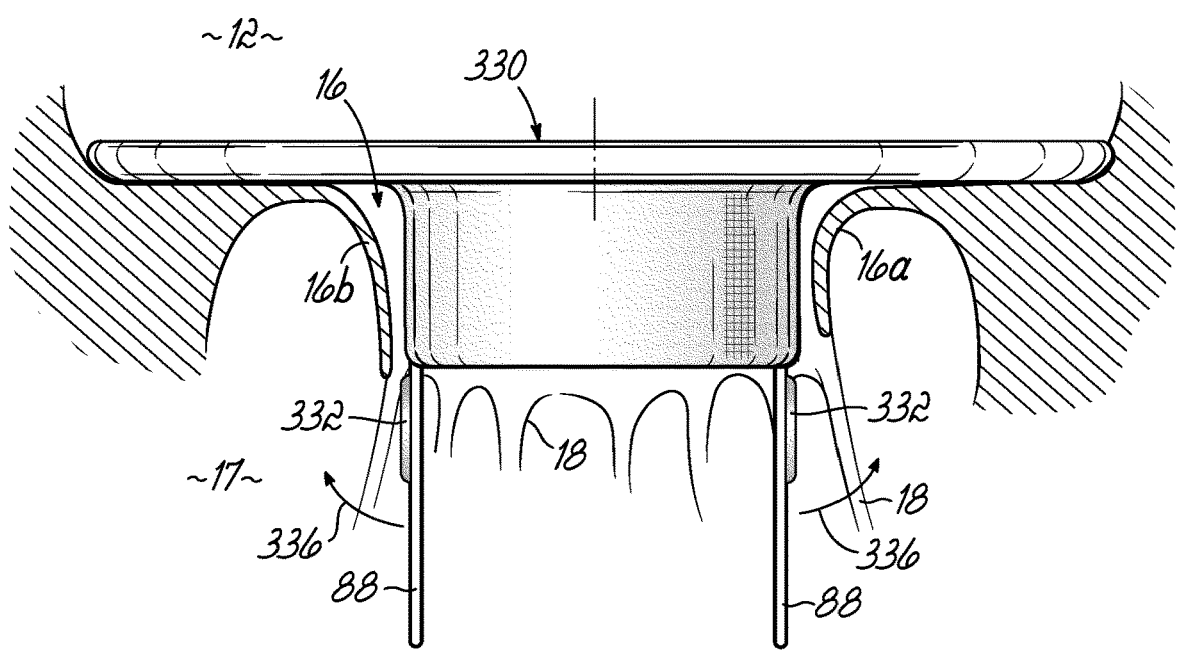
FIG. 20B is a side elevational view of the mitral valve prosthesis shown in FIG. 20A, delivered within the native mitral valve of a patient.

FIG. 20B illustrates the valve prosthesis 330 being implanted inside a native mitral valve 16. The anchoring arms 88 have been directed through the native mitral leaflets 16a, 16b but are not yet hinged or turned radially outward and upward. Arrows 336 are provided to show the intended direction of deployment as the anchoring arms 88 are bent upward. This bending action will preferably be spontaneous or automatic as the mitral prosthesis 330 is deployed from a catheter (not shown) into position, and the arms 88 will wrap around the native mitral leaflets 16a, 16b, typically around the central portions of both the anterior and posterior native mitral leaflets 16a, 16b. The inflatable element 332 is shown on the inside of the folding point or bending location of each anchoring arm 88.

Figure 20C:
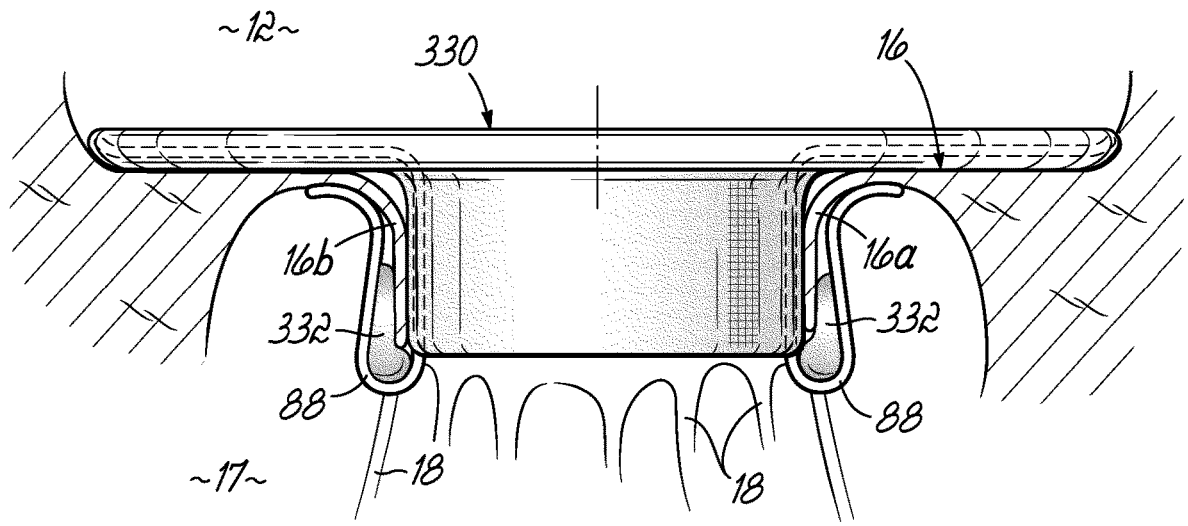
FIG. 20C is a side elevational view similar to FIG. 20B, but illustrating deployment of the anchoring arms to capture the native mitral valve leaflets and inflation of the associated inflatable balloon elements to assist with trapping the native valve leaflets.

FIG. 20C illustrates the anchoring arms 88 deployed and bent into the anchoring position and the balloon element 332 inflated. The balloon element 332 assists the anchoring arms 88 to compress and trap the native mitral leaflets 16a, 16b. The inflatable element 332 may extend beyond the anchoring arm 88 to which it is attached in order to wrap around more of the native leaflets 16a, 16b beyond the end of the anchoring arm 88. The balloon (i.e., inflatable) element 332 may extend to the sides of the anchoring arm 88 to increase the engagement of the native mitral leaflets 16a, 16b to the prosthetic valve 330. The balloon element 332 may extend upward to engage against the underside of the native mitral leaflets 16a, 16b and the native annulus 16c. The inflatable element 332 could be much larger under the posterior native leaflet 16b particularly, and extend all the way to the plane of the native annulus 16c and around much of the circumference of the native annulus 16c. The inflatable element 332 may be a flatter structure in the region of the anterior mitral valve leaflet 16a. This will help to prevent obstruction to left ventricle outflow of blood from the heart. In this figure there is no anchor at the level of the native leaflets 16a, 16b, such as with the previously described "bull horn" element 300 that sits under the native annulus 16c. The inflatable element 332 on the anchoring arm 88 could also engage with a "bull horn" (not shown), such as element 300 (FIG. 19A) when or if combined with one or more other features discussed herein. As described previously, the amount that the inflatable element 332 is filled with inflation fluid may be adjusted, or there may be multiple chambers or elements for inflation purposes that may be filled or unfilled, or partially filled, to achieve a desired result.

Figure 21A:
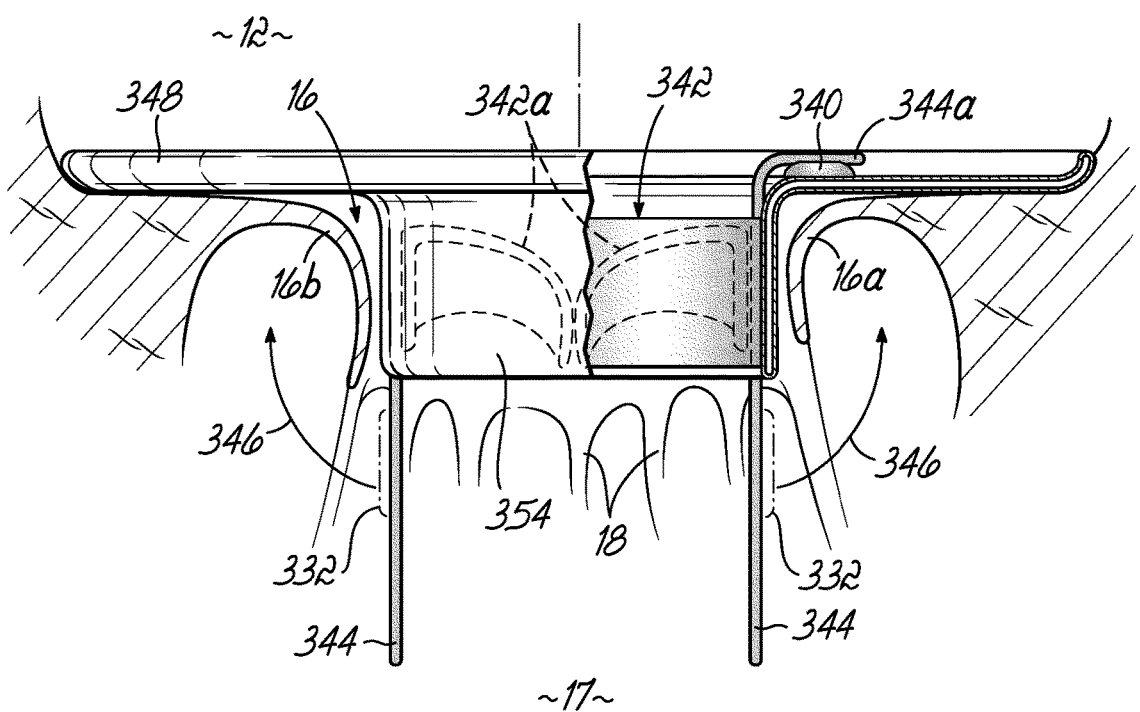
FIG. 21A is a side elevational view of another alternative embodiment illustrating a mitral valve prosthesis in conjunction with inflatable elements used for positioning the prosthetic valve.
Figure 21B:
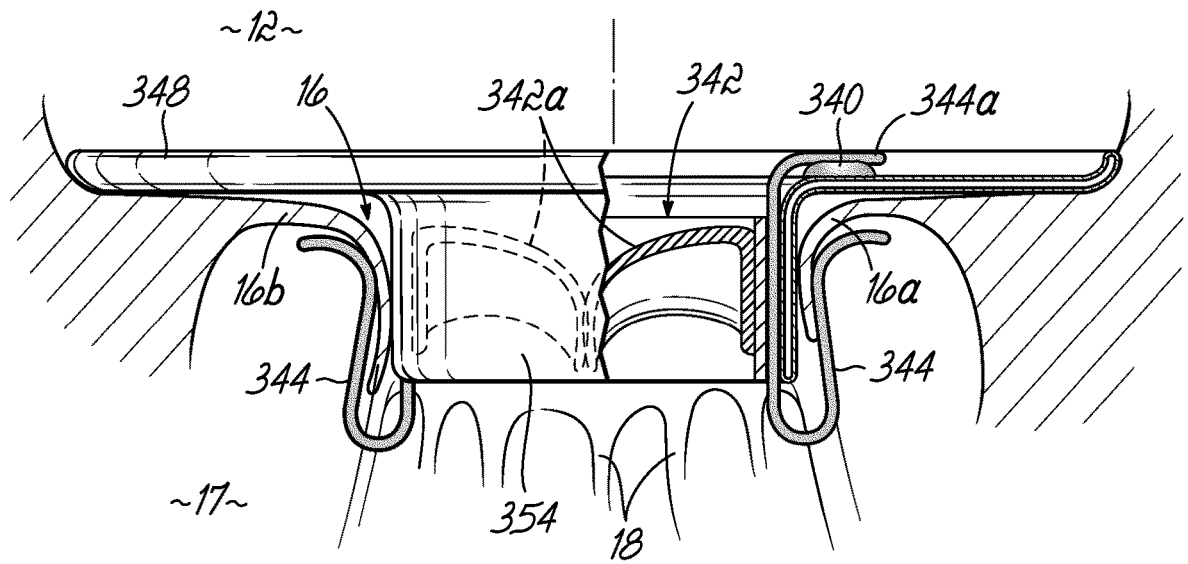
FIG. 21B is a side elevational view similar to FIG. 21A, but illustrating partial inflation of balloon inflatable elements for positioning the prosthetic valve.
Figure 21C:
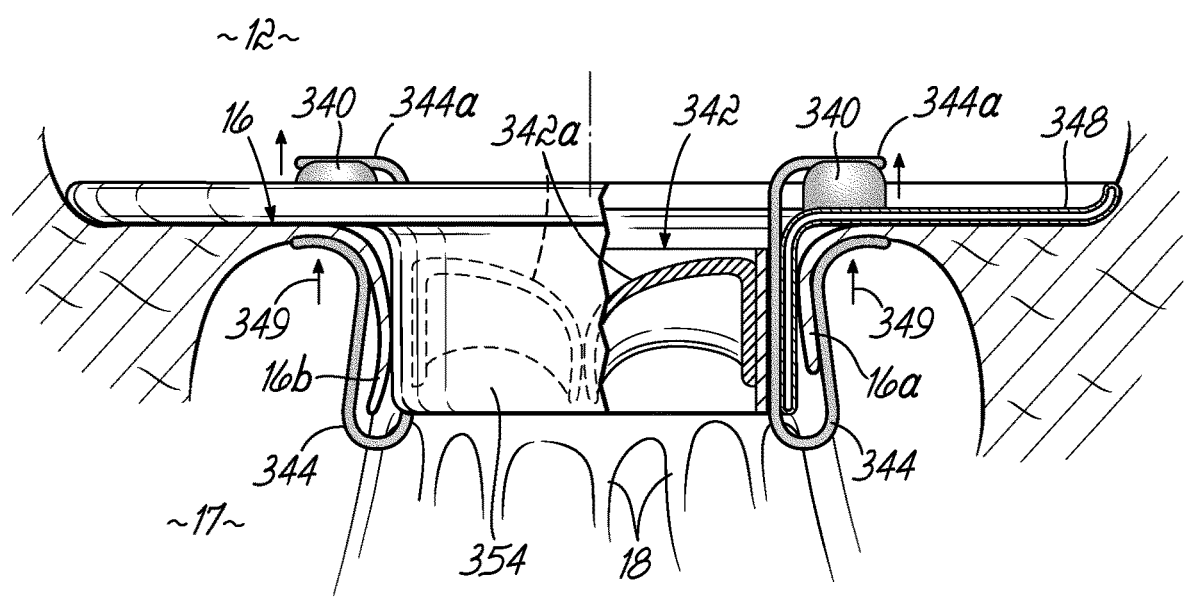
FIG. 21C is a side elevational view similar to FIG. 21B, but illustrating further inflation of the balloon elements to provide further positioning assistance.

FIGS. 21A through 21C illustrate how inflatable elements 340 may be used to move a prosthetic valve 342 relative to the associated native tissue of the mitral valve 16 or to move components of the prosthetic valve 342 relative to each other. Inflatable elements 340 may perform functions as a type of "motor." As shown in FIG. 21A, prosthetic valve 342 with one or more anchoring arms 344 may be moved upward relative to the native mitral valve 16. An anchoring arm 344 is shown in a straight configuration prior to delivery. Arrows 346 show the path that the anchoring arms 344 will take as they wrap around the free edges of the anterior and posterior native mitral leaflets 16a, 16b. This figure illustrates an upper arm portion 344a that sits generally at the top of the valve 342. The entire prosthesis 342 and the anchoring arms 344 may slide freely upward relative to the native mitral leaflets 16a, 16b. The anchoring arm 344 is continuous to the atrial side of the prosthesis 342 as shown in this figure. The upper arm portion 344a sits above an inflatable element 340. This inflatable element 340 may be formed with any desired and suitable shape. The inflatable element 340 may even be a circumferential structure that passes around the entire inflow end or portion of the prosthetic valve 342. The inflatable element(s) 340 may act on more than one of the anchoring arms 344. The inflatable element 340 sits on a stent armature 348 which may be similar to the flange 84 as previously described. The stent armature 348 provides a base for the inflatable element 340 to engage against so that the inflatable element 340 may provide a force to move the anchoring arm 344. The entire prosthetic valve 342 may be covered with a tissue ingrowth fabric.

As shown in FIG. 21B, the prosthetic valve 342 has been delivered and anchoring arms 344 have wrapped around the native mitral leaflets 16*a*, 16*b*. The anchoring arms 344 wrap around the leaflets 16*a*, 16*b*, but it is very difficult for the anchoring arms 344 to apply tension or force on the native leaflets 16*a*, 16*b* that will lift upward on the leaflets 16*a*, 16*b* to tension to chordae 18. Anchoring arms that merely wrap around the leaflets 16*a*, 16*b* but do not provide tension to the leaflets 16*a*, 16*b* and the chordae 18 produce a suboptimal anchoring. The leaflets 16*a*, 16*b* and chordae 18 can still move up and down with each heartbeat due to insufficient anchoring.

FIG. 21C illustrates the inflatable element 340 has been filled with fluid and this lifts upward on the anchoring arm 344. This is shown by the arrows 350 under the leaflets 16*a*, 16*b* and the arrow 352 adjacent the inflatable element 340. A platform in the left atrium, shown as an exemplary stent armature 348 with fabric, provides a base of support to ensure that the inflation results in upward movement of the prosthetic valve 342. This upward movement tensions the anchoring arm 344 against the leaflets 16*a*, 16*b* and loads or tensions the chordae 18. The possibility for movement of the prosthesis 342 is reduced and the valve replacement is more secure. Inflating the inflatable element(s) or "lifting balloon(s)" 340 may be accomplished at the end of the procedure. The amount of inflation may be adjusted to ensure that there is sufficient tension on the native leaflets 16*a*, 16*b* and chordae 18. This may be observed by imaging, such as with an echocardiogram. The interventionist can fill or inflate the inflatable element 340 until the slack and movement is reduced or eliminated. The adjusted, i.e., elevated or lifted, valve 342 has another important advantage. A valve prosthesis that sits too low in the left ventricle may obstruct the function of the heart and impede the ejection of blood. To prevent this problem it is desirable to be able to allow the valve prosthesis to sit or be positioned higher in the heart, with more of the prosthesis located in the left atrium. The anchoring arms 344 on the prosthesis 342 may move relative to the cylindrical body 354 of the prosthesis 342. Using one or more inflatable components 340 to adjust the relative position of the prosthetic valve 342 to native tissues, or relative to other portions of the valve prosthesis 342 may be varied and used in multiple ways to improve valve function and security. The relative positions of components of a prosthetic valve may be suitably adjusted.

Figure 22A:
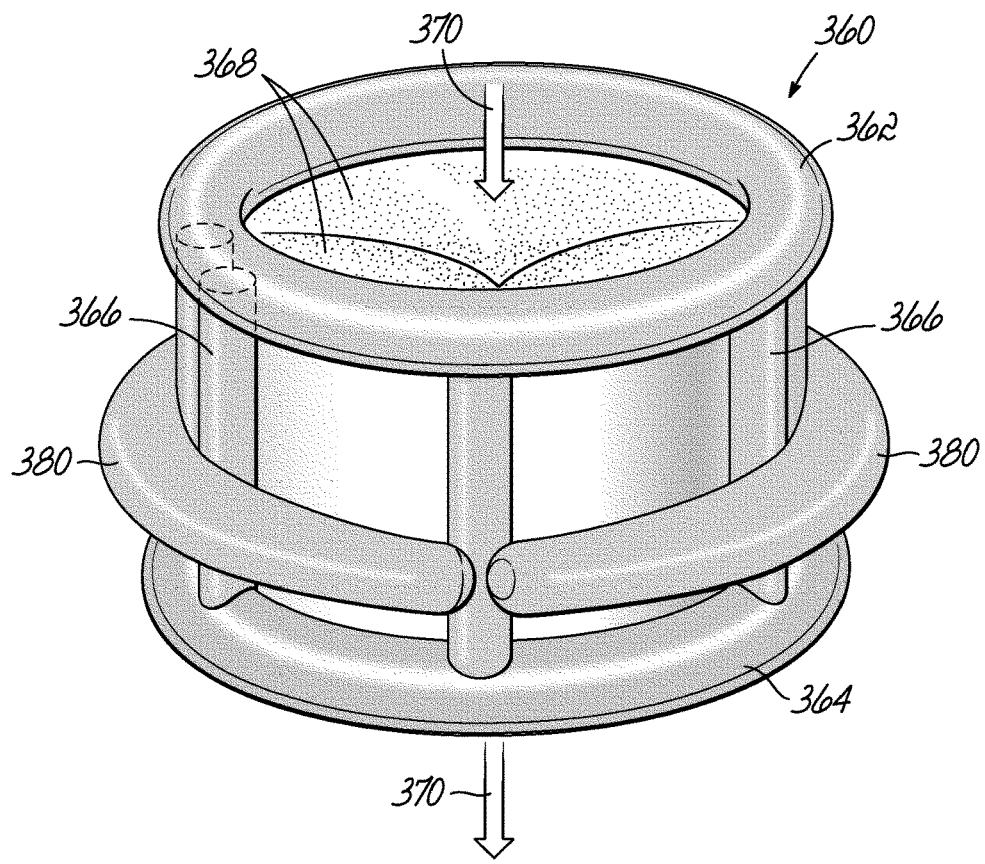
FIG. 22A is a perspective view of another alternative embodiment illustrating an inflatable mitral valve prosthesis.
Figure 22B:
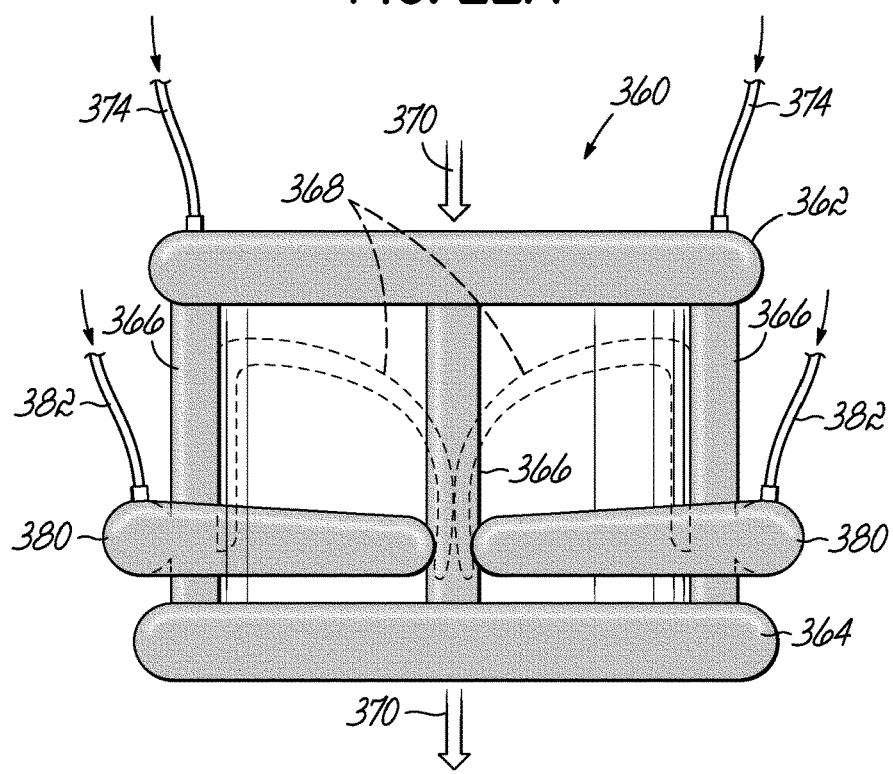
FIG. 22B is a side elevational view of the mitral valve prosthesis shown in FIG. 22A.

FIGS. 22A and 22B illustrate a prosthetic valve 360 that may be collapsed inside a catheter delivery system (not shown) and then inflated inside the patient's heart (see FIG. 1). A circular inflatable support 362 at the top and another circular inflatable support 364 at the bottom of the prosthesis 360 are joined by vertical, inflatable connecting elements 366. Prosthetic leaflets 368 are fixed within the generally circular structure and are shown in dashed line form in FIG. 22B. The direction of blood flow is shown with an arrow 370. The prosthetic leaflets 368 are typically made from treated animal materials or other biologic materials but can be synthetic or even human derived material. The inflatable members 362, 364, 366 are filled with fluids to allow them to take shape. Typically, the fluids are replaced with a material that hardens or polymerizes to maintain the final shape. This may be done with any of the inflatable elements disclosed herein. Tubes 374 are shown to fill the inflatable elements 362, 364, 366 and these tubes 374 are removable after use. FIG. 22B illustrates that the tubes 374 may be temporarily attached to the prosthetic valve 360 to fill the inflatable elements 362, 364, 366 with fluid and materials to harden the implant 360. The prosthetic valve structure 360 shown here includes the addition of two "bull horn" inflatable elements 380. These are shown as located between the two circular rings 362, 364, although the inflatable elements 380 may reside below the lower ring 364. The "bull horn" inflatable elements 380 are designed to be delivered through the native commissures 176 (FIG. 19D) and then inflated below the level of the native leaflets 16*a*, 16*b* (FIG. 19D). This will result in the inflatable elements 380 being placed or positioned on the ventricular side of the native leaflets 16*a*, 16*b* and with the lowest circular inflatable element 364 remaining on the atrial side of the leaflets 16*a*, 16*b*. This will trap the native leaflets 16*a*, 16*b* between the two "bull horn" inflatable elements 380 and the lower continuous inflatable ring 364. The two levels of support (i.e., the "bull horn" inflatable element 380 and the circular inflatable element 364) can have the same diameter or different diameters. Other possibilities for configuration are, for example, that the inflatable elements 364, 380 may have similar or different cross sectional diameters and/or may interlock or otherwise be affixed to one another. As the ventricle contracts, the lower support ring 364 will be forced upward into the "bull horn" inflatable elements 380. The native leaflets 16*a*, 16*b* will pass between the two inflatable elements 364, 380 in a sandwich configuration which will help hold the prosthetic valve 360 in position.

Figure 22C:
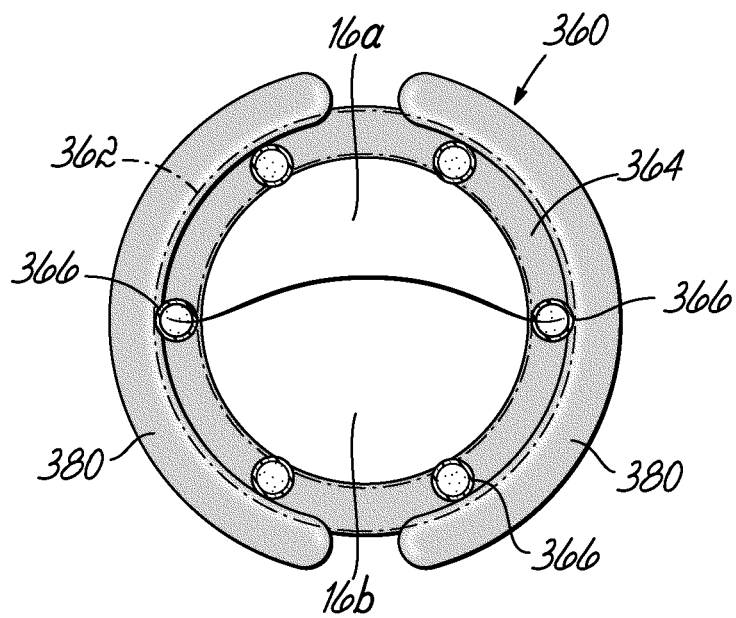
FIG. 22C is a top view of the mitral valve prosthesis shown in FIGS. 22A and 22B.

FIG. 22C illustrates a top view of the implant 360. This includes the complete, continuous circular inflatable elements 362, 364 for the upper and lower portions of the inflatable prosthetic valve 360 and vertical support elements 366 that are also inflatable. The figure illustrates the "bull horn" inflatable elements 380 having a slightly larger diameter of curvature. Uninflated "bull horn" inflatable elements 380 are introduced through the commissures 176 and then inflated such that they expand and travel about the perimeter of the native valve 16.

Figure 23A:
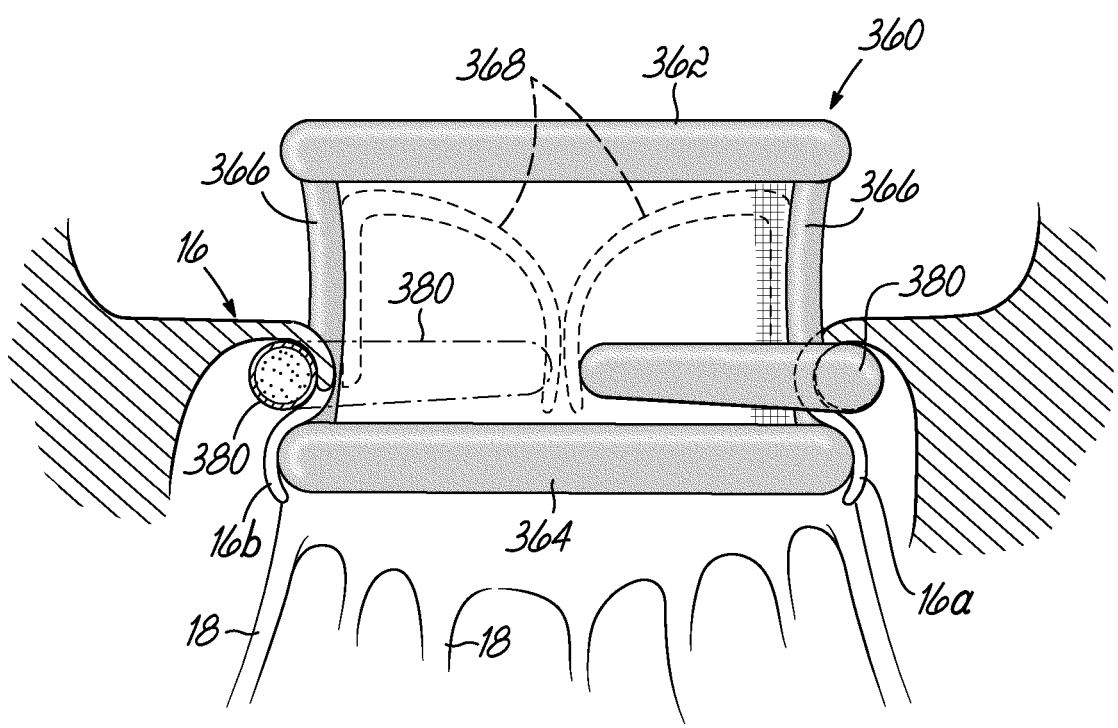
FIG. 23A is a side elevational view, partially cross sectioned and showing the mitral valve prosthesis of FIGS. 22A-22C implanted at the location of the native mitral valve.
Figure 23B:
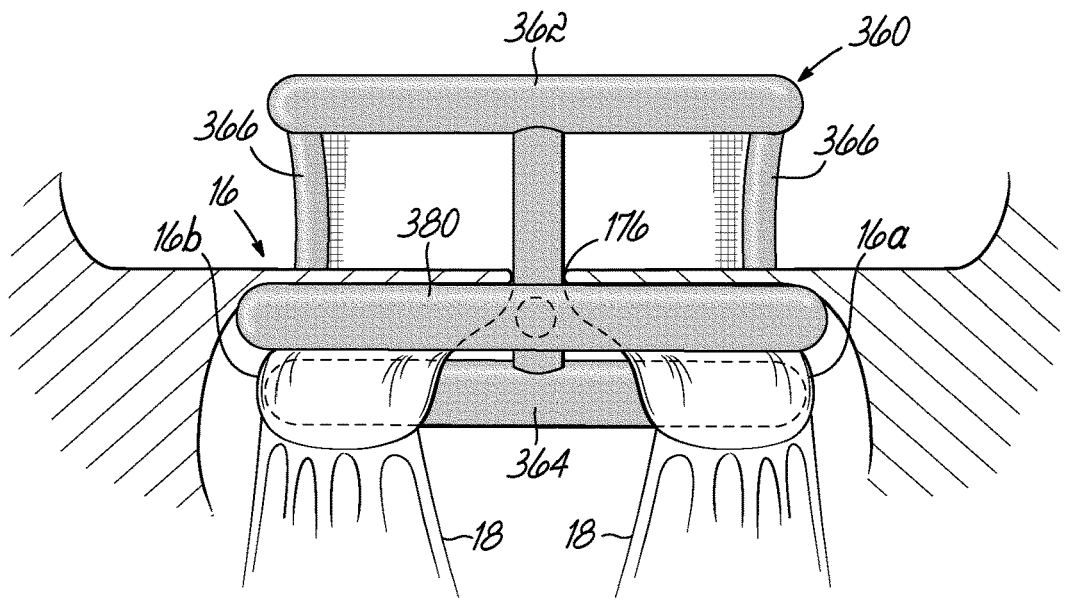
FIG. 23B is a side elevational view similar to FIG. 23A, but illustrated from a perspective rotated 90 degrees relative to FIG. 23A.

FIGS. 23A and 23B illustrate the inflatable prosthetic valve 360 in relationship to the native mitral valve leaflets 16*a*, 16*b*. Only two of the vertical inflatable connectors 366 are shown for clarity. The "bull horn" inflatable element 380, as shown, is positioned on the ventricular side of a native mitral leaflet 16*a*. The lower continuous, circular inflatable element 364 resides on the atrial side of the native leaflets 16*a*, 16*b* even though it sits or resides at a lower level than the "bull horn" inflatable support element 380. The native mitral leaflets 16*a*, 16*b* pass between these two elements 364, 380. These inflatable elements 364, 380 may be constructed so that after inflation the two inflatable, adjacent elements 364, 380 overlap and help trap the native leaflets 16*a*, 16*b* therebetween for a secure prosthetic valve attachment. This will be most effective in the area of the commissures 176 where the continuous, circular inflatable element 364 and the "bull horn" elements 380 will be most capable of providing a force on each other. The "bull horn" supports 380 may be more effective if they are larger in diameter and fill up more space under the native leaflets 16*a*, 16*b*. These two adjacent support elements 364, 380 are both shown as circular in cross section, however, they may be constructed with any suitable cross sectional shape and may be designed to interact or engage each other in various manners. For example, there might be a groove (not shown) on one element that engages with a portion of the other element such as a recess (not shown). To alleviate any tendency for this implant 360 to rock back and forth as the heart beats, any of the other stabilizing features shown or otherwise described herein may be used for lateral support. Other features, which may not be shown or described herein, may also be used for support and stability purposes. For example, support elements may extend from the "bull horn" elements 380, particularly at the commissures 176, or from the continuous circular upper and/or lower rings 362, 364, or from the vertical connecting elements 366. FIG. 23B illustrates the mitral valve prosthesis 360 in a commissure-to-commissure view. The lowest continuous circular inflatable element 364 resides on the atrial side of the native leaflets 16a, 16b, while the "bull horn" shaped inflatable support elements 380 are positioned under the native leaflets 16a, 16b, i.e., on the left ventricular side of the leaflets. As described, these are inflated via a connection at the location of the commissure 176.

Figure 24:
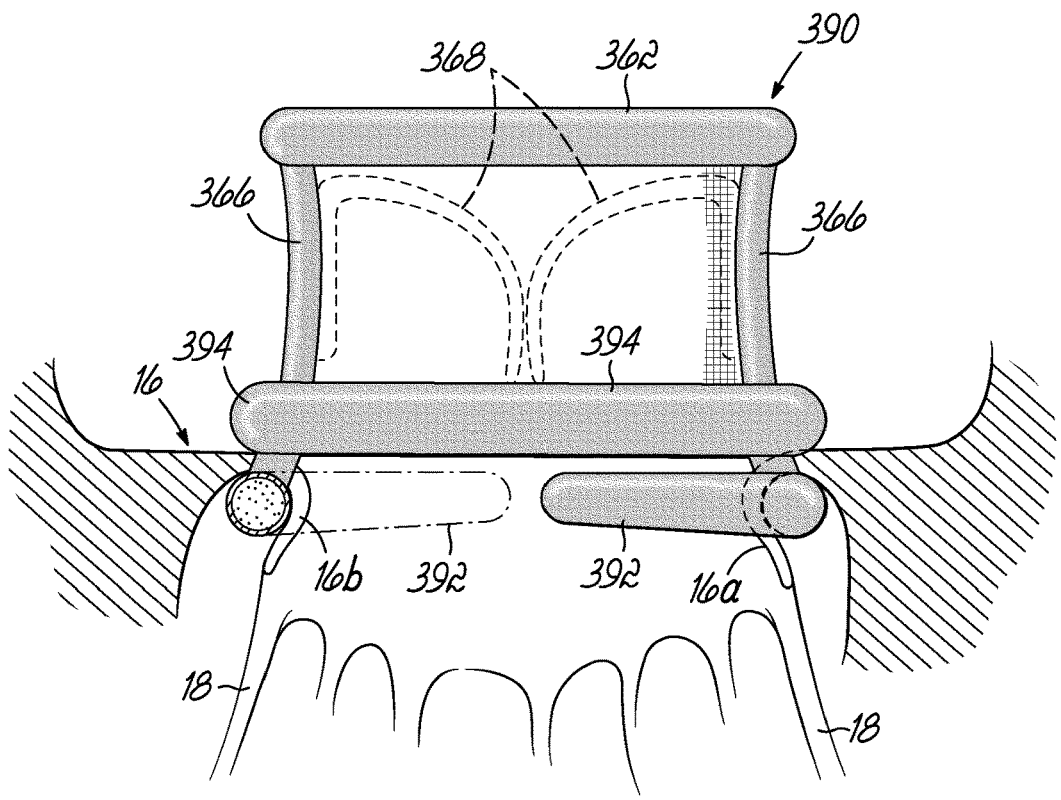
FIG. 24 is a side elevational view of another alternative embodiment of an inflatable mitral valve prosthesis.

FIG. 24 illustrates a view of a variation of the mitral valve prosthesis 390 in which "bull horn" inflatable elements 392 are positioned below a lower circular inflatable element 394 and the "bull horn" support elements 392 reside or position themselves under each of the native leaflets 16a, 16b, on the ventricular side of the leaflets 16a, 16b. The lower continuous, circular inflatable element 394 is positioned above the native mitral leaflets 16a, 16b on the atrial side of the native valve 16.

Figure 24A:
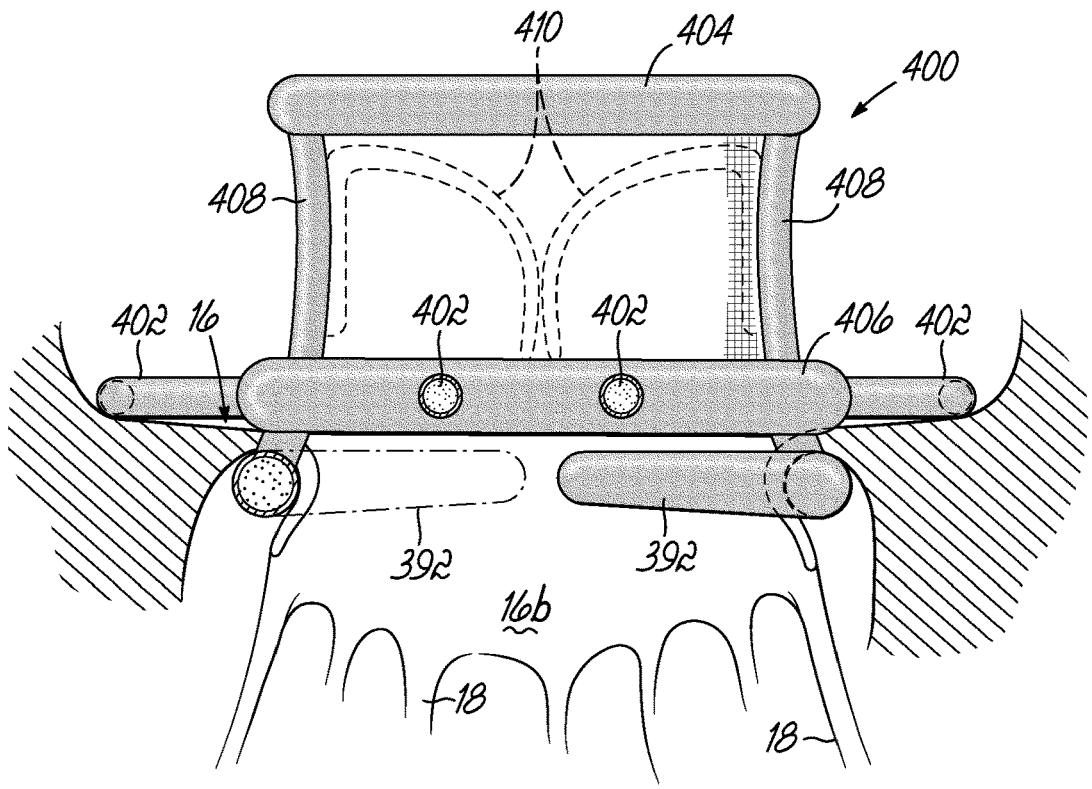
FIG. 24A is a side elevational view of another alternative embodiment illustrating an inflatable mitral valve prosthesis similar to FIG. 24 but with further stabilization structure.
Figure 24B:
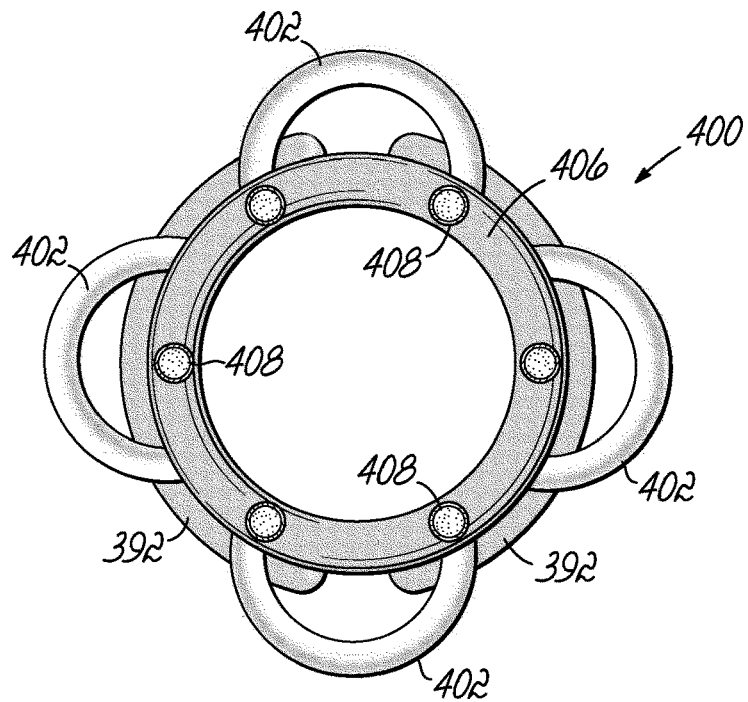
FIG. 24B is a top view of the inflatable mitral valve prosthesis shown in FIG. 24A.

FIGS. 24A and 24B illustrate another alternative mitral valve prosthesis 400 having stabilizing support elements 402. As with the prosthesis described above, the prosthesis 400 may be comprised of inflatable elements 404, 406, 408 connected together and including prosthetic leaflets 410. Although not shown, one option for providing additional stability, such as preventing a rocking back and forth, is to make the upper circular ring 404 large enough that it covers the lower portion of the left atrium. Such a ring 404 may look less like a ring than a structure similar to that shown as a flange in previous figures such as FIG. 19A. This type of ring or inflated flange 404 would reside along the bottom of the left atrium. Another option is to add additional supports. These supports may take various shapes and configurations. FIGS. 24A and 24B illustrate inflatable supports 402 extending from the lower, circular inflatable ring 406 to form arches. These arches 402 will engage against the lower portion of the left atrium to prevent back and forth rocking action of the prosthetic valve 400. The surface profile of the left atrium is not regular. The portion of the atrium adjacent or closest to the native aortic valve 16 has a steep angulation. These individual arches 402, or even more linear support members may adapt to the contours of the atrium and stabilize the valve prosthesis 400 to prevent rocking. The inflatable support members 402 are shown extending from the lower circular ring 406, however, they could also extend from the vertical struts 408 or connecting elements that join the upper ring 404 to the lower ring 406. These support arches 402 or other support elements may be used in various numbers and configurations, for example, and there may be "arch over arch" designs or other configurations, and the same types of elements may be used on any portion of the prosthesis 400.

Figure 25A:
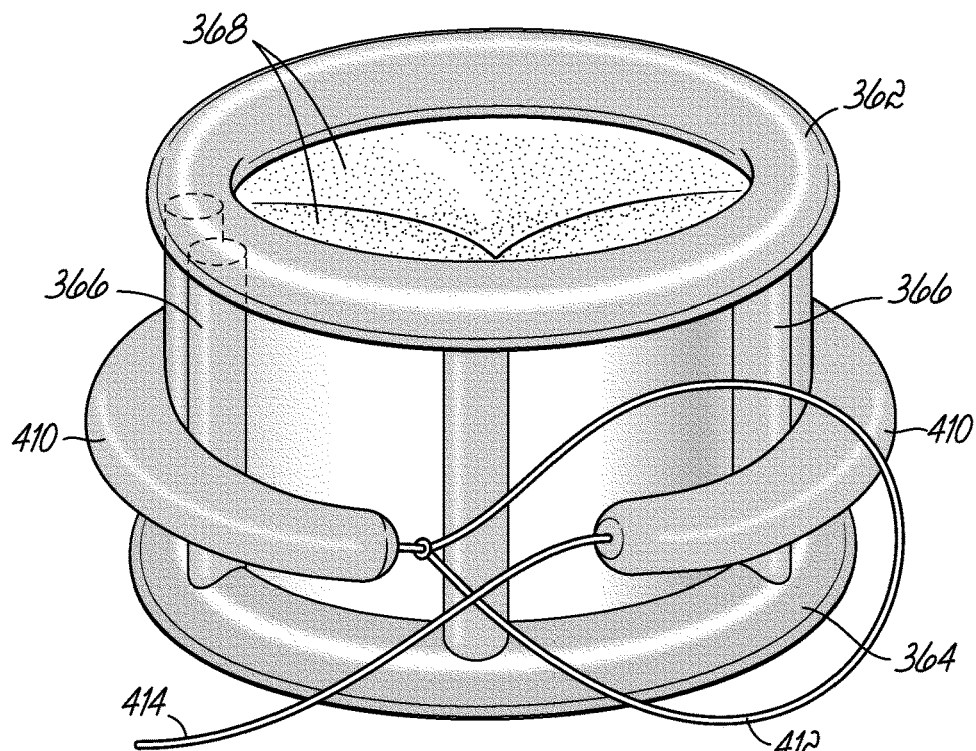
FIG. 25A is a perspective view of another alternative embodiment illustrating a mitral valve prosthesis including structure for joining adjacent ends of inflatable elements together.
Figure 25B:
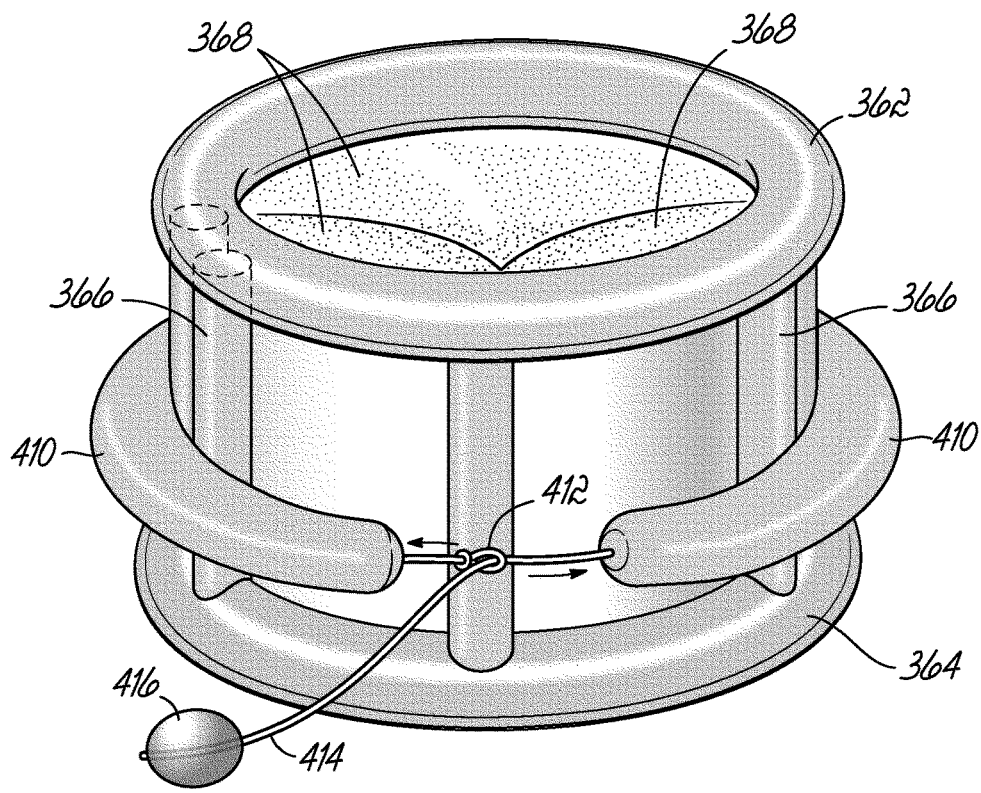
FIG. 25B is a perspective view similar to FIG. 25A, but illustrating a subsequent time in the process of joining the ends together.
Figure 25C:
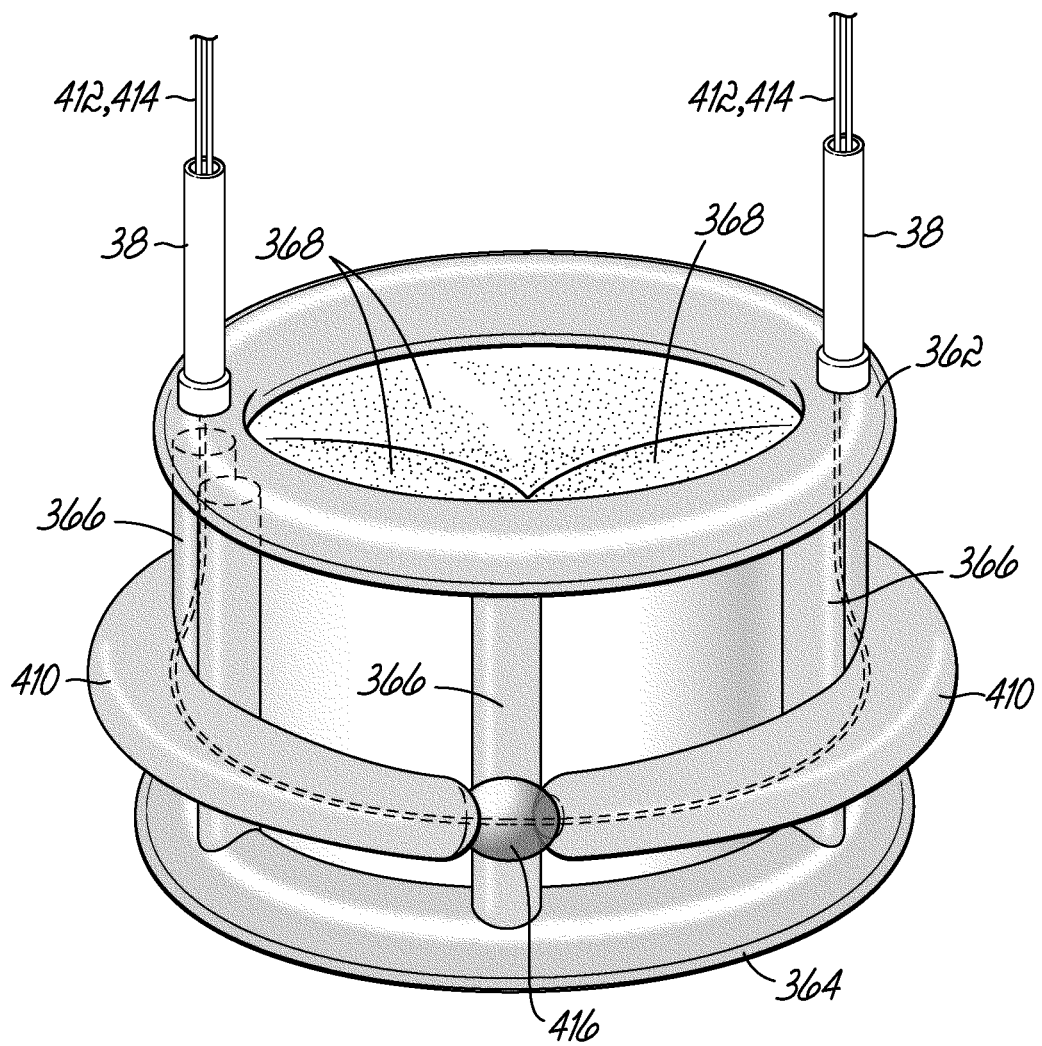
FIG. 25C is a perspective view similar to FIG. 25B, but illustrating completion of the process for joining the ends together.

FIGS. 25A, 25B and 25C illustrate an alternative that improves stability. In particular, the ends of two inflatable support elements 410 may be stabilized by joining them together to produce a more complete, circular structure. This can be accomplished in a variety of ways, with examples to follow. FIG. 25A illustrates a large loop 412 being passed through one inflatable support element 410 and a straight wire-like element 414 then passed through the end of the adjacent support element 410. The loop 412 is large enough that the straight wire-like element 414 will be easily directed through the loop 412 and a balloon 416 is then inflated on the end of the straight wire-like element 414 as shown in FIG. 25B. In FIG. 25C the loop 412 and the wire-like element 414 have been pulled back and the ends of the adjacent "bull horn" inflatable elements 410 are then pulled or drawn together. The delivery path to accomplish these maneuvers is shown in the FIG. 25C at the upper portion of prosthetic valve 400.

Figure 26A:
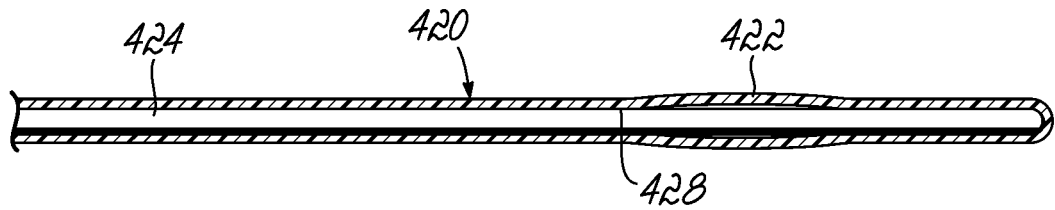
FIGS. 26A-26C are cross sectional views illustrating an end portion of an inflatable element used for purposes of locking adjacent ends of inflatable elements together.
Figure 26B:
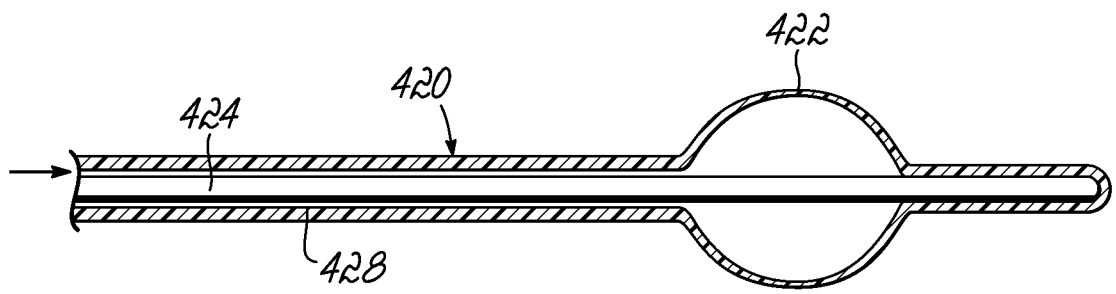
Figure 26C:
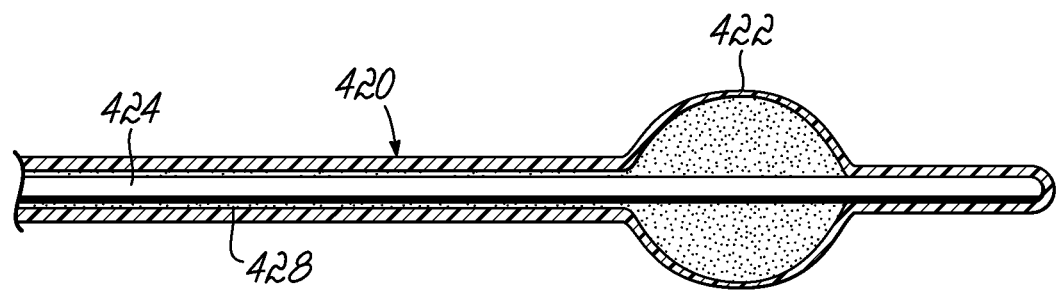

FIGS. 26A, 26B and 26C illustrate a progression of figures showing the end of an inflatable anchoring element 420, such as any of the bull horn elements described herein. The end of the element 420 includes a portion 422 that may be inflated to create a bulge or other structure that may be used as a portion of a "lock." Locking the ends of the inflatable anchoring elements 420 (only one shown) together will create a much stronger and more durable attachment of an associated valve prosthesis (not shown) to the native mitral valve (not shown). Any of the inflatable anchoring elements that include unjoined, adjacent ends, typically for implantation purposes, may be joined together for this purpose. For example, an inflatable anchoring element residing under a natural leaflet (such as a "bull horn" type) could be engaged with an inflatable element that is delivered on the anchoring arms that wrap around the native leaflets as previously described. Tying such anchoring components together will improve stability of the prosthesis. As shown in FIGS. 26A, 26B and 26C, an inflatable balloon element 420 may surround a Nitinol wire 424. There is a channel 428 for inflation that allows the balloon 420 to inflate. The balloon 420 can be permanently filled by filling with a hardening resin. The Nitinol wire 424 may be on the inside of the inflatable element 420 or on the outside of the inflatable element 420, although this latter design is not shown. Once inflated, as shown in FIG. 26C, this bulging portion 422 may be used to interconnect with another inflatable device (not shown) such that, for example, the other portion includes a donut-shaped loop to divide an opening. The loop would be inflatable and the uninflated element 420 shown in FIG. 26A would be passed through the inflatable loop. The inflatable element 420 would be inflated as shown in FIGS. 26B and 26C in order to fill the loop with the bulging portion 422 and prevent the inflated element 420 from passing back through the inflated loop. To further tighten the system, the inflatable anchoring element 420 may be tensioned by pulling on the end opposite to the one that carries the inflatable portion 422. FIG. 26C illustrates the inflatable portion 422 being filled with a hardening resin or other material to keep the system stable after deployment.

Figure 27A:
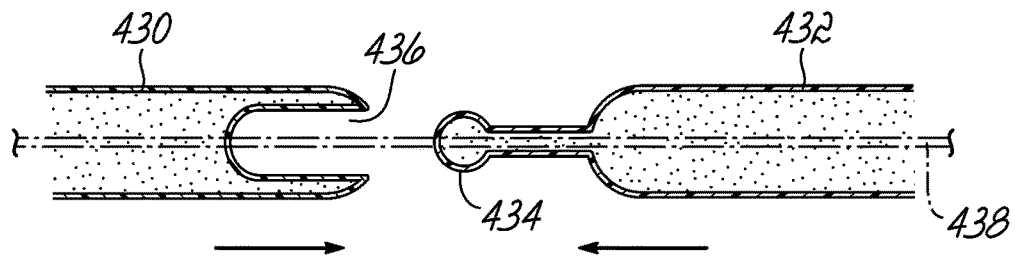
FIGS. 27A and 27B illustrate cross sectional views of alternative locking elements that may be used for locking ends of inflatable elements together.
Figure 27B:
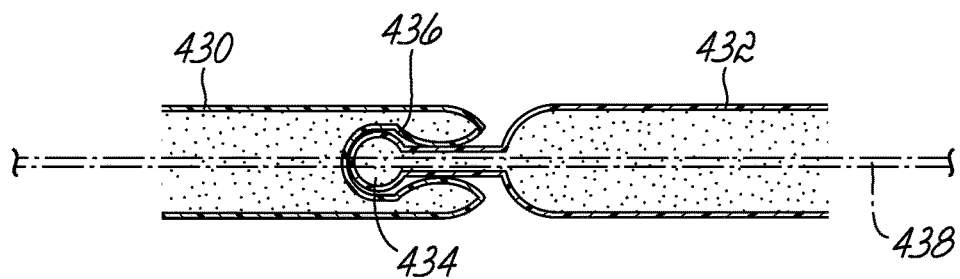

FIGS. 27A and 27B illustrate another alternative embodiment for connecting and locking the ends of two adjacent inflatable anchoring elements 430, 432 together. In this case, an inflatable sphere 434 may be engaged inside the end of an adjacent inflatable structure 436. The two inflatable structures 434, 436 may be guided together by traveling over a common guidewire 438. The second structure 438 may then be inflated to close the "mouth" of the junction and trap the two separate, inflatable elements 434, 436 together. There are many other options. A saw tooth arrangement (not shown) could be used rather than a sphere, for example.

Figure 28A:
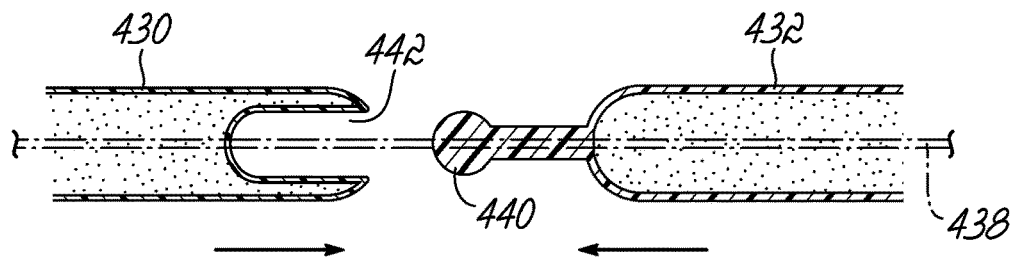
FIGS. 28A and 28B illustrate further alternative structure for locking ends of inflatable elements together.
Figure 28B:
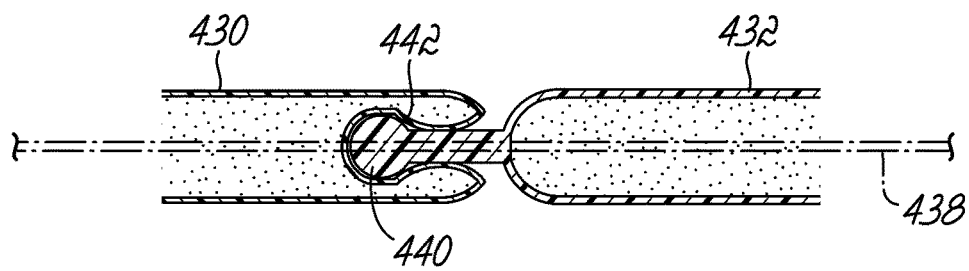

FIGS. 28A and 28B illustrate locking structures 440, 442 that are very similar to those shown and described with respect to FIGS. 27A and 27B. However, in this embodiment, the sphere or other lock element 440 is not inflatable, but rather is a solid or otherwise rigid or non-inflatable structure. The receptacle portion 442 is inflatable and locks with the solid sphere-shaped structure 440 as shown in FIG. 28B. These components 440, 442 could be reversed, i.e., the non-inflatable structure could be the receptacle and the inflated structure could be the inserted lock element.

Figure 29A:
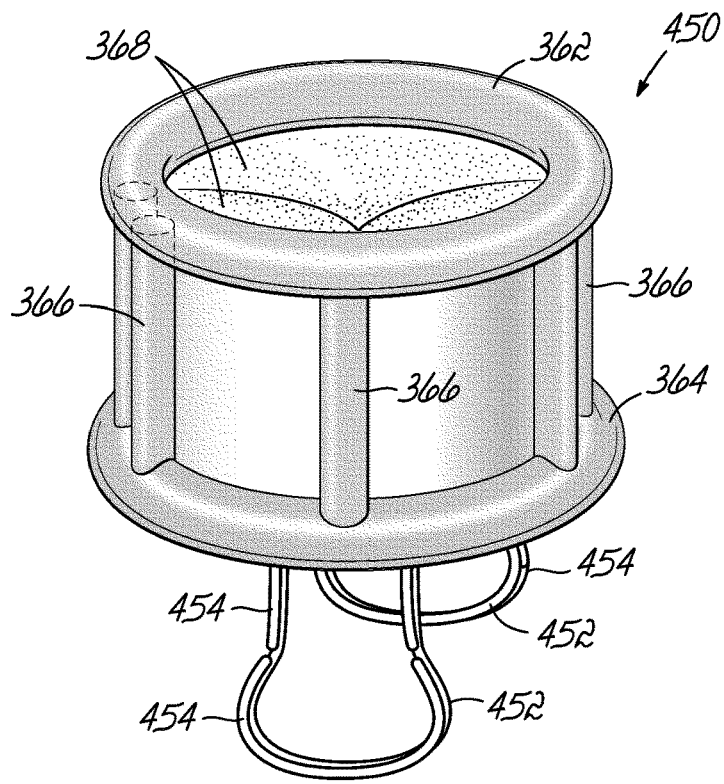
FIG. 29A is a perspective view of another embodiment illustrating an inflatable mitral valve prosthesis with anchoring arms in combination with inflatable balloons.

FIG. 29A illustrates another alternative inflatable valve prosthesis 450. Similar to other embodiments described herein, this valve prosthesis 450 includes anchoring arms 452 configured to wrap around the native mitral leaflets 16*a*, 16*b* during deployment. These anchoring arms 452 also carry inflatable elements 454 that may be filled and expanded. The size and configuration of the inflatable elements 454 may be varied. The inflatable elements 454 may be attached to the anchoring arms 452 or the anchoring arms 452 may pass through the inflatable elements 454. The inflatable elements 454 may be completely or only partially attached to the anchoring arms 452. If the inflatable elements 454 are partially attached to the anchoring arms 452, other portions of the inflatable elements 454 may extend beyond the anchoring arms 452 when the inflatable elements 454 are filled and expanded.

Figure 29B:
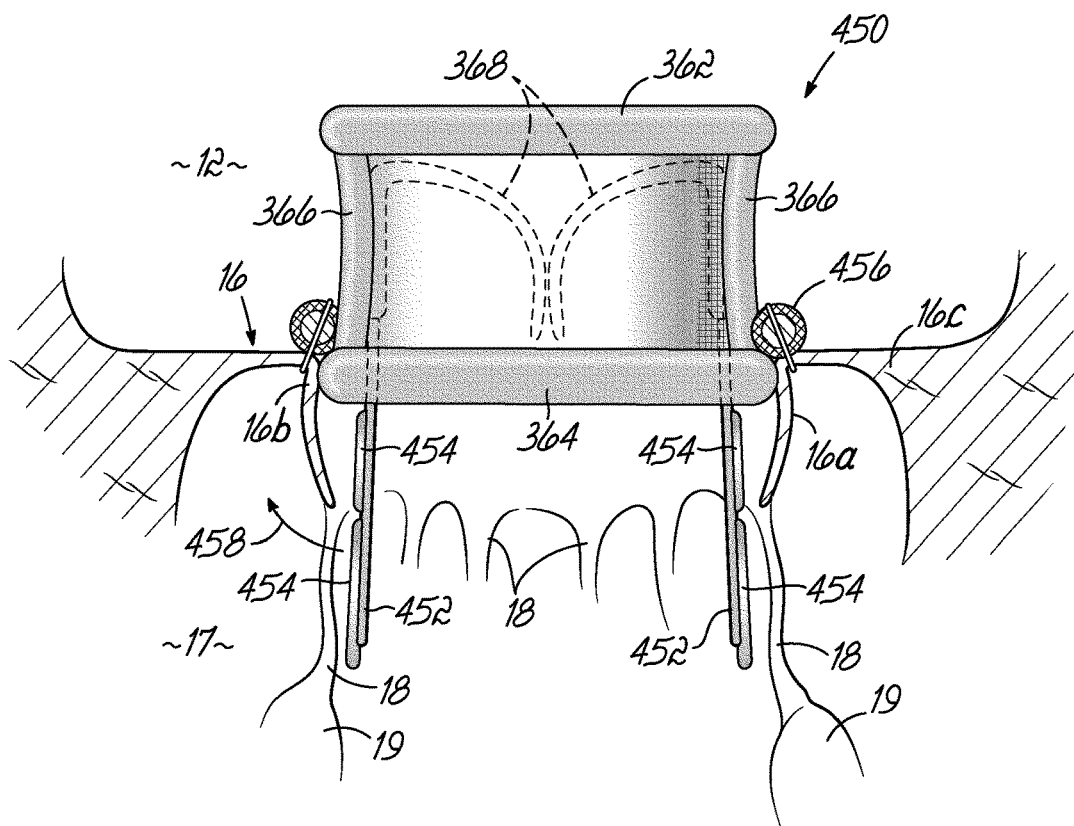
FIG. 29B is a side elevational view illustrating the mitral valve prosthesis of FIG. 29A positioned at the site of a native mitral valve.
Figure 29C:
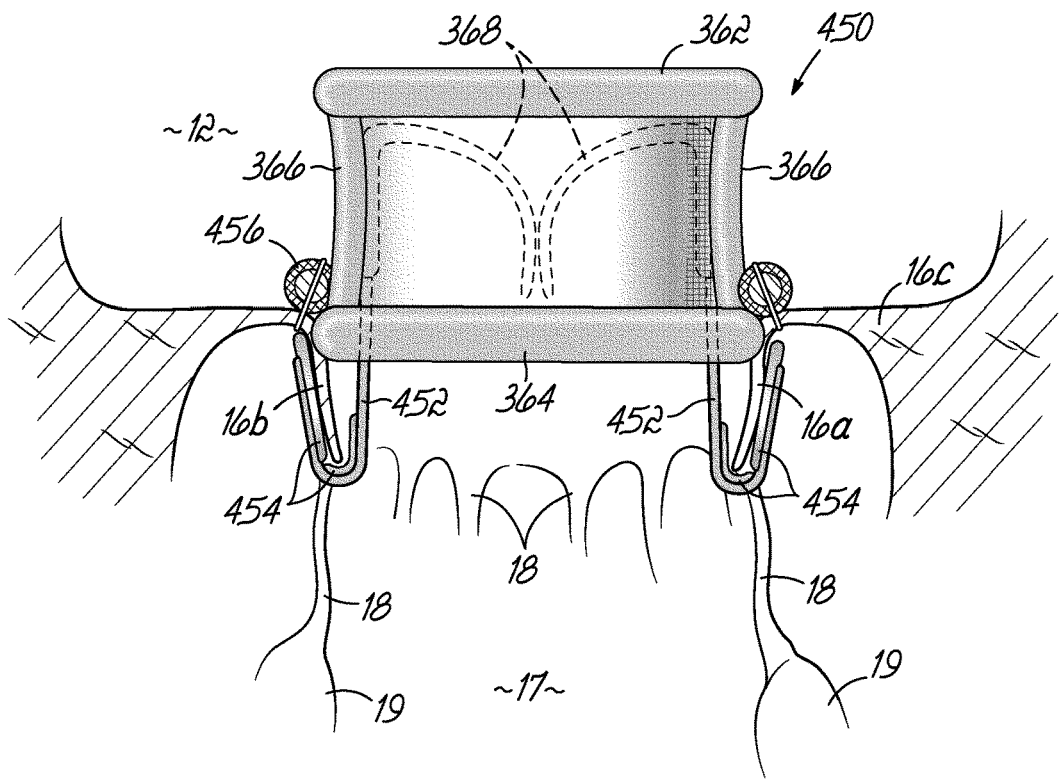
FIG. 29C is a side elevational view illustrating the mitral valve prosthesis similar to FIG. 29B, but illustrating deployment of the anchoring arms.

FIG. 29B illustrates the prosthetic valve 450 positioned at the location of the native mitral valve 16 and the inflatable elements extend beyond the associated anchoring arms 452. An annuloplasty ring 456 has been placed and fixed in a manner that may be conventional. As is known, a catheter procedure is used to insert the prosthetic valve 450 inside the annuloplasty ring 456. In accordance with inventive aspects, however, the inflatable valve prosthesis 450 includes anchoring arms 452 and the anchoring arms include inflatable anchoring elements 454. The anchoring arms 452 fold upwardly as shown by the arrow 458 during deployment. Such deployment is shown in FIG. 29C.

Figure 29D:
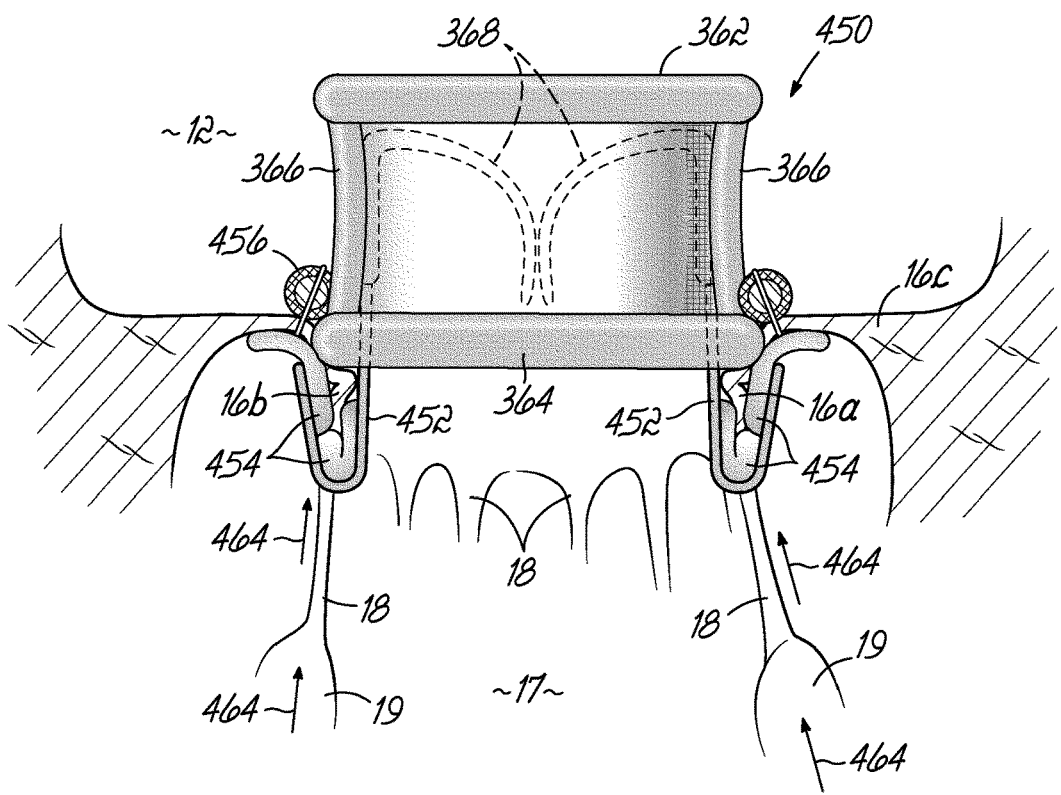
FIG. 29D is a side elevational view similar to FIG. 29C, but further illustrating inflation of the balloon elements associated with the anchoring arms.

FIG. 29D further illustrates that the inflatable elements 454 have been inflated on each anchoring arm 452. There are one or more inflatable anchoring elements 454 on each side of the native mitral valve 16 and, therefore, leaflet tissue 16*a*, 16*b* is trapped between respective inflatable elements or anchors 454. The inflatable anchors 454 also cover the lower part of the anchoring arms 452. Therefore, when the inflatable elements 454 are inflated, the leaflets 16*a*, 16*b* are forced upward and tension the leaflets 16*a*, 16*b* and the chordae 18 as well as the chordal attachments in the papillary muscles 19. This tensions the leaflets 16*a*, 16*b* and the chordae tendinae 18 which are attached to the margins of the leaflets 16*a*, 16*b* as shown by the arrows 460 on the papillary muscle 19 and the chordae tendinae 18. This has a number of favorable effects. First, there is better anchoring to the native mitral leaflets 16*a*, 16*b*. Second, there is no "slack" in the anchoring system. That is, the leaflets 16*a*, 16*b* and the chordae 18 are placed under tension so the prosthesis 450 is less likely to rock or move back and forth as the heart beats. This improves the securement of the valve prosthesis 450 and reduces the risk of late failure. Note also in the figure that the balloon anchor 454 can extend beyond the anchoring arm 452. This balloon anchor 454 sweeps under the mitral leaflets 16*a*, 16*b* allowing a smaller prosthesis to be used. The balloon or inflatable anchors 454 pushed under the annulus 16*c* provide rigidity to the anchoring area. The balloon or inflatable anchors 454 could be larger than shown in FIG. 29D so that, for example, they fill the space under the native leaflets 16*a*, 16*b* and adjacent the left ventricular wall. On one side of the native mitral valve 16, the blood exits the left ventricle through the aortic valve (not shown). It may be better for the anchoring balloon 454 to be smaller near this location to prevent obstruction of blood outflow. The tensioned chordae 18 and leaflets 16*a*, 16*b* are also thought to improve left ventricular function. The shape of the left ventricle becomes more spherical when in a diseased condition. Tensioning the chordae 18 can help to prevent this distortion in the shape of the heart and produce a better functioning, more conical shaped left ventricle.

Figure 30A:
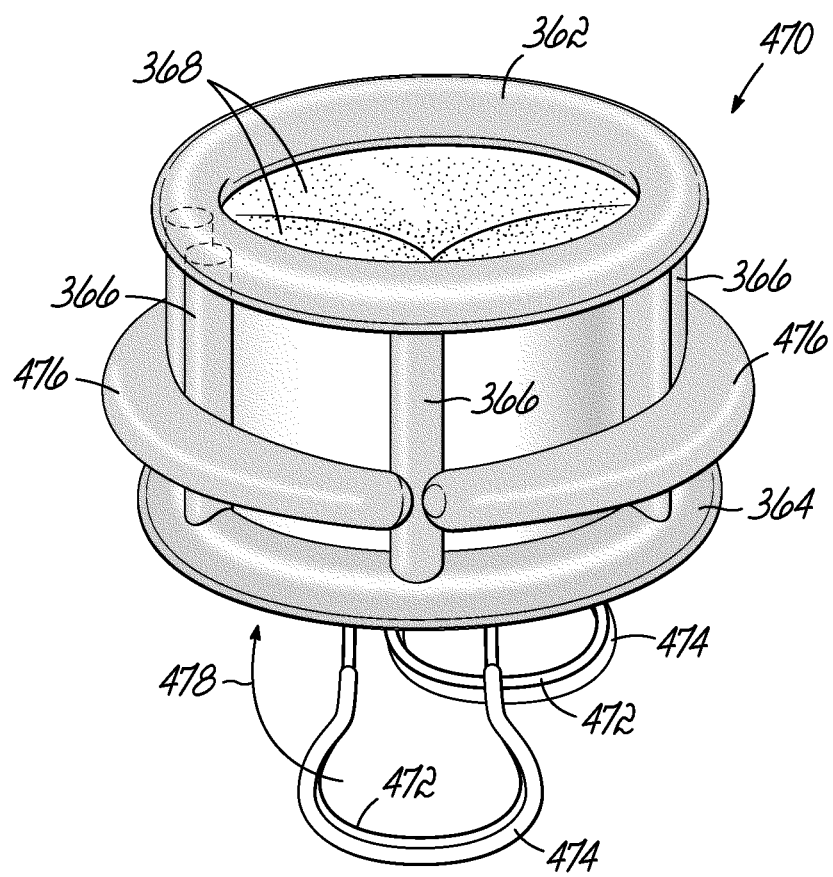
FIG. 30A is a perspective view of another alternative embodiment illustrating an inflatable mitral valve prosthesis with anchoring arms in combination with inflatable balloon elements.
Figure 30B:
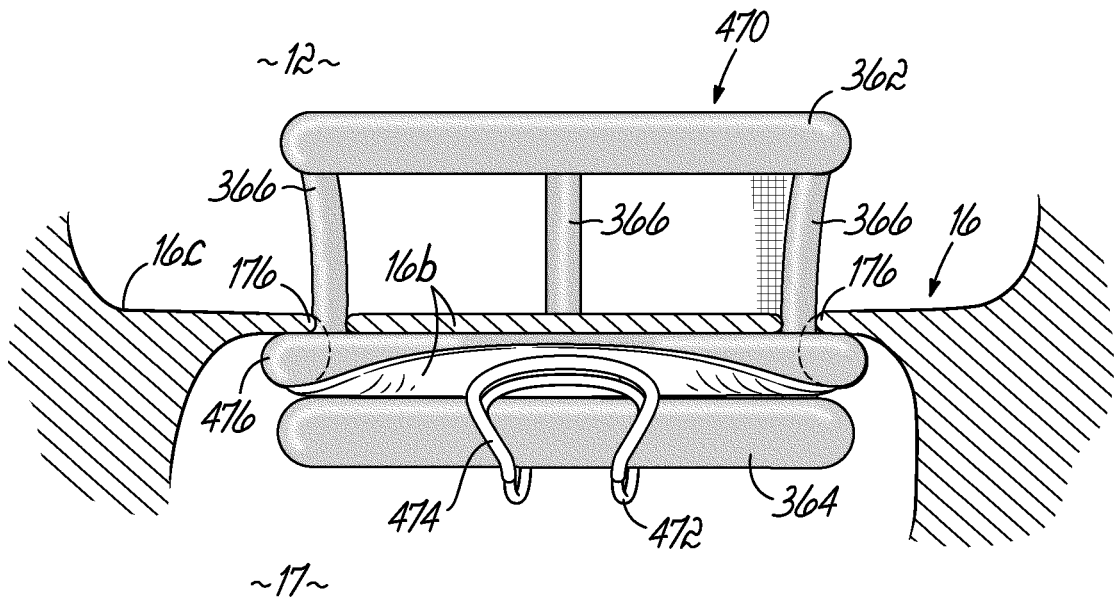
FIG. 30B is a side elevational view of the mitral valve prosthesis of FIG. 30A after delivery within a native mitral valve.
Figure 30C:
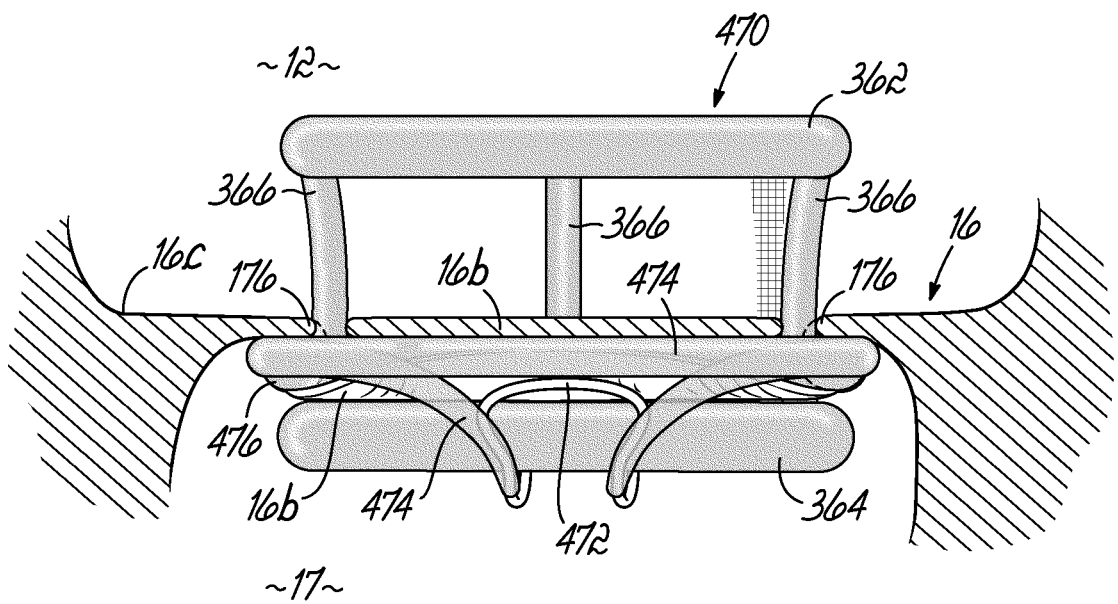
FIG. 30C is a side elevational view similar to FIG. 30B, but illustrating inflation of the balloon elements associated with the anchoring arms.

FIGS. 30A, 30B and 30C illustrate another embodiment of an inflatable mitral valve prosthesis 470 that includes foldable anchoring arms 472 and associated inflatable anchoring elements or anchors 474. This valve 470 also has "bull horn" anchor elements 476 which have been previously described to help anchor the prosthetic valve 470 generally at the level of the native mitral annulus 16*c* or, in other words, generally at the level of the leaflet attachment to the native mitral annulus 16*c*. The anchoring arms 472 wrap around the native mitral leaflets 16*a*, 16*b* generally as discussed above and may be made of Nitinol or other shape memory material so they are in a straightened condition during delivery through a catheter (not shown) and are spontaneously or automatically deployed into their folded condition (FIG. 30B) during delivery from the catheter. This is schematically depicted by the arrow 478 in FIG. 30A. FIG. 30B illustrates the valve prosthesis 470 of FIG. 30A after delivery inside of a native mitral valve 16. In this arrangement, the "bull horn" inflatable anchoring elements 476 reside on the left ventricular side of the native mitral leaflets 16*a*, 16*b*. The lower, circular inflatable element 480 of the prosthesis 470 resides on the atrial side of the native leaflets 16*a*, 16*b* and at a lower level inside the heart. This stabilizes and seals the prosthesis 470 at the level of the native leaflets 16*a*, 16*b*. It is also apparent that the anchoring arms 472 have wrapped around the native leaflets 16*a*, 16*b* and provide additional anchoring. The inflatable elements 474 associated with the anchoring arms 472 have not yet been activated, as illustrated in FIG. 30B. FIG. 30C illustrates the inflatable anchoring elements 474 associated with the anchoring arms 472 in an inflated condition. The inflatable anchoring elements 474 associated with the anchoring arms 472 are partially attached to the anchoring arms 472, but also extend upwardly with portions that are not contacting the anchoring arms 472. Ideally, these inflatable anchors 474 will compress against the underside of the native mitral valve 16 and the base of the heart. The inflatable anchors 474 shown here are loop shaped to provide more mechanical strength to press against the underside of the native mitral valve 16. The inflatable anchoring element 474 forms a continuous loop, however, the loop could instead be discontinuous and/or there could be additional loops or struts joining different segments. The inflatable anchor 474 may vary in shape and, for example, be comprised of separate segments.

Figure 31A:
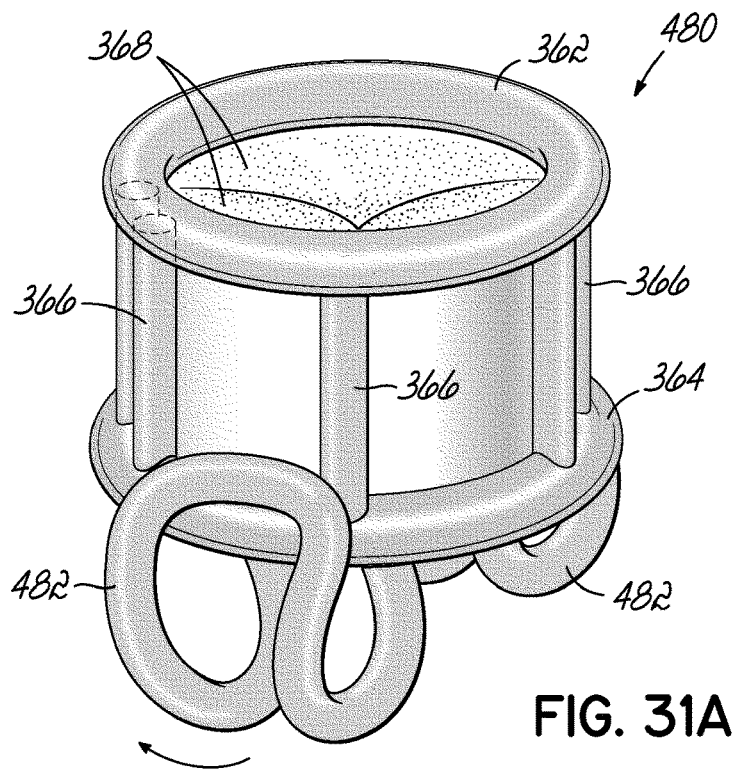
FIG. 31A is a perspective view of another alternative embodiment illustrating an inflatable mitral valve prosthesis with inflatable anchoring arms.
Figure 31B:
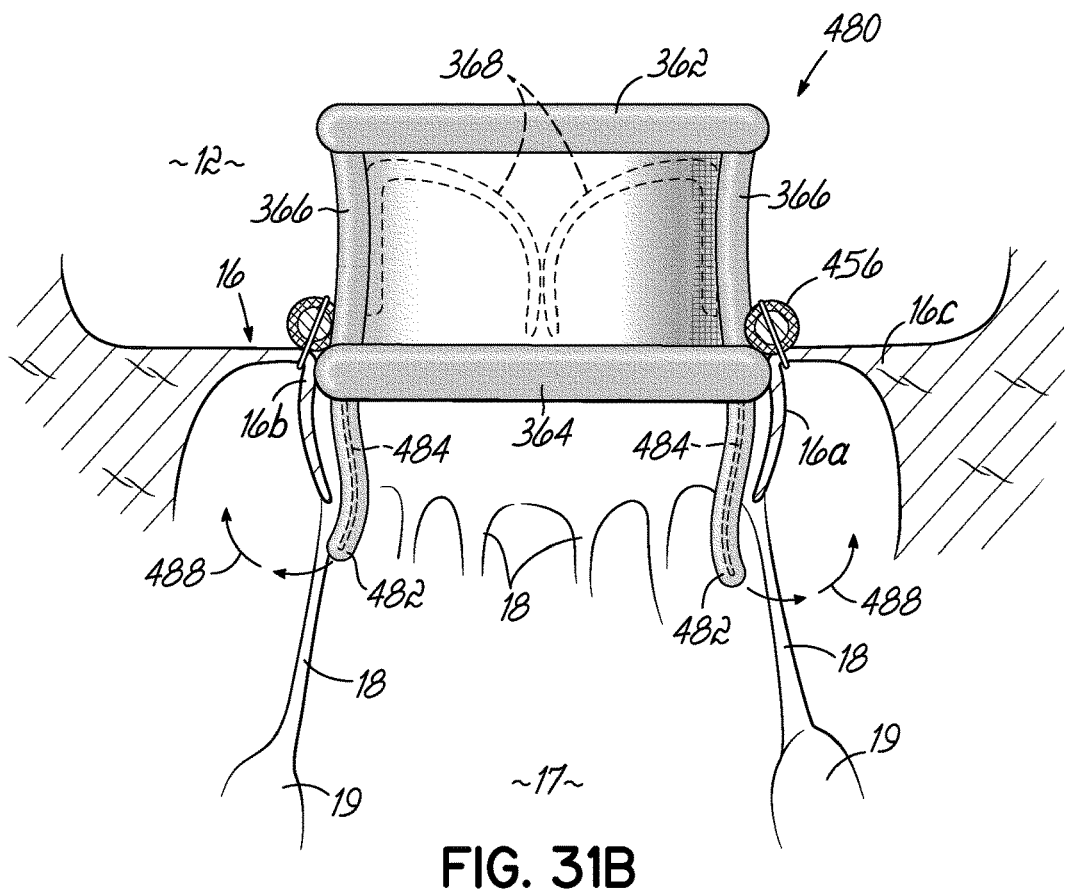
FIG. 31B is a side elevational view showing the mitral valve prosthesis of FIG. 31A in the native mitral valve, but before full deployment of the inflatable anchoring arms.
Figure 31C:
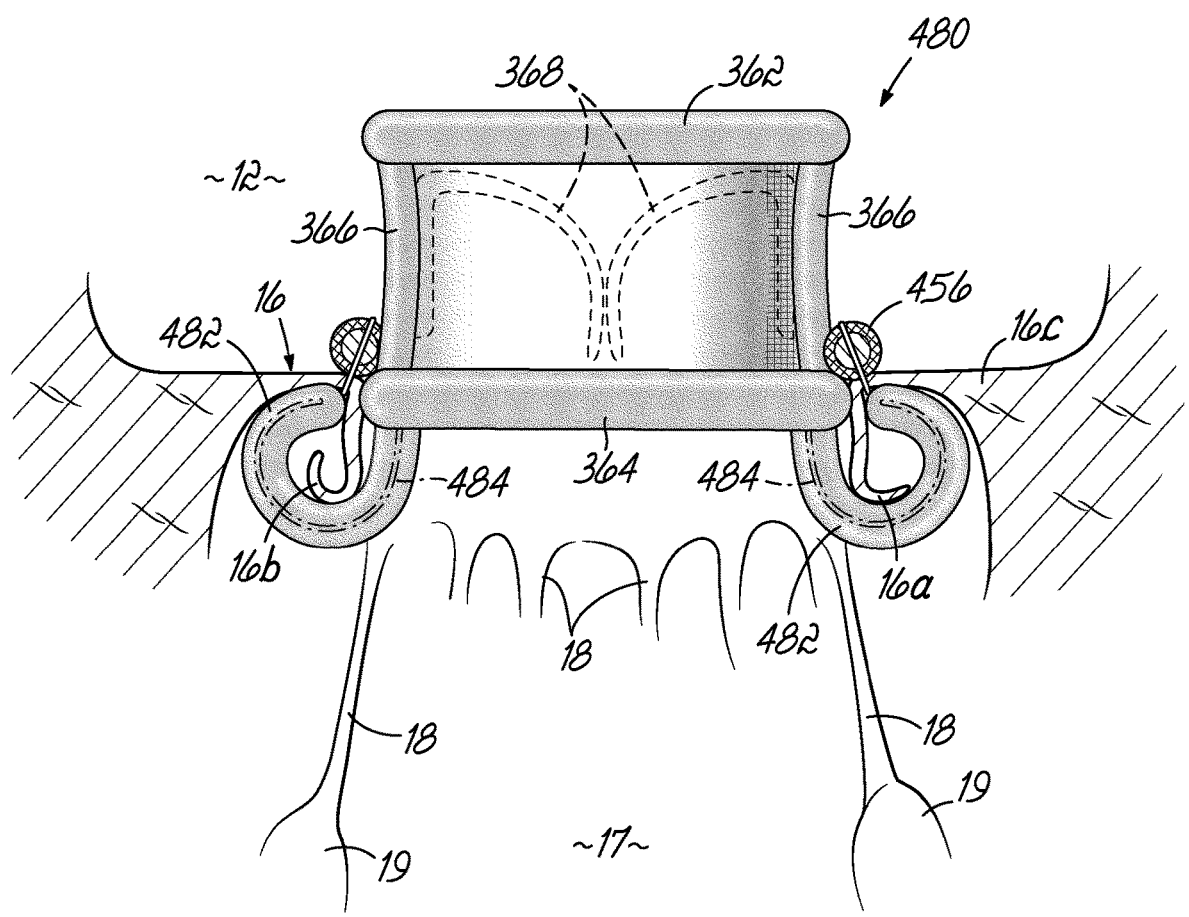
FIG. 31C is a side elevational view similar to FIG. 31B, but illustrating full deployment and inflation of the anchoring arms associated with the mitral valve prosthesis.

FIGS. 31A, 31B and 31C illustrate another alternative embodiment of an inflatable mitral valve prosthesis 480 that further includes inflatable anchoring elements or arms 482. FIG. 31A illustrates the valve prosthesis 480 with the anchoring arms 482 in an inflated condition. As with the remaining portions of the valve prosthesis 480, the anchoring arms 482 may be inflated or filled ultimately with a hardening material for stabilizing purposes. FIG. 31B illustrates wire or other rigid support members 484 in dashed lines used within or otherwise fixedly attached to the inflatable anchoring elements 482 for support purposes. A shape memory material such as Nitinol would serve this function well. The support elements 484 may be positioned inside the fluid cavity of the inflatable anchoring arms 482 or otherwise affixed inside or outside on the wall of the inflatable anchoring arm or element 482. The Nitinol or other shape memory support 484 will force the inflatable anchoring elements 482 into the desired configuration. Such metallic or stiff support elements 484 may be of any desired configuration and in any desired number. The supports 484 could be overlapped to increase the reliability and strength of the anchoring produced by these elements and there may be a number of rigid or stiffened supports 484 to create multiple configurations. The arrows 488 in FIG. 31B illustrate the intended travel of the inflatable anchoring elements 482 around the native mitral leaflets 16*a*, 16*b*. FIG. 31C illustrates the inflatable anchoring elements 482 in their final positions with the native leaflets 16*a*, 16*b* folded, lifted and tensioned, and with the chordae 18 tensioned. As explained previously, the length of the chordae 18, as well as the amount of leaflet tissue and the diameter of the annulus 16*c* are highly variable from patient to patient. Inflation of the anchoring elements 482 that wraps around the mitral leaflets 16*a*, 16*b* can allow for tensioning of the native mitral apparatus (i.e., the valve 16 and chordae tendinae 18) by adjusting the tension. Furthermore, the effective annulus reduction can be achieved with anchors arising or extending from any anchoring arms that wrap around the native leaflets 16*a*, 16*b* or from any structure positioned at or near the level of the native leaflets 16*a*, 16*b* and/or the native annulus 16*c*. For example, inflatable or non-inflatable anchors may extend from the previously described "bull horn" anchor elements. Various combinations of anchoring shown previously with attachments to anchoring arms may also be used with this embodiment. For example, inflatable elements may be shaped to create the native leaflet trapping and the native leaflet folding described in connection with FIGS. 29C and 29D. Wire support or other rigid (i.e., stiffened) support for the inflatable anchoring element may also be applied to other embodiments such as, for example, the devices shown in FIG. 14C and FIG. 14D, which may help facilitate implantation.

Figure 32A:
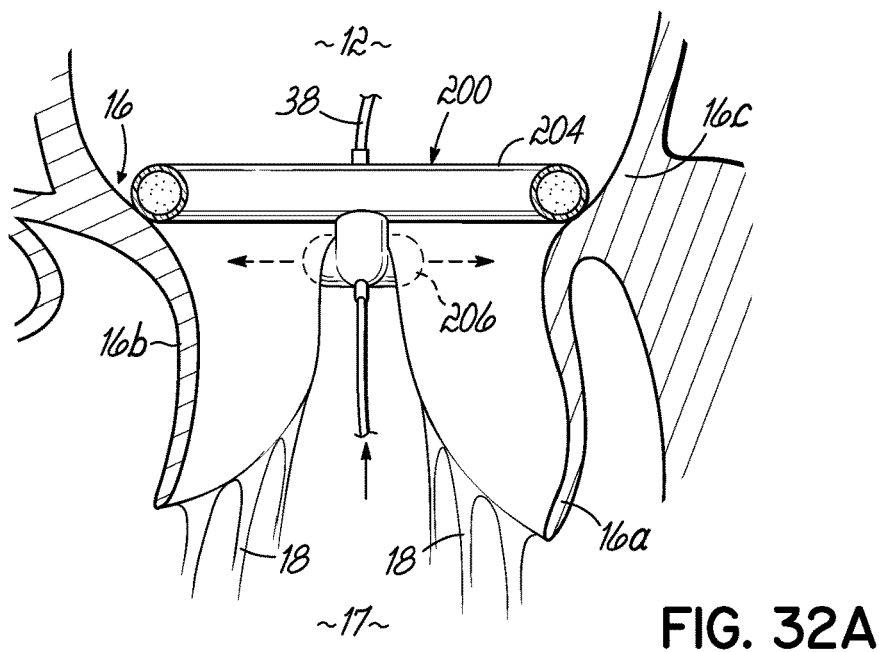
FIG. 32A is an alternative embodiment illustrating inflatable sealing and/or anchoring structure in combination with a mitral clip used for securing the native mitral valve leaflets together.
Figure 32B:
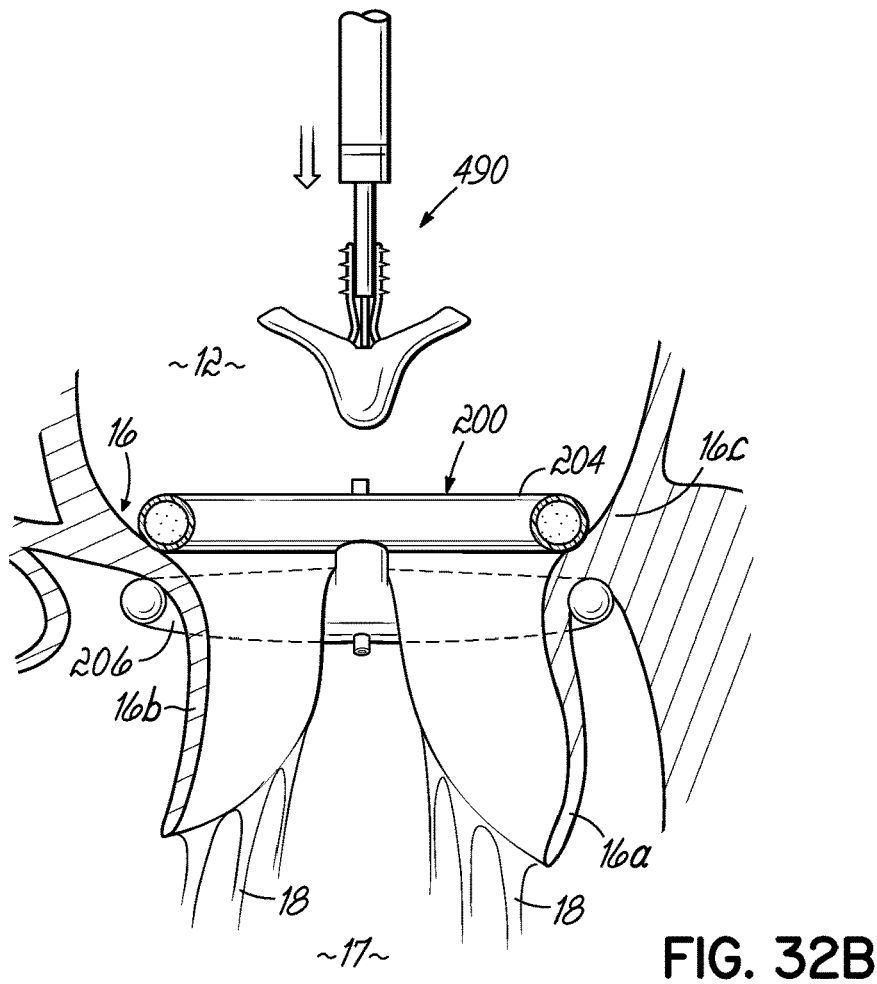
FIG. 32B is a side elevational view similar to FIG. 32A, but illustrating further deployment of the balloon inflatable elements and introduction of the mitral clip via a catheter.
Figure 32C:
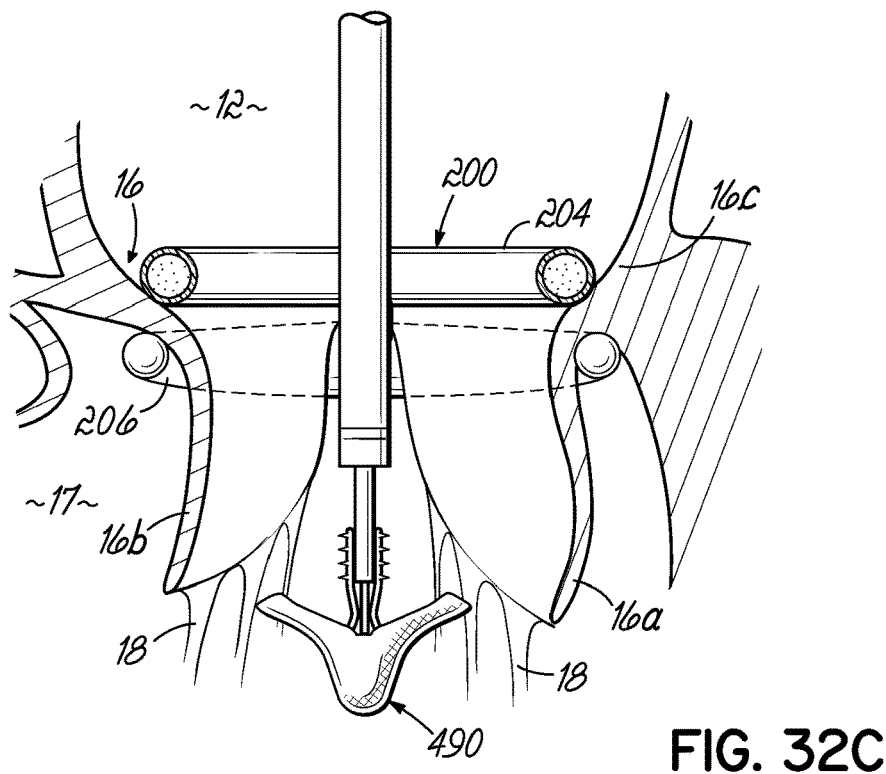
FIG. 32C is a side elevational view similar to FIG. 32B, but illustrating further deployment of the mitral clip beneath the native mitral valve leaflets.
Figure 32D:
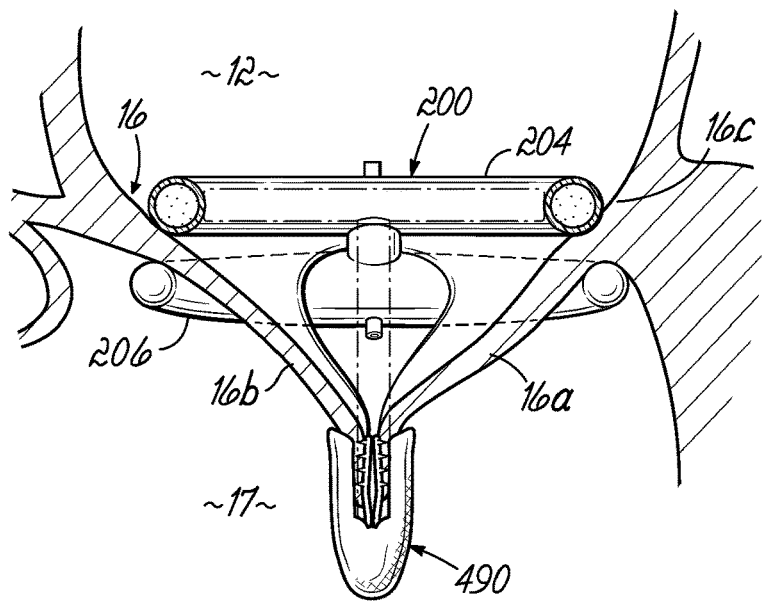
FIG. 32D is a side elevational view similar to FIG. 32C, but illustrating full deployment and implantation of the balloon inflatable structure together with the mitral clip capturing the native mitral valve leaflets.

FIGS. 32A, 32B, 32C and 32D illustrate another alternative embodiment for using an inflatable sealing structure in combination with a known mitral clip apparatus 490. The inflatable sealing structure may be of any suitable types as described and shown herein, with just one example being illustrated in FIGS. 32A-32D. A mitral clip apparatus 490 is shown being applied to the native mitral leaflets 16*a*, 16*b* in a generally known manner in FIGS. 32B-32D in order to clip and permanently secure the native mitral leaflet edges together generally near a midpoint as shown in FIG. 32D. Clipping the native mitral leaflets 16*a*, 16*b* together in this manner effectively creates two openings through the mitral valve 16 on either side of the generally central clip location. This can result in leakage during operation of the valve 16 as the heart beats. An inflatable structure 200, for example, utilizing upper and lower inflatable elements 204, 206 may be physically connected with the clip structure 490 as shown in dashed lines in FIG. 32D, or may be used in a completely independent manner detached from the clip structure 490 for purposes of assisting with the sealing of the native mitral valve 16 and the prevention of leakage as the heart beats. The inflatable sealing structure 200 chosen to exemplify this concept is that more fully shown and described in connection with FIGS. 12A and 12B. It will be appreciated that other inflatable sealing structures may be substituted, such as many of those shown and described herein.

Figure 33A:
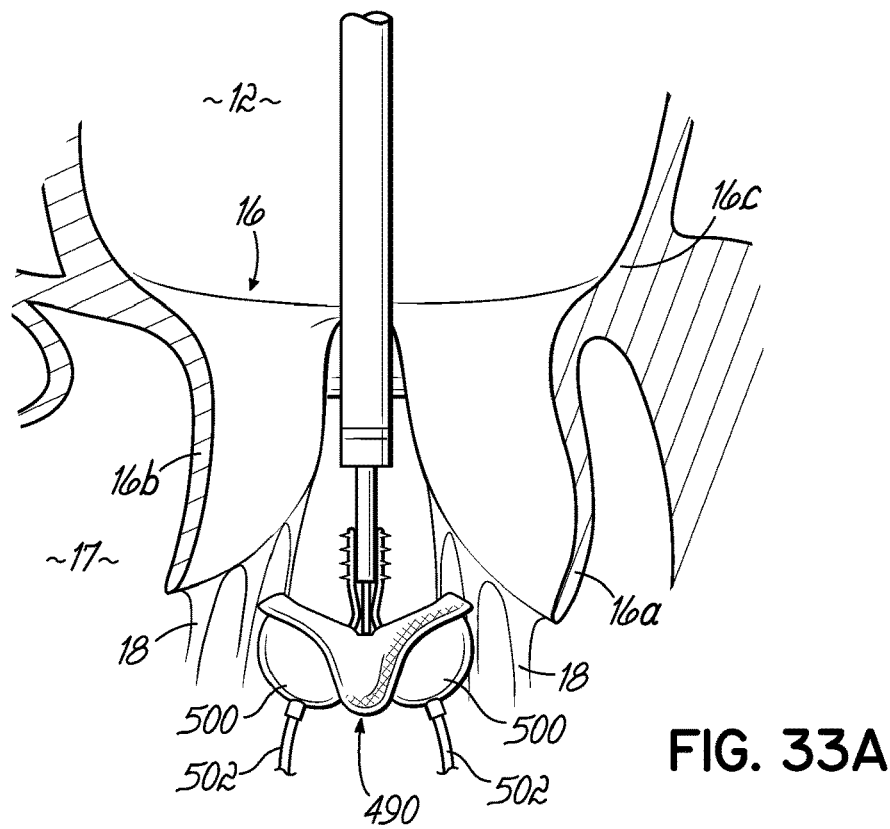
FIGS. 33A and 33B are side elevational views similar to FIGS. 32C and 32D, but illustrating an alternative embodiment with inflatable connectors deployed from the mitral clip and coupling the mitral clip to the inflatable sealing structure.
Figure 33B:
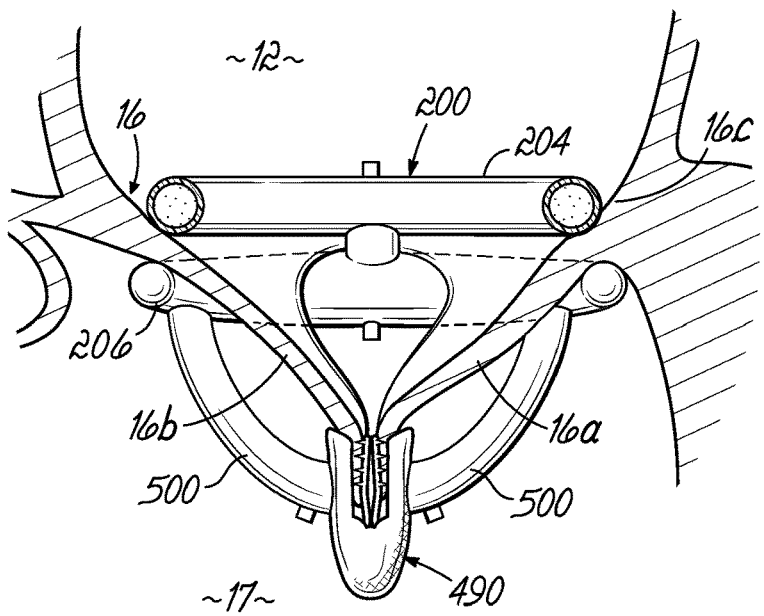

FIGS. 33A and 33B illustrate another alternative embodiment for using an inflatable sealing structure in combination with a known mitral clip apparatus 490. This embodiment is similar to that described above in connection with FIGS. 32A-32D. The inflatable sealing structure may be of any suitable types as described and shown herein, with just one example being illustrated in FIGS. 32A-32D. A mitral clip apparatus 490 is shown being applied to the native mitral leaflets 16*a*, 16*b* in a generally known manner as also shown and described in connection with FIGS. 32B-32D in order to clip and permanently secure the native mitral leaflet edges together generally near a midpoint as shown in FIG. 32D. As previously mentioned, this can result in leakage during operation of the valve 16 as the heart beats. An inflatable structure 200, for example, utilizing upper and lower inflatable elements 204, 206 is physically connected with the clip structure 490 by a portion 500 of the inflatable structure 200. The inflatable connecting portion 500 may be inflated with fluid delivered by tubes 502. It will be appreciated that separate tubes 38 (FIG. 32A) may be used for the inflatable sealing structure 200, or the same supply may be used for the entire inflatable structure 200, 500. The inflatable sealing structure 200 chosen to exemplify this concept is that more fully shown and described in connection with FIGS. 12A and 12B. It will be appreciated that other inflatable sealing structures may be substituted, such as many of those shown and described herein.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. An inflatable anchor system for a mitral valve prosthesis, comprising:
    a continuous annular balloon capable of being delivered to a native mitral valve of a heart of a patient, on an atrial side of native mitral valve leaflets of the native mitral valve; and
    an inflatable anchor formed in a generally annular or semi-annular shape, the inflatable anchor including a portion that is capable of being inflated at a position below a native mitral valve annulus of the native mitral valve, on a ventricular side of the native mitral valve leaflets;
    wherein the inflatable anchor is configured for positioning below the native mitral valve annulus, on the ventricular side of the native mitral valve leaflets, and the continuous annular balloon is configured for positioning on the atrial side of the native mitral valve leaflets to assist in anchoring the mitral valve prosthesis by trapping the native mitral valve leaflets between the continuous annular balloon and the inflatable anchor, and
    wherein the inflatable anchor comprises discrete inflatable elements for locating between a left ventricular wall and chordae tendinae of the native mitral valve.

2. The system of claim 1, further comprising a wire operatively coupled to the inflatable anchor and configured to guide the inflatable anchor under at least a portion of the native mitral valve.

3. The system of claim 1, wherein the discrete inflatable elements include discrete and separately inflatable balloons.

4. The system of claim 1, wherein the discrete inflatable elements include first and second inflatable leaflet capturing members configured to be inflated to capture and stabilize the native mitral valve leaflets.

5. The system of claim 1, further comprising a plurality of anchoring arms configured to engage the inflatable anchor and/or at least one of the native mitral valve leaflets.

6. The system of claim 5, wherein the anchoring arms further include hook-like members.

7. The system of claim 1, wherein the inflatable anchor includes two of the discrete inflatable elements, each having a generally semi-annular, elongate shape to generally follow a curvature of the native mitral valve annulus.

8. The system of claim 1, further comprising:
a wire operatively coupled to the inflatable anchor and configured to guide the inflatable anchor into position between the left ventricular wall and chordae tendinae and/or the native mitral valve leaflets and to generally follow a curvature of the native mitral valve annulus.

9. The system of claim 1, further comprising a reinforcing structure coupled with the inflatable anchor.

10. The system of claim 9, wherein the reinforcing structure further includes wire.

11. The system of claim 1, wherein the portion that is capable of being inflated at the location of the native mitral valve annulus at least assists with sealing a commissure of the native mitral valve against blood leakage.

12. The system of claim 1, wherein the inflatable anchor is connected to the continuous annular balloon.

13. The system of claim 1, wherein the continuous annular balloon is configured to be positioned at a lower level than the inflatable anchor on the atrial side of the native mitral valve leaflets.

14. The system of claim 1, wherein the continuous annular balloon is configured to be positioned above the native mitral leaflets on the atrial side of the native mitral valve.

15. An inflatable mitral valve prosthesis system comprising the inflatable anchor system for a mitral valve prosthesis of claim 1, and a mitral valve prosthesis.

16. The system of claim 15, further comprising an inflatable structure capable of being positioned between the mitral valve prosthesis and the native mitral valve and capable of being delivered to the native mitral valve separately from the mitral valve prosthesis.

17. The system of claim 15, wherein the mitral valve prosthesis is capable of being delivered to the native mitral valve of the patient separately from the inflatable anchor system and expanded radially outward and into engagement with the inflatable anchor.

18. The system of claim 15, wherein the mitral valve prosthesis includes a generally tubular portion, with the continuous annular balloon providing a flange portion extending radially outward from the tubular portion.

19. The system of claim 15, wherein the inflatable anchor is shaped to generally follow the native mitral valve annulus and allows for the mitral valve prosthesis to be implanted, wherein the mitral valve prosthesis has a smaller diameter than the native mitral valve annulus.

20. An inflatable mitral valve prosthesis comprising:
a generally circular inflatable support structure capable of being delivered to a native mitral valve of a heart of a patient, the inflatable support structure including a continuous annular balloon;
an inflatable anchor formed in a generally annular or semi-annular shape, the inflatable anchor including a portion that is capable of being inflated at a position below a native mitral valve annulus of the native mitral valve, on a ventricular side of native mitral valve leaflets of the native mitral valve; and
prosthetic leaflets fixed within the inflatable support structure;
wherein the inflatable anchor is configured for positioning below the native mitral valve annulus, on the ventricular side of the native mitral valve leaflets, and the continuous annular balloon is configured for positioning on an atrial side of the native mitral valve leaflets to assist in anchoring the mitral valve prosthesis by trapping the native mitral valve leaflets between the continuous annular balloon and the inflatable anchor, and
wherein the inflatable anchor comprises discrete inflatable elements for locating between a left ventricular wall and chordae tendinae of the native mitral valve.

21. The inflatable mitral valve prosthesis of claim 20, wherein the inflatable support structure further includes a generally tubular portion and the continuous annular balloon is a flange portion extending radially outward from the tubular portion.

22. The inflatable mitral valve prosthesis of claim 20, wherein:
the inflatable anchor includes two of the discrete inflatable elements,
the two discrete inflatable elements configured to be delivered through commissures of the native mitral valve and then inflated below the level of the native mitral valve leaflets, resulting in the two discrete inflatable elements being positioned on the ventricular side of the native mitral valve leaflets and with the continuous annular balloon remaining on the atrial side of the native mitral valve leaflets to trap the native mitral valve leaflets between the two discrete inflatable elements and the continuous annular balloon.

23. The inflatable mitral valve prosthesis of claim 22, wherein the continuous annular balloon is a bottom circular inflatable support of the inflatable support structure, and the inflatable support structure further includes a top circular inflatable support, at a top of the prosthesis.

24. The inflatable mitral valve prosthesis of claim 20, wherein:
the continuous annular balloon is configured to sit at a lower level than the discrete inflatable elements,
the discrete inflatable elements are configured to be positioned on the ventricular side of the native mitral leaflets and the continuous annular balloon is configured to be positioned on the atrial side of the native mitral valve leaflets, the native mitral valve leaflets passing between the discrete inflatable elements and the continuous annular balloon, with the discrete inflatable elements and the continuous annular balloon constructed so that after inflation they overlap and help trap the native mitral valve leaflets therebetween for a secure prosthetic valve attachment.

25. The inflatable mitral valve prosthesis of claim 20, wherein:
the inflatable anchor includes two of the discrete inflatable elements, the two discrete inflatable elements positioned below the continuous annular balloon,
the two discrete inflatable elements configured to be positioned under each of the native mitral valve leaflets on the ventricular side of the native mitral valve leaflets, and
the continuous annular balloon configured to be positioned above the native mitral valve leaflets on the atrial side of the native valve.

* * * * *